United States Patent
Wong et al.

(10) Patent No.: US 10,568,970 B2
(45) Date of Patent: Feb. 25, 2020

(54) THERANOSTIC COMPOSITIONS AND USES THEREOF

(71) Applicant: TRUSTEES OF BOSTON UNIVERSITY, Boston, MA (US)

(72) Inventors: Joyce Y. Wong, Chestnut Hill, MA (US); Ragnhild D. Whitaker, Boston, MA (US); Nelson Ruiz-Opazo, Westwood, MA (US); Victoria L. M. Herrera, Westwood, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 29 days.

(21) Appl. No.: 15/551,743

(22) PCT Filed: Feb. 18, 2016

(86) PCT No.: PCT/US2016/018417
§ 371 (c)(1),
(2) Date: Aug. 17, 2017

(87) PCT Pub. No.: WO2016/134115
PCT Pub. Date: Aug. 25, 2016

(65) Prior Publication Data
US 2018/0028683 A1 Feb. 1, 2018

Related U.S. Application Data

(60) Provisional application No. 62/157,623, filed on May 6, 2015, provisional application No. 62/118,817, filed on Feb. 20, 2015.

(51) Int. Cl.
| A61K 47/69 | (2017.01) |
| A61K 49/18 | (2006.01) |
| A61K 47/60 | (2017.01) |
| A61K 48/00 | (2006.01) |

(52) U.S. Cl.
CPC .......... *A61K 47/6931* (2017.08); *A61K 47/60* (2017.08); *A61K 47/6923* (2017.08); *A61K 47/6925* (2017.08); *A61K 48/0041* (2013.01); *A61K 49/186* (2013.01); *A61K 49/1875* (2013.01)

(58) Field of Classification Search
None
See application file for complete search history.

(56) References Cited

U.S. PATENT DOCUMENTS

| 7,999,025 B2 | 8/2011 | Shumaker-Parry |
| 2011/0054236 A1 | 3/2011 | Yang |
| 2012/0156135 A1* | 6/2012 | Farokhzad ............... A61K 8/14 424/9.1 |
| 2013/0171208 A1 | 7/2013 | Smith |

FOREIGN PATENT DOCUMENTS

| WO | 2009/117688 A2 | 9/2009 |
| WO | 2010/051643 A1 | 5/2010 |

OTHER PUBLICATIONS

Xu, C., et al., "Au—Fe3O4Dunnbbell Nanoparticles as Dual-Functional Probes", Angew. Chem. Int. Ed., 2008, pp. 173-176 (Year: 2008).*
Fruit Shapes, "Descriptors for Avocado (*Persea* spp.)", accessed from: http://ucavo.ucr.edu/General/FruitShape.html, accessed on: Mar. 2, 2019, pp. 1 (Year: 2019).*
Cauda, V., et al., "Impact of different PEGylation patterns on the long-term bio-stability of colloidal mesoporous silica nanoparticles", J. Mater. Chem., 2010, pp. 8693-8699 (Year: 2010).*
Mannell, H., et al., "Site directed vascular gene delivery in vivo by ultrasonic destruction of magnetic nanoparticle coated microbubbles", Nanomedicine, 2012, pp. 1309-1318 and supplemental data pp. 1-5 (Year: 2012).*
Barrefelt et al., "Biodistribution, kinetics, and biological fate of SPION microbubbles in the rat", Int J Nanomedicine 8: 214-254 (2013).
Budijono et al., "Block copolymer surface coverage on nanoparticles", Colloids and Surface A: Physicochemical and Engineering Aspects 360(1-3) 105-110 (2010).
Cai et al., "Applications of magnetic microbubbles for theranostics", Theranostics 2: 103-112 (2012).
Chow et al., "Enhancement of gas-filled microbubble magnetic susceptibility by iron oxide nanoparticles", Proc Intl Soc Mag Reson Med 17 (2009).
Cruz et al., "The influence of PEG chain length and targeting moiety on antibody-mediated delivery of nanoparticle vaccines to human dendritic cells", Biomaterials 32(28) 6791-6803 (2011).
Decano et al., "Molecular imaging of vasa vasorum neovascularization via DEspR-targeted contrast-enhanced ultrasound microimaging in transgenic atherosclerosis rat model", Mol Imaging Biol 13(6) 1096-1106 (2011).
Delalande et al., "Sonoporation: mechanistic insights and ongoing challenges for gene transfer", Gene 525(2) 191-199 (2013).
Escoffre et al., "Doxorubicin liposome-loaded microbubbles for contrast imaging and ultrasound-triggered drug delivery", IEEE Trans Ultrason Ferroelectr Freq Control 60(1) 78-87 (2013).
Escoffre et al., "Irinotecan delivery by microbubble-assisted ultrasound: in vitro validation and a pilot preclinical study", Mol Pharm 10(7) 2667-2675 (2013).
Escoffre et al., "Microbubble attenuation and destruction: are they involved in sonoporation efficiency?", IEEE Trans Ultrason Ferroelectr Freq Control 60(1) 46-52 (2013).

(Continued)

*Primary Examiner* — Michael G. Hartley
*Assistant Examiner* — Lance W Rider
(74) *Attorney, Agent, or Firm* — Nixon Peabody LLP; Ronald I. Eisenstein; Teresa A. Ptashka

(57) ABSTRACT

Provided herein are theranostic compositions comprising a Janus nanoparticle-coated microbubble that are useful for imaging (e.g., MRI, or ultrasound) and for delivering a therapeutic or bioactive agent (e.g., nucleic acid(s), drugs, etc), among other uses.

15 Claims, 40 Drawing Sheets

(56) References Cited

OTHER PUBLICATIONS

Gao et al., "Drug-loaded nano/microbubbles for combining ultrasonography and targeted chemotherapy", Ultrasonics 48(4) 260-270 (2008).
Gilleron et al., "Image-based analysis of lipid nanoparticle-mediated siRNA delivery, intracellular trafficking and endosomal escape", Nat Biotechnol 31(7) 638-646 (2013).
He et al., "Microbubbles with surface coated by superparamagnetic iron oxide nanoparticles", Materials Letters 68(1) 64-67 (2012).
Hernot et al., "Microbubbles in ultrasound-triggered drug and gene delivery", Adv Drug Deliv Rev 60(10) 1153-1166 (2008).
Herrera et al., "DEspR Roles in Tumor Vasculo-Angiogenesis, Invasiveness, CSC-Survival and Anoikis Resistance: A 'Common Receptor Coordinator' Paradigm", PLoS One 9(10) e112335 (2014).
Hu et al., "Nanocomposites with spatially separated functionalities for combined imaging and magnetolytic therapy", J Am Chem Sco 132(21) 7234-7237 (2010).
Jin et al., "A novel cationic microbubble coated with stearic acid-modified polyethylenimine to enhance DNA loading and gene delivery by ultrasound", PLoS One 8(9) e76544 (2013).
Jokerst et al., "Nanoparticle PEGylation for imaging and therapy", Nanomedicine (Lond) 6(4) 715-728 (2011).
Lattuada et al., "Functionalization of Monodisperse Magnetic Nanoparticles", Langmuir 23(4) 2158-2168 (2007).
Lattuada et al., "Preparation and controlled self-assembly of Janus magnetic nanoparticles", J Am Chem Soc 129(42) 12878-12889 (2007).
Lattuada et al., "Synthesis, properties and applications of Janus nanoparticles", Nano Today 6(3) 286-308 (2011).
Lee et al., "All-in-one target-cell-specific magnetic nanoparticles for simultaneous molecular imaging and siRNA delivery", Angew Chem Int Ed Engl 48(23) 4174-4179 (2009).
Lentacker et al., "Design and evaluation of doxorubicin-containing microbubbles for ultrasound-triggered doxorubicin delivery: cytotoxicity and mechanisms involved", Mol Ther 18(1) 101-108 (2010).
Li et al., Cruz et al., "Comparison of Two Ultrasmall Superparamagnetic Iron Oxides on Cytotoxicity and MR Imaging of Tumors", Therapnostics 2(1) 76-85 (2012).
Liu et al., "Iron oxide nanoparticle-containing microbubble composites as contrast agents for MR and ultrasound dual-modality imaging", Biomaterials 32(26) 6155-6163 (2011).
Torchilin, "Multifunctional nanocarriers", Advanced Drug Delivery Reviews 64(Supplement) 302-315 (2012).
Migneault et al., "Glutaraldehyde: behavior in aqueous solution, reaction with proteins, and application to enzyme crosslinking", Biotechniques 37(5) 790-796 (2004).
Mullin et al., "Nanoparticle delivery enhancement with acoustically activated microbubbles", IEEE Trans Ultrason Ferroelectr Freq Control 60(1) 65-77 (2013) . . . .
Mykhaylyk et al., "Magnetic nanoparticle formulations for DNA and siRNA delivery", Journal of Magnetism and Magnetic Materials 311(1) 275-281 (2007).
Nitin et al., "Functionalization and peptide-based delivery of magnetic nanoparticles as an intracellular MRI contrast agent", J Biol Inorg Chem 9(6) 706-712 (2004).
Niu et al., "Doxorubicin loaded superparamagnetic PLGA-iron oxide multifunctional microbubbles for dual-mode US/MR imaging and therapy of metastasis in lymph nodes", Biomaterials 34(9) 2307-2317 (2013). Abstract Only.
Olive et al., "Inhibition of Hedgehog signaling enhances delivery of chemotherapy in a mouse model of pancreatic cancer", Science 324(5933) 1457-1461 (2009).
Panje et al., "Ultrasound-mediated gene delivery with cationic versus neutral microbubbles: effect of DNA and microbubble dose on in vivo transfection efficiency", Theranostics 2(11) 1078-1091 (2012).
Park et al., "Effect of PEG molecular weight on stability, $T_2$ contrast, cytotoxicity, and cellular uptake of superparamagnetic iron oxide nanoparticles (SPIONs)", Colloids Surf B Biointerfaces 119: 106-114 (2014).
Phillips et al., "Intravascular ultrasound detection and delivery of molecularly targeted microbubbles for gene delivery", IEEE Trans Ultrason Ferroelectr Freg Control 59(7) 1596-1601 (2012).
Ren et al., "Iron oxide nanoparticle-based theranostics for cancer imaging and therapy", Front Chem Sci Eng 8(3) 253-264 (2014).
Sardar et al., "Asymmetrically functionalized gold nanoparticles organized in one-dimensional chains", Nano Lett 8(2) 731-736 (2008).
Sardar et al., "Versatile solid phase synthesis of gold nanoparticle dimers using an asymmetric functionalization approach", J Am Chem Soc 129(17) 5356-5357 (2007).
Schick et al., "Multifunctional two-photon active silica-coated Au@MnO Janus particles for selective dual functionalization and imaging", J Am Chem Sco 136(6) 2473-2483 (2014).
Seo et al., "Microfluidic assembly of monodisperse, nanoparticle-incorporated perfluorocarbon microbubbles for medical imaging and therapy", Langmuir 26(17) 13855-13860 (2010).
Shi et al., "Self-assembled targeted nanoparticles: evolution of technologies and bench to bedside translation", Acc Chem Res 44(10) 1123-1134 (2011).
Singh et al., "Potential toxicity of superparamagnetic iron oxide nanoparticles (SPION).", Nano Res 1 (2010).
Sirsi et al., "Microbubble Compositions, Properties and Biomedical Applications", Bubble Sci Engl Technol 1(1-2) 3-17 (2009).
Song et al., "Self-assembled Fe3O4/polymer hybrid microbubble with MRI/ultrasound dual-imaging enhancement", Langmuir 30(35) 10557-10561 (2014).
Sumer et al., "Theranostic nanomedicine for cancer", Nanomedicine (Lond) 3(2) 137-140 (2008).
Sun et al., "Development of therapeutic microbubbles for enhancing ultrasound-mediated gene delivery", J Control Release 182: 111-120 (2014).
Sun et al., "In Vitro Acoustic Characterization of Three Phospholipid Ultrasound Contrast Agents from 12 to 43 MHz", Ultrasound in Medicine & Biology 40(3) 541-550 (2014).
Sun et al., "Monodisperse MFe2O4 (M=Fe, Co, Mn) nanoparticles", J Am Chem Soc 126(1) 273-279 (2004).
Taratula et al., "Multifunctional nanomedicine platform for cancer specific delivery of siRNA by superparamagnetic iron oxide nanoparticles-dendrimer complexes", Curr Drug Deliv 8(1) 59-69 (2011).
Tros De Ilarduya et al., "Gene delivery by lipoplexes and polyplexes", Eur J Pharm Sci 40(3) 159-170 (2010).
Tsutsui et al., "The use of microbubbles to target drug delivery", Cardiovasc Ultrasound 2: 23 (2004).
Vasquez et al., "Janus magnetic nanoparticles with a bicompartmental polymer brush prepared using electrostatic adsorption to facilitate toposelective surface-initiated ATRP", Langmuir 30(23) 6858-6866 (2014).
Vigor et al., "Nanoparticles functionalized with recombinant single chain Fv antibody fragments (scFv) for the magnetic resonance imaging of cancer cells", Biomaterials 31(6) 1307-1315 (2010).
Vlaskou et al., "Magnetic and Acoustically Active Liposheres for Magnetically Targeted Nucleic Acid Delivery", Advanced Functional Materials 20(22) 3881-3894 (2010).
Vlaskou et al., "Magnetic Microbubbles: Magnetically Targeted and Ultrasound-Triggered Vectors for Gene Delivery in Vitro", AIP Conference Proceedings 1311(1) 485-494 (2010).
Wang et al., "Amphiphilic Janus gold nanoparticles via combining "solid-state grafting-to" and "grafting-from" methods", J Am Chem Soc 130(35) 11594-11595 (2008).
Wang et al., "Biofunctionalized phospholipid-capped mesoporous silica nanoshuttles for targeted drug delivery: improved water suspensibility and decreased nonspecific protein binding", ACS Nano 4(8) 4371-4379 (2010).
Wang et al., "Cationic versus neutral microbubbles for ultrasound-mediated gene delivery in cancer", Radiology 264(3) 721-732 (2012).
Wang et al., "Enhanced hepatic delivery of siRNA and microRNA using oleic acid based lipid nanoparticle formulations", J Control Release 172(3) 690-698 (2013).

(56) References Cited

OTHER PUBLICATIONS

Wang et al., "Superparamagnetic Hyperbranched Polyglycerol-Grafted Fe3O4 Nanoparticles as a Novel Magnetic Resonance Imaging Contrast Agent: An In Vitro Assessment", TOC 19(16) 2615-2622 (2009).

Willmann et al., "Targeted contrast-enhanced ultrasound imaging of tumor angiogenesis with contrast microbubbles conjugated to integrin-binding knottin peptides", J Nucl Med 51(3) 433-440 (2010).

Wu et al., "Efficacy of contrast-enhanced US and magnetic microbubbles targeted to vascular cell adhesion molecule-1 for molecular imaging of atherosclerosis", Radiology 260(2) 463-471 (2011).

Zhou et al., "Targeted antiangiogenesis gene therapy using targeted cationic microbubbles conjugated with CD105 antibody compared with untargeted cationic and neutral microbubbles", Theranostics 5(4) 399-417 (2015).

Xie et al., "Nanoparticle-based theranostic agents", Adv Drug Deliv Rev 62(11) 1064-1079 (2010).

Xie et al., "Ultrasound-mediated vascular gene transfection by cavitation of endothelial-targeted cationic microbubbles", JACC Cardiovasc Imagin 5(12) 1253-1262 (2012).

Yang et al., "Superparamagnetic iron oxide nanoparticle-embedded encapsulated microbubbles as dual contrast agents of magnetic resonance and ultrasound imaging", Biomaterials 30(23-24) 3882-3890 (2009).

Yang et al., "Superparamagnetic nanoparticle-inclusion microbubbles for ultrasound contrast agents", Phys Med Biol 53(21) 6129-6141 (2008).

Yen et al., "Multifunctional iron oxide nanoparticles for diagnostics, therapy and macromolecule delivery", Theranostics 3(12) 986-1003 (2013).

Yu et al., "Cell experimental studies on sonoporation: state of the art and remaining problems", J Control Release 174: 151-160 (2014).

Zhang et al., "Progress in microRNA delivery", J Control Release 172(3) 962-974 (2013).

* cited by examiner

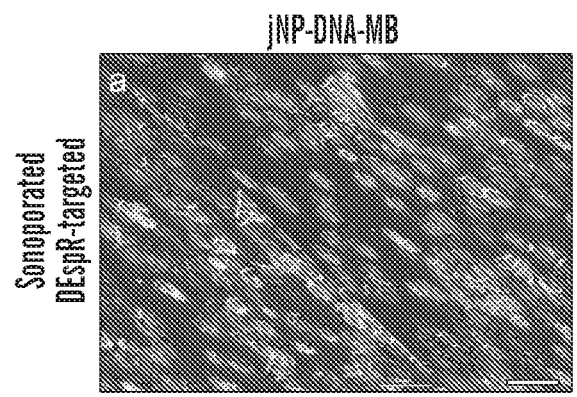
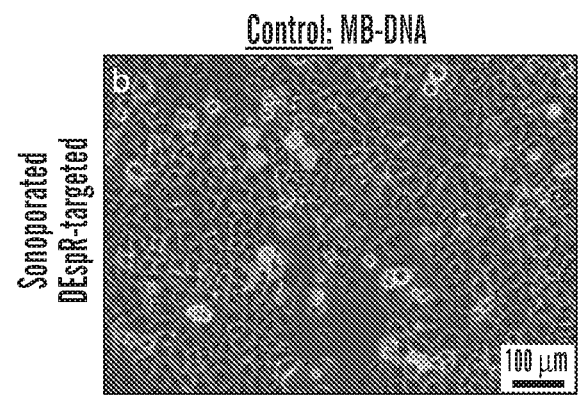
FIG. 4A  FIG. 4B
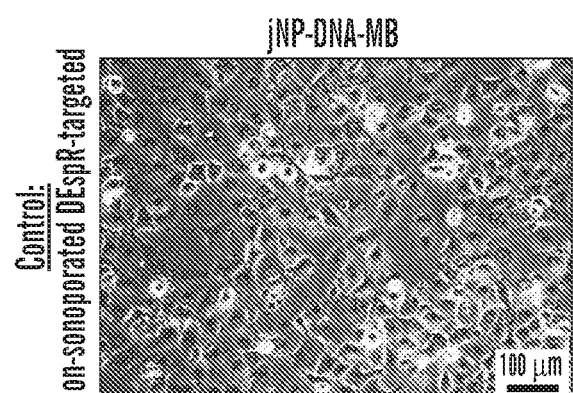
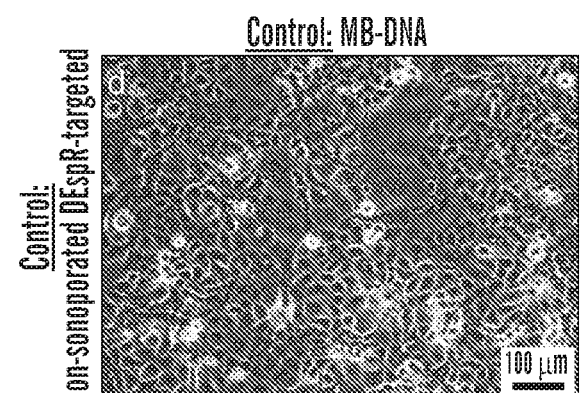
FIG. 4C  FIG. 4D

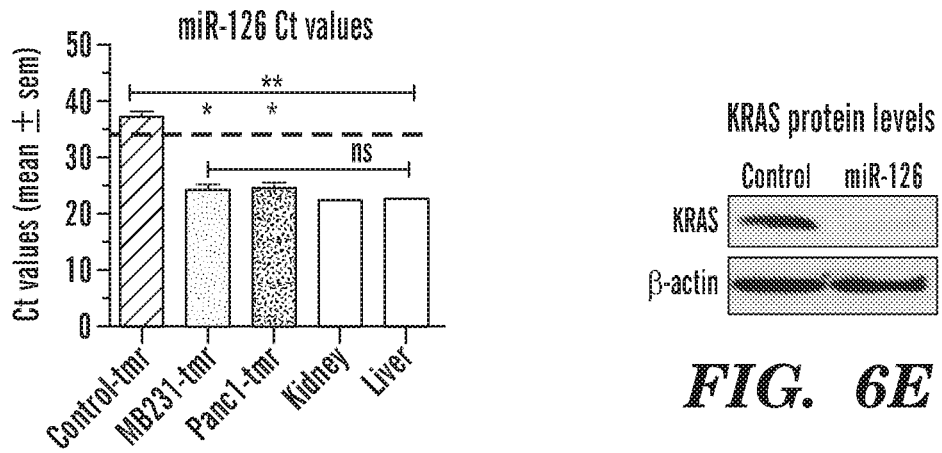
*FIG. 6D*
*FIG. 6E*
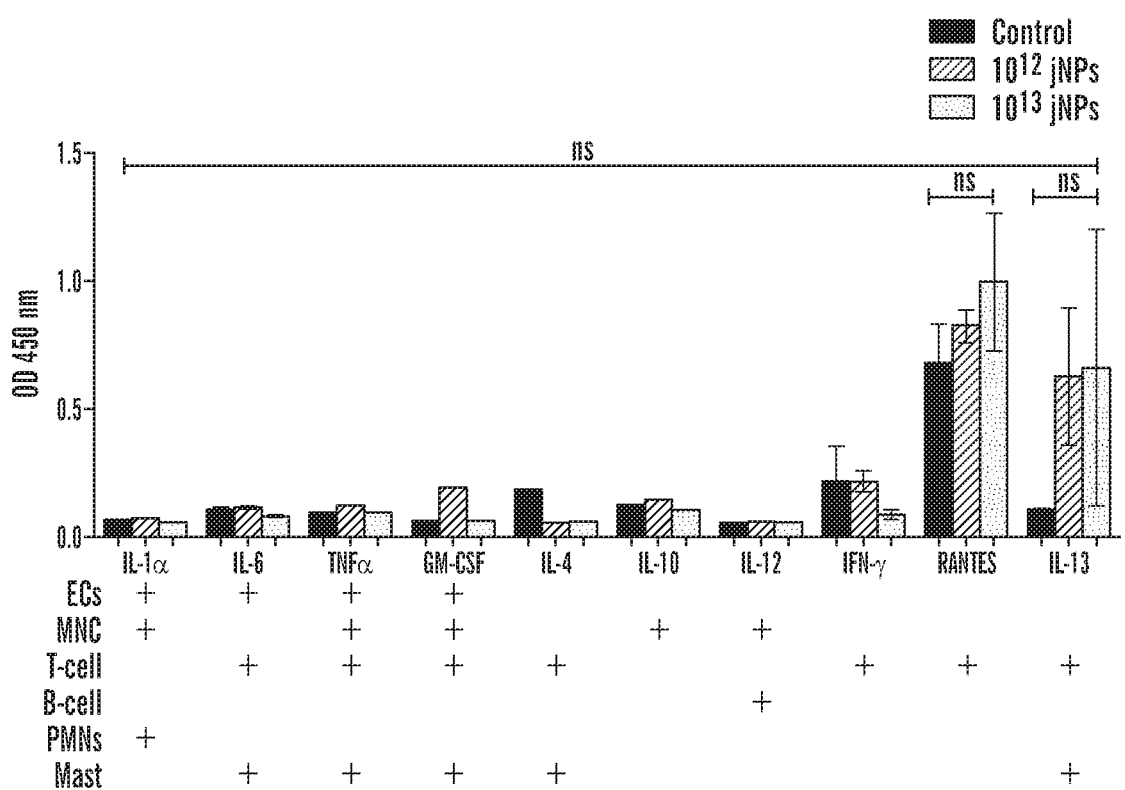
*FIG. 6F*

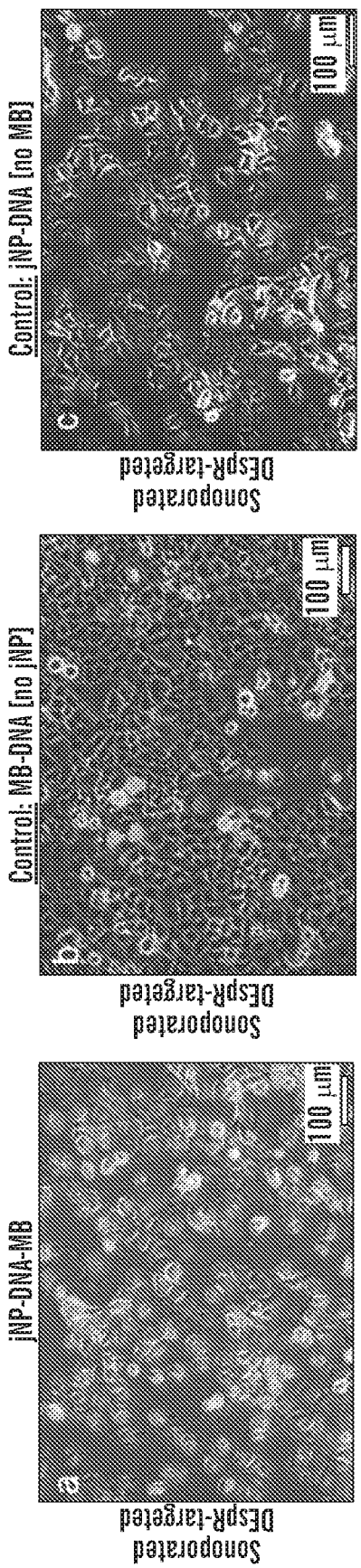
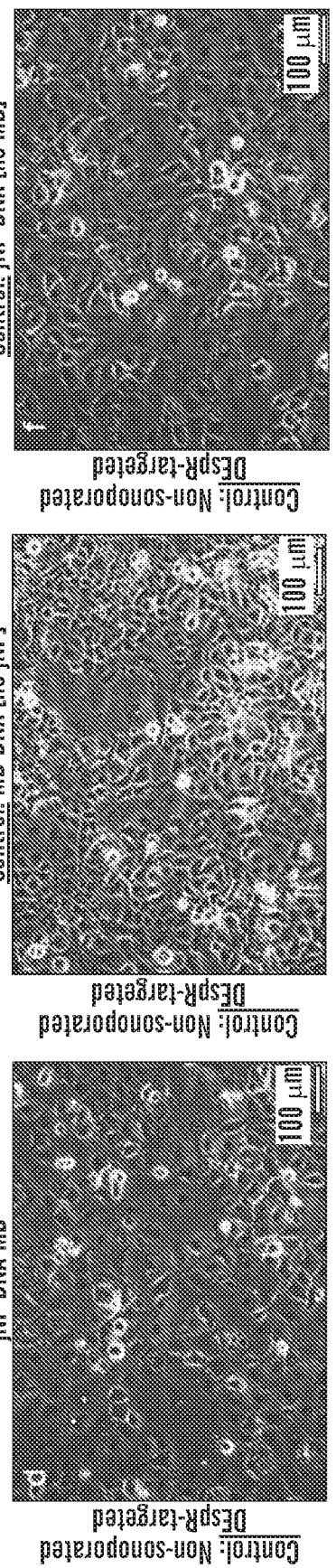
FIG. 17A, FIG. 17B, FIG. 17C, FIG. 17D, FIG. 17E, FIG. 17F

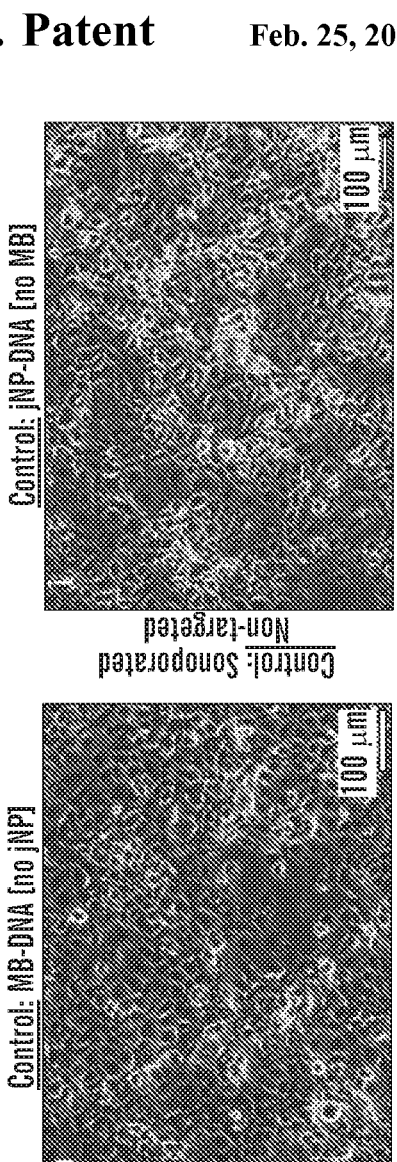
FIG. 17G
FIG. 17H
FIG. 17I
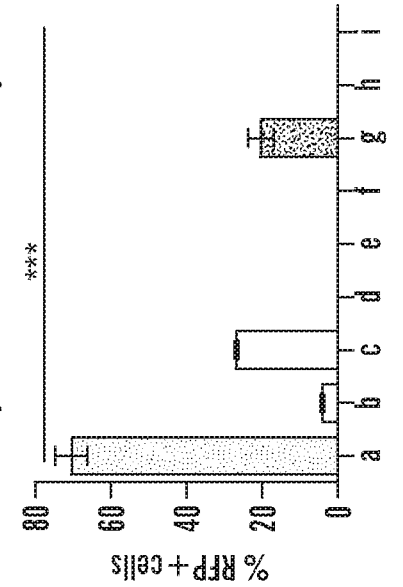
FIG. 17J

| Test construct | Symbol | Control | Symbol |
|---|---|---|---|
| Non-targeted jNP | | USPION | |
| | | USPION-PEG-NH2 | |
| | | USPION-PEG-NH2-PEI | |
| Non-targeted jNP-DNA | | EtBr-DNA | |
| | | EtBr | |
| | | DNA | |
| Non-targeted jNP-ssDNA-MB | | MB | |
| | | ssDNA | |
| | | Non-targeted jNP | |
| Targeted jNP-DNA-MB | | Non-targeted jNP-DNA-MB | |
| | | Targeted jNP | |
| | | MB | |
| | | Targeted MB-DNA | |
| | | MB-DNA | |
| | | Targeted MB | |
| | | Non-targeted MB | |
| Targeted jNP-miRNA-MB | | Targeted jNP-siRNA-MB | |

Legend: • Non-Targeting Ab  • Targeting Ab  • miRNA  • siRNA  • MicroMarker MB  • Target-ready MB

*FIG. 23*

THERANOSTIC COMPOSITIONS AND USES THEREOF

CROSS-REFERENCE TO RELATED APPLICATIONS

This Application is a 35 U.S.C. § 371 National Phase Entry Application of International Application No. PCT/US2016/018417 filed Feb. 18, 2016, which designates the U.S. and which claims benefit under 35 U.S.C. § 119(e) of the U.S. Provisional Application No. 62/118,817 filed Feb. 20, 2015, and of the U.S. Provisional Application No. 62/157,623 filed May 6, 2015, the contents of each of which are incorporated herein by reference in their entireties.

FIELD OF THE INVENTION

The field of the invention relates to theranostic compositions useful in both imaging and treatment of diseases, such as cancer.

BACKGROUND

A high unmet need persists for successful delivery of nucleic acid therapy (e.g., DNA, RNA) to address genetic and epigenetic heterogeneity, which underlie current cancer therapy failures. Multifunctional nanotechnologies are recognized as promising delivery platforms; however, key limitations in effective delivery of functionally intact nucleic acid payloads and/or in safety impede clinical translation of current nucleic acid nano-delivery systems.[1-4] Assuming tumor-specific targeting is achieved, efficacy of lipid and likely other nanoplatforms are dependent on endocytosis or macropinocytosis for intracellular delivery and remain inefficient due to limited (<2%) escape of nucleic acid-cargo from endosomes into the cytosol[2,5] and/or due to majority (>70%) of internalized RNA-cargo being exocytosed back to the extracellular space.[6] Moreover, even if delivered intact, DNA/RNA-payloads need to integrate into the cellular machinery for functional efficacy.[2] Moreover, efficient in vitro nano-delivery systems, such as self-assembled cationic PEI-polyplexes, manifest toxic effects arising from excess cationic material remaining after self-assembly and/or from release of high MW or branched-$PEI_{25kDa}$ as a result of disassembly in vivo.[4] Alternatively, sonoporation-induced cytosolic-delivery of nucleic acid therapies has been tested to bypass inefficiencies of endosomal uptake, but remains inefficient with current microbubble technologies and modifications.[7, 60] To overcome key limitations, rational nanoparticle designs must consider not only charge, hydrophilicity, shape, and size[8-13], but also the need to eliminate excess unincorporated materials, improve in vivo structural stability and prevent aggregation. Ideally, designs must also consider alternative endocytosis-independent mechanisms to deliver [DNA/RNA]-payloads,' modular multifunctionalities,[14] and inherent versatility to accommodate multiple targeting and payload moieties to address genetic/epigenetic heterogeneity in cancers, which to date, underlie current cancer therapy failures.

By virtue of their spatial separation of multifunctional components, thus eliminating confounding multi-component steric or chemical interactions, Janus nanoparticle designs have a unique potential to meet the foregoing criteria[14,15] However, this potential has yet to be realized with Janus NPs reported to date, which are typically larger than 100 nm, and were not designed to deliver nucleic acid therapies.[14-19] Alternatively, nano/micro-hybrids bring unexplored potential, however, while dual MRI-ultrasound imaging flexibility has been attained using "nano-in-micro" composites of iron oxide nanoparticles encapsulated within microbubbles[2,14] or within the microbubble shell,[20-22] these composite particles lack delivery functionality.

SUMMARY

Provided herein are methods and compositions that comprise dual functionality as a diagnostic reagent and a drug delivery agent (e.g., act as theranostic agents). The compositions described herein are particularly useful in delivering nucleic acid agents to address genetic/epigenetic heterogeneity in diseases, such as cancer, that underlie failure to respond to conventional treatment.

In one aspect, provided herein is a composition comprising: a microbubble with a Janus nanoparticle associated with the surface, wherein the Janus nanoparticle comprises an ultrasmall superparamagnetic iron oxide (USPIO) nanoparticle having a nucleic acid delivery face and a targeting face, and wherein the nucleic acid delivery face and the targeting face are distinct (e.g., spatially segregated) from one another.

In one embodiment of this aspect and all other aspects described herein, the Janus nanoparticle is less than 75 nm in size (e.g., 70, 65, 60, 55, 50, 45, 40, 35, 30, 25, 20, 15 nm or smaller).

In another embodiment of this aspect and all other aspects described herein, the superparamagnetic iron oxide nanoparticle is less than 20 nm in size (e.g., 19, 18, 17, 16, 15, 14, 13, 12, 11, 10, 9, 8, 7, 6, or 5 nm or smaller).

In another embodiment of this aspect and all other aspects described herein, the Janus nanoparticle is asymmetrically shaped.

In another embodiment of this aspect and all other aspects described herein, the Janus nanoparticle is avocado shaped.

In another embodiment of this aspect and all other aspects described herein, the targeting face is situated at the upper part of the avocado shaped nanoparticle, and the carrier face is situated at the round, bottom part of the avocado shaped nanoparticle.

In another embodiment of this aspect and all other aspects described herein, the targeting face comprises a targeting moiety selected from the group consisting of: a targeting peptide, a polyclonal antibody, a monoclonal antibody, an antibody binding fragment, a composite antibody, a recombinant antibody, a cell penetrating peptide and a matrix interacting peptide with e.g., multiple units attached to the mixed PEG brush to impart efficiency of binding of the jNP through multivalent targeting moiety. In another embodiment of this aspect and all other aspects described herein, the composition comprises a long half-life in the circulation due to the properties of the targeting moiety components, for example, IgG antibodies that have a long half-life in the circulation.

In another embodiment of this aspect and all other aspects described herein, the targeting moiety binds to a cell surface or cell matrix protein. In some embodiments, the targeting moiety will permit part or all of the composition to be internalized within the cell.

In another embodiment of this aspect and all other aspects described herein, the carrier face comprises a polymer.

In another embodiment of this aspect and all other aspects described herein, the polymer comprises a polyelectrolyte.

In another embodiment of this aspect and all other aspects described herein, the polyelectrolyte is a cationic polyelectrolyte or an anionic polyelectrolyte.

In another embodiment of this aspect and all other aspects described herein, the Janus nanoparticle comprises an iron oxide core with a PEG brush.

In another embodiment of this aspect and all other aspects described herein, the PEG brush is a mixed 3:1 short-long PEG brush.

In another embodiment of this aspect and all other aspects described herein, the moieties in the targeting and carrier faces are covalently coupled or tethered to the long PEG in the mixed PEG-brush.

In another embodiment of this aspect and all other aspects described herein, the iron oxide core is encapsulated within a polymer.

In another embodiment of this aspect and all other aspects described herein, the polymer-encapsulated iron oxide core further comprises a bioactive agent. In another embodiment, the polymer-encapsulated iron oxide core further encapsulates one or more bioactive agents.

In another embodiment of this aspect and all other aspects described herein, the composition further comprises a bioactive agent.

In another embodiment of this aspect and all other aspects described herein, the bioactive agent comprises a nucleic acid molecule.

In another embodiment of this aspect and all other aspects described herein, the nucleic acid molecule is sandwiched between the microbubble and the carrier face of the Janus nanoparticle.

In another embodiment of this aspect and all other aspects described herein, the composition is formulated for use as a magnetic resonance imaging (MRI) contrast agent.

In another embodiment of this aspect and all other aspects described herein, the MRI contrast agent comprises or exhibits a shorter magnetic resonance T2*-relaxivity.

Another aspect provided herein relates to a Janus nanoparticle comprising a superparamagnetic iron oxide nanoparticle having a nucleic acid delivery face and a targeting face, and wherein the nucleic acid delivery face and the targeting face are distinct from one another.

In one embodiment of this aspect and all other aspects described herein, the Janus nanoparticle is less than 75 nm in size (e.g., 70, 65, 60, 55, 50, 45, 40, 35, 30, 25, 20, 15 nm or smaller).

In another embodiment of this aspect and all other aspects described herein, the superparamagnetic iron oxide nanoparticle is less than 20 nm in size (e.g., 19, 18, 17, 16, 15, 14, 13, 12, 11, 10, 9, 8, 7, 6, or 5 nm or smaller). In another embodiment of this aspect and all other aspects described herein, the Janus nanoparticle is about 10-40 nm or about 20-30 nm in size as measured using cryo-electron microscopy or about 10-60 nm or about 40-60 nm (e.g., about 50 nm) in size as measured by dynamic light scattering (DLS).

In another embodiment of this aspect and all other aspects described herein, the Janus nanoparticle is asymmetrically shaped.

In another embodiment of this aspect and all other aspects described herein, the Janus nanoparticle is avocado shaped.

In another embodiment of this aspect and all other aspects described herein, the targeting face is situated at the upper part of the avocado shaped nanoparticle, and the carrier face is situated at the round, bottom part of the avocado shaped nanoparticle.

In another embodiment of this aspect and all other aspects described herein, the Janus nanoparticle is (i) suitable for in vivo administration for use e.g., in non-invasive in vivo contrast-enhanced magnetic resonance imaging (MRI), and/or (ii) suitable for in vitro self-assembly of a heteroplex comprised of the Janus nanoparticle with nucleic acid therapies (e.g., miRNA, DNA, and/or siRNA) and amphoteric microbubbles for in vivo contrast-enhanced ultrasound molecular imaging and/or (iii) suitable for in vivo antibody-targeted delivery of nucleic acid therapy by sonoporation.

In another embodiment of this aspect and all other aspects described herein, the targeting face comprises a targeting moiety selected from the group consisting of: a targeting peptide, a polyclonal antibody, a monoclonal antibody, an antibody binding fragment, a composite antibody, a recombinant antibody, a cell penetrating peptide and a matrix interacting peptide.

In another embodiment of this aspect and all other aspects described herein, the targeting moiety binds to a cell surface or cell matrix protein. In some embodiments, the targeting moiety will permit part or all of the composition to be internalized within the cell.

In another embodiment of this aspect and all other aspects described herein, the targeting moiety is tethered directly to an amine group on the PEG brush, or via a linear or branched linker or cleavable spacer that can be linked by an enzyme.

In another embodiment of this aspect and all other aspects described herein, targeting is enhanced due to polyvalency of targeting moieties and non-interference by payloads due to the spatial segregation of the targeting face and the carrier face.

In another embodiment of this aspect and all other aspects described herein, the carrier face comprises a polymer.

In another embodiment of this aspect and all other aspects described herein, the polymer comprises a polyelectrolyte.

In another embodiment of this aspect and all other aspects described herein, the polyelectrolyte comprises polyethyleneimine (PEI).

In another embodiment of this aspect and all other aspects described herein, the polyelectrolyte is a cationic polyelectrolyte or peptide or an anionic polyelectrolyte or peptide.

In another embodiment of this aspect and all other aspects described herein, the carrier face comprises a carrier moiety tethered directly to an amine group on the PEG brush, or via a linear or branched linker or cleavable spacer that can be linked by an enzyme.

In another embodiment of this aspect and all other aspects described herein, the carrier face forms a polyelectrostatic bridge with cognate opposing-charged payloads, such as cationic polyelectrolyte to negatively charged nucleic acids (e.g., DNAs, oligonucleotides, miRNAs, miRNA-mimics, anti-miRNAs, siRNAs etc.), peptides, or drugs (e.g., small molecule drugs).

In another embodiment of this aspect and all other aspects described herein, the carrying and delivery efficiency are enhanced by the polyvalency and spatial segregation of the polyelectrostatic bridge of the carrier face.

In another embodiment of this aspect and all other aspects described herein, the Janus nanoparticle comprises an iron oxide core with a PEG brush.

In another embodiment of this aspect and all other aspects described herein, the PEG brush is a mixed 3:1 short-long PEG brush.

In another embodiment of this aspect and all other aspects described herein, the moieties in the targeting and carrier faces are covalently coupled or tethered to the long PEG in the mixed PEG-brush.

In another embodiment of this aspect and all other aspects described herein, the iron oxide core is encapsulated within a polymer.

In another embodiment of this aspect and all other aspects described herein, the polymer-encapsulated iron oxide core further comprises a bioactive agent, such as a small molecule drug or a chemotherapeutic. In another embodiment of this aspect and all other aspects described herein, the bioactive agent comprises a non-deliverable drug, for example, a drug that is hydrophobic, cytotoxic, or otherwise incompatible for delivery.

In another embodiment of this aspect and all other aspects described herein, the jNP with a polymer encapsulated iron oxide core and further comprising a bioactive agent, such as a small molecule drug or chemotherapeutic, facilitates the delivery of the bioactive agent (e.g., a pharmacologically incompatible bioactive agent).

In another embodiment of this aspect and all other aspects described herein, wherein the iron oxide core is about 5-15 nm and covalently coupled to the targeting moiety(ies) on the targeting face and covalently coupled to the polyelectrolyte moieties on the carrier face.

In another embodiment of this aspect and all other aspects described herein, the Janus nanoparticle enhances magnetic resonance (MR) contrast enhancement compared with non-Janus nanoparticle iron oxide nanoparticles due to changes in MR properties, such as relaxivity.

In another embodiment of this aspect and all other aspects described herein, MR-imaging is performed on a tumor and the MR-imaging of such tumors exhibits enhanced detection of tumor angiogenesis, extracellular matrix changes, edema, ischemia, inflammation, abnormal vasculature, invasiveness, metastasis and microtumors.

In another embodiment of this aspect and all other aspects described herein, the MR-imaging exhibits enhanced detection of features that distinguishes abnormal from normal, such as abnormal organ vascular patterns, normal and abnormal vascular integrity, normal and abnormal organ structures, angiogenic response, vascular leakiness, perivascular fibrosis, organ parenchyma, cellularity, extracellular matrix composition, fibrosis, among others.

In another embodiment of this aspect and all other aspects described herein, the Janus nanoparticle (jNP) can bind to DNA-coated or nucleic acid-coated microbubbles forming a heteroplex such as, a nNP[nucleic acid]microbubble heteroplex that performs better in ultrasound mediated molecular imaging and delivery of nucleic acid by sonoporation compared to all current non-[20-50 nm]jNP-mediated methods of sonoporation.

Another aspect described herein relates to a composition for use as an MRI contrast agent comprising: a Janus nanoparticle, which comprises a superparamagnetic iron oxide nanoparticle having a nucleic acid delivery face and a targeting face, and wherein the nucleic acid delivery face and the targeting face are distinct from one another.

In one embodiment of this aspect and all other aspects provided herein, the MRI contrast agent is a negative contrast agent.

In another embodiment of this aspect and all other aspects provided herein, the composition is for use in detection and/or monitoring of electron paramagnetic resonance (EPR) imaging.

Another aspect provided herein relates to a method for imaging, the method comprising: (a) administering to a subject an MRI contrast agent comprising: a Janus nanoparticle, which comprises a superparamagnetic iron oxide nanoparticle having a nucleic acid delivery face and a targeting face, and wherein the nucleic acid delivery face and the targeting face are distinct from one another, and (b) performing an MRI on the subject.

In another embodiment of this aspect and all other aspects provided herein, the MRI comprises electron paramagnetic resonance (EPR) imaging.

Another aspect provided herein relates to a composition for use as an MRI contrast agent for target-specific imaging, the composition comprising: a Janus nanoparticle, which comprises a superparamagnetic iron oxide nanoparticle having a nucleic acid delivery face and a targeting face, and wherein the nucleic acid delivery face and the targeting face are distinct from one another, and wherein the targeting face comprises an antibody directed to a target to be imaged.

In one embodiment of this aspect and all other aspects provided herein, the target to be imaged is a tumor.

Another aspect provided herein relates to a method for target-specific imaging, the method comprising: (a) administering to a subject an MRI contrast agent comprising: a Janus nanoparticle, which comprises a superparamagnetic iron oxide nanoparticle having a nucleic acid delivery face and a targeting face, wherein the nucleic acid delivery face and the targeting face are distinct from one another, and wherein the targeting face comprises an antibody directed to a target to be imaged, and (b) performing an MRI on the subject.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 1A, Schematic diagram of directional layer-by-layer method to prepare jNPs. Layers are: 1: cationic polymer, PEI, adsorbed onto a mica sheet; 2: glutaraldehyde, conjugated to amines in the PEI layer; 3: $Fe_3O_4$~10 nm USPION with mixed partially amine-terminated PEG2K/3.4K brush (~5-8 nm) conjugated to glutaraldehyde layer; 4: maleimide layer from conversion of free amines on USPION core by N-hydroxy-succinimide maleimide (NHS-maleimide); 5: targeting antibodies (Ab) conjugated to layers-4; 6: asymmetrically functionalized jNPs released from mica sheet with salt. FIG. 1B, Representative cryo-TEM images of jNPs from two independent jNP preparations showing an asymmetric, avocado-like ~22-32 nm particle with an electro-dense USPION core closer to the PEI cationic carrier-face, and targeting antibodies (~12 nm) comprising the opposing targeting-face. Scale bar=20 nm. FIG. 1C, Representative atomic force microscopy (AFM) multi-parameter images (amplitude, topography, and phase) of individual jNPs. Scale bar=50 nm.

FIG. 2A, Differential zeta-potential levels of partial jNP layered-composition stages with ultrasmall 10-nm SPION cores: SPION-PEG, SPION-PEG-NH2, SPION-PEG-NH2-PEI, and jNPS (n=3). ANOVA * $p<0.05$; ** $p<0.01$. FIG. 2B, Fluorescence intensity levels, documenting conjugation of AF594-labeled antibodies (Ab) as final layer (jNP) and targeting-face of jNPs compared to ultrasmall SPION-PEG-NH2-PEI and water control (n=3). ANOVA * $p<0.01$. FIG. 2C, Representative frequency plot of hydrodynamic diameters (nm) obtained via dynamic light scattering (DLS) at time-0. FIG. 2D, Representative serum-stability time-course plot of hydrodynamic diameters (nm) of jNPs from 0-120 hours (hr) in 85% serum. FIG. 2E, Representative AFM amplitude and topography images taken of jNPs at t−1 and t−24 hr in 85% serum. Scale bar=50 nm. FIG. 2F, Ethidium bromide (EtBr) dye exclusion assay for different amounts of DNA (300, 100, and 50 ng RFP-minigene plasmid DNA) exposed to increasing amounts of jNPs (# of jNPs×$10^{10}$) for 10 min incubation. Level of free DNA, unbound or unprotected by jNPs, is indicated by level of EtBr fluorescence intensity (arbitrary units, AU) emitted from EtBr upon intercalation into free DNA. Fluorescence [Ex. 260/Em.590 nm] at 10 min done in duplicate; highest jNP point in triplicate. Agarose gel analysis of EtBr fluorescence after intercalation into 'free' RFP plasmid 4.7 kb DNA. Lanes 1-4, increasing [0, 0.2, 0.6, 1.8×$10^{10}$] jNPs added to 100 ng RFP-DNA for 10 min. MW, bands from 10, 8, 6, 5, 4, 3, and 2 kb DNA markers.

FIG. 3A, Schematic diagram of self-assembly of targeted and non-targeted jNP-MBs. Multiple types of nucleic acids can be added to the MB as the payload. Coverage of jNPs on MB can be tuned. FIG. 3B, Representative FACS analysis of non-targeted jNPs with AF568-labeled IgG and AF488-labeled single strand 50-nt oligoDNA. Left panel shows control non-fluorescent MBs (Q4, MB). When compared to assembled jNP-MBs (right panel), double fluorescent jNP-MBs with projected density of ~0.05% jNP-coverage of MBs (Q2) are distinguished from single-fluorescent MB-DNA (Q3), and non-fluorescent MBs (Q4, MB). FIG. 3C, Representative FACS analysis of jNP-MB assembly. Panels 1-3: Control, non-fluorescent microbubbles (MB), compared with fluorescent targeted jNP-MBs with 1% and 50% coverage of MB surface by AF594-labeled monoclonal antibody against DEspR. Stacked bar graph of dose-response effects of increasing % jNP-coverage of MBs on %—fluorescent and % non-fluorescent (black) MBs, * $p<0.0001$ chi-square analysis. FIG. 3D, Representative baseline FACS analysis of controls 1-3: microbubbles, targeted AF594-labeled jNPs, and Panc1 tumor cells, respectively (Panels 1,2,3). Comparative FACS analysis of Panc1 tumors cells targeted by, and bound with jNP-MBs at 1:1 and 1:5 cell:jNP-MB ratio using jNP-MBs with 10% coverage. The percent (%) fluorescent units of total fluorescent counts are indicated in respective regions of interest. Free jNP-MBs are demarcated (53.2% and 75.2%) and not included in the ±fluorescent cell counts. Stacked bar graph of FACS data shows % fluorescent and % non-fluorescent (black) Panc1 cells from total cell counts at different cell:jNP-MB ratios, *$p<0.0001$ chi-square analysis. FIG. 3E, Epi-fluorescence microscopy analysis of Panc1 tumor cells with attached fluorescently-labeled targeted jNP-MBs (~2-3 μm diameter MBs) compared with control non-targeted jNP-MBs. bar, 10 μm. Black/white stacked bar graph depicts % MB-positive cells when exposed to targeted jNP-mBs compared with control non-targeted jNP-MBs. ■, MB+ cells; □ MB(−) cells; chi-square analysis $p<0.0001$; n=80 (targeted jNP-MBs); n=30 (non-targeted jNP-MBs). Bar graph depicts number of jNP-MBs per cell among MB+ cells comparing targeted jNP-MBs and non-targeted jNP-MBs. ***Mann Whitney test: p=0.0006; targeted jNP-MBs n=14; non-targeted jNP-MBs (white) n=6 cells.

FIGS. 4A-4H Representative photomicroscopy images using identical exposures comparing in vitro fluorescence resulting from delivery of functionally intact reporter minigene-DNA (red fluorescent protein, RFP) to Panc1 cells 48-hours after sonoporation. FIG. 4A, Panc1 cells sonoporated with DEspR-targeted jNP[DNA]MB-heteroplexes exhibit RFP-positive expression. FIG. 4B, Less RFP-positive expression in Panc1 cells sonoporated with control DEspR-targeted non-jNP[DNA]MBs. Anti-DEspR mAb linked to MBs by biotin-streptavidin. FIG. 4C, Control non-sonoporated Panc1 cells with DEspR-targeted jNP[DNA]MBs. FIG. 4D, Control non-sonoporated non-jNP [DNA]MBs. FIG. 4E, Panc1 cells sonoporated with control non-targeted (isotype)-jNP[DNA]MB, and FIG. 4F, control sonoporated non-targeted (isotype) non jNP[DNA]MBs. Bar=100 μm; identical experimental conditions: ~1:5 cell:MB ratio, DNA-MB ratio (30 μgDNA/$10^8$ MBs); 10% jNP-coverage used for DEspR-targeted and isotype-non-targeted jNP[DNA]MB-heteroplexes. FIG. 4G, high magnification image of RFP+ fluorescent Panc1 tumor cells ascertaining cell-specific expression. FIG. 4H, Bar graph of % RFP-positive cells in randomly selected sections (n=3-19) from three independent experiments (4 sonoporation sites, 1 control site per experiment) of study groups represented in panels a-f. Kruskall Wallis non-parametric ANOVA $p<0.0001$; panel a: # n=19; b: n=12; c: n=3, d: n=4; e: n=12; f: n=3. Post-hoc test: Dunn's multiple comparisons test, *, $p<0.05$; ***, $P<0.0001$; a vs. c: also $p<0.0001$.

FIG. 5A, Gradient-echo signal intensity versus echo time (TE, ms), from 10-100 ms, for jNP and precursor-USPION phantoms, both at 5×$10^{10}$/ml in 1% agar, and control blank 1% agar phantom. Each curve was normalized so that peak signal at TE=4 ms is equal to 1. jNPs exhibited shorter T2*-relaxivity values (mean±sd: 35.7±1.2 ms) compared with precursor-USPIONs (57.9±2.2 ms) and control blanks (82.0±5.1 ms)$p<0.001$, two-way ANOVA repeated measures. FIG. 5B, Representative susceptibility weighted intensity (SWI) magnetic resonance (MR)-images of Panc1 xenograft tumors in nude rats. Negative control: tumor with no jNPs; Positive control: tumor injected intratumorally with 50 μl of $10^{12}$/ml non-targeted isotype-jNPs; Right panel: tumor with intravenous (IV)-infused non-targeted jNPs imaged at t−24 hr consistent with tumor-selective EPR effects. Arrows indicate jNP localization of low-intensity regions, indicating increased iron content on SWI sequence; bar=1 cm. FIG. 5C, Contrast-enhanced ultrasound images: overlay of B-mode (grey to black) and contrast-enhanced images (pseudo-colored) in spontaneous rat mammary tumors comparing control DEspR-targeted non-jNP/MBs (Targeted Control-MBs) and DEspR-targeted jNP[DNA]MB-heteroplexes (Targeted jNP[DNA]MBs) at pre-destruct time point (t20: Pre-destruct), and pre- and post-destruct (t21:Post-destruct) time points. Regions of interest (ROI) for quantitation: intratumoral microvessels, extra-tumoral 'feeder vessels' at tumor base. (See FIG. 10 for schematic diagram). FIG. 5D, Representative time-intensity curves of contrast intensity signals in designated ROI at pre-destruct (PRE) and post-destruct (POST) time points, comparing extra-tumoral feeder vessels and intratumoral microvessels, and comparing Targeted jNP[DNA]MBs and Targeted Control-MBs. Timepoint of high-power ultrasound MB-destruct sequence (dashed line) demarcating pre- and post-destruct contrast intensity signals. FIG. 5E, Quantitative analysis of peak contrast intensity signals (CIS) comparing DEspR-targeted jNP[DNA]MB heteroplexes (jNP) and control (con) non jNP DEspR-targeted microbubbles (con) in both ROIs: extratumoral feeder vessels (fv) and intratumoral microvessels (my) at two timepoints: t20 and t30 min. One-way ANOVA $p<0.0001$, ***, Tukey's multiple pairwise comparison $p<0.0001$, n=8 groups, representing 10 random measures of peak CIS values in each ROI (extratumoral and intratumoral) at two time points (t20, t30) taken from 3 independent rat experiments using spontaneous mammary tumor rat model.

FIGS. 6A-6F In vivo analysis of jNP-DNA-MB delivery functionality and safety profile. FIG. 6A, Side-by-side IVIS image of RFP-fluorescence in spontaneous mammary tumors from a control mock-sonoporated rat with negative fluorescence (rat on left) and from a rat sonoporated with targeted jNP-DNA-MBs obtained two days after sonoporation (rat on right); IVIS image of control targeted MB-DNA (FIG. 11A). Fluorescence scale bar is in $10^9$ units, in contrast to scale bar in $10^3$ units for current technology MBs-DNA (FIG. 11B). Stacked bar graph of fold-increase in RFP fluorescence 48-hours (t–48 hrs) after sonoporation from baseline (white) comparing control targeted MBs-DNA (n=2) with test targeted jNP-DNA-MBs (n=2). FIG. 6B, Plot of melting temperatures (Tm) derived from real-time qRT-PCR analyses of miRNA-126 levels in rat xenograft tumors 48-hrs after sonoporation with targeted jNP-MBs: at $10^8$ MBs, $10^{12}$ jNPs, 27 ug ds miRNA-126-mimic compared to negative control tumors (non-sonoporated, non-infused). (black, control-T, negative control tumors (n=4); MB 231-T, MDA-MB-231 CSC-derived breast cancer subQ tumors (n=4); Panc1-T, Panc1-CSC-derived subQ tumors (n=6). $T_m$ plots from different samples are identical and consistent with expected Tm for miRNA-126 ~75.4° C. FIG. 6C, Real-time qRT-PCR cycle threshold (Ct) plots of miRNA-126 comparing sonoporated breast and pancreatic xenograft tumors and control tumors; low Ct indicate high miRNA-126 levels. FIG. 6D, Bar graph of Ct values, means±sem; dashed line for threshold Ct value for negative expression, ie Ct>34; **, $p<0.008$ Kruskall Wallis ANOVA on ranks; *, $p<0.05$, multiple pairwise comparison of control tumor (tmr) vs other tumors; ns, not significant Kruskall Wallis ANOVA on ranks analyzing normal liver (n=4), kidney (n=4), MB231-tmr, and Panc1-tmr. FIG. 6E, Representative Western blot analysis of miRNA-126 target KRAS protein level 48-hr after delivery of miRNA-126 by sonoporation; β-actin protein levels serve as internal control. FIG. 6F, ELISA levels of key cytokines/chemokines (IL-1α, IL-6, IL-4, IL-10, IL-12, IL-13: interleukins; TNFα: tumor necrosis factor alpha, GM-CSF: granulocyte macrophage colony stimulating factor, IFN-γ: interferon gamma, RANTES: Regulated on Activation, Normal T Cell Expressed and Secreted or CCL5) produced by cells which are exposed to non-targeted jNPs in the circulation such as ECs, endothelial cells, MNC, monocytes, T- and B-cell leukocytes, PMNs, neutrophils or polymorphonuclear cells; Mast, complement-activated mast cells. Statistics performed: two-way (jNP-dose×cytokine levels) ANOVA (ns, not significant); cytokine-specific one way ANOVA (ns, not significant); n=triplicates/rat×2 rats/group×3 groups: rats infused with 1) $10^{12}$ non-targeted jNPs in stroke prone rats; 2) $10^{13}$ non-targeted jNPs in normal rats, and 3) negative control age-, sex-, genotype-matched rats infused with vehicle saline.

FIG. 7A, AFM amplitude, topography and phase images show the asymmetric avocado-like morphology of the jNP. The shortest radius, as calculated from the center of the iron oxide core to the closest edge, is 11.24 nm. All scaling of AFM images must account for the 20 nm radius tip. FIG. 7B, AFM image of deposited lambda-phage DNA strand shows typical Y-shaped DNA-strand with jNPs attached to DNA-strand. The phase diagram (far right) highlights the difference of the iron oxide cores and the DNA strand from the mica surface.

FIG. 8A, Ethidium bromide (EtBr) dye displacement assay. Increasing amount of jNPs can displace EtBr intercalated into DNA base pairs (bp). Because EtBr fluoresces only when intercalated into DNA, loss of fluorescence from baseline indicates displacement of EtBr from pre-mixed DNA-bp:EtBr at a 4:1 ratio. FIG. 8B, Representative FACS image of side scatter area (SSC-a) detects increased granularity imparted by jNPs to MBs upon assembly of jNP[DNA]MB-heteroplexes. Y-axis, side scatter-area (SSC-a), corresponds to granularity; X-axis, forward scatter area, corresponds to size. Increased granularity is detected in jNP[DNA]MB-complexes with increased jNP-coverage of MBs: 50% (~5×$10^4$/MB) vs 1% ($10^3$ jNPs/MB) coverage of [DNA]MBs. FIG. 8C, FACS analysis of different MB stocks (<6 hrs from suspension) with "bead marders" (left); equidistant 15-micron size marked by dash line.

FIG. 11A, pre-infusion baseline with zero pseudocolor-green contrast intensity signals (CIS). FIG. 11B, bolus infusion associated with enhanced CIS; FIG. 11C, plot of CIS along time (x-axis), and contrast intensity signals (y-axis) with peak CIS at around 60-65 units. FIG. 11D, Contrast-enhanced imaging detects positive DEspR-targeted molecular imaging at the base of the mammary tumor corresponding to tumor feeder vessels, prior to operator-triggered destruction of microbubbles, or pre-destruct. FIG. 11E, Image at identical settings after sequence-destruction of microbubbles, or post-destruct, indicating contrast derived from attached MBs present at specified time point. FIG. 11F, Scatter plot of CIS showing peak CIS from attached MBs in the region of interest (ROI) for feeder vessels (encircled), destruction sequence marked by the red line/arrow, followed by post-destruction analysis showing a drop in CIS, which indicates destruction (bursting) of attached receptor-targeted microbubbles with subsequent elimination of contrast-enhancement by blood flow.

FIG. 15A, Comparative analysis of the terminal complement complex, Sc5b-9 levels (ng/ml) shows non-elevation, hence no complement activation, when using $10^{10}$ to $10^{13}$ jNPs/ml plasma compared with normal human plasma. Differences in means (n=6 from 2 independent jNP preparations) are not significant, Kruskall-Wallis ANOVA, followed by Dunns all pairs multiple comparisons test. Testing spans the range of jNPs/ml ($\Leftrightarrow$) used in vivo for DNA and miRNA-126 delivery, MRI and safety studies: $10^{12}$ jNPs/rat dose ~$5\times10^{11}$ jNPs/ml plasma; $10^{13}$ jNPs/rat dose ~$5\times10^{12}$ jNPs/plasma. Normal plasma (0 jNPs/ml) level=428.1±86. FIG. 15B, Standard curve for Sc5b-9 complex as per manufacturer's specifications (Quidel™, MicroVue SC5b 9 Plus Enzyme Immunoassay). All measurements were done in appropriate dilutions to obtain values within the linear range of the standard curve.

FIG. 16A, Expression levels of red fluorescent protein (RFP) (red fluorescent-positive cells) in Panc1 tumor cells sonoporated using DEspR-targeted jNP[DNA]MBs. FIG. 16B, Expression levels of RFP-positive expression sonoporated using non jNP control DNA-MBs wherein the antibody is coupled by avidin-biotin. FIG. 16C, RFP expression levels in Panc1 tumor cells of CD44-targeted jNPs. FIG. 16D, quantitative analysis reveals statistically significant enhancement of DNA-delivery compared with non-jNP DNA-MBs. ***, P<0.0001, One way ANOVA with Tukey's multiple comparison testing. Identical numbers of jNPs ($10^{12}$ jNPs/$10^8$ MBs), amounts of DNA (30 µg/10 ml), MBs ($10^8$/10 ml), and % confluence of Panc1 tumor cells were used. Sonoporation was performed using 0.153 MPa mechanical index after 45 minutes of incubation with constant rotation, and all unbound MBs removed by media change. These data indicate that covalent layering methodology facilitates modular targeting: jNPs can be targeted using different antibodies to target different cell surface receptors, for example, DEspR (dual endothelin1/VEGFsp receptor), CD44 (receptor for hyaluronic acid), both present on cancer cells.

FIGS. 17A-17L Representative epi-fluorescent microscopy images showing best image with in vitro fluorescence from expression of delivered reporter minigene-DNA (red fluorescent protein, RFP) to Panc1 cells 48-hours after sonoporation. FIG. 17A, Panc1 cells sonoporated with test-construct: targeted jNP-DNA-MBs exhibit RFP-positive expression. FIG. 17B, Control-1: Panc1 cells sonoporated with targeted MBs-DNA. FIG. 17C, Control-2: Panc1 cells sonoporated with DEspR targeted jNP-DNA (no MBs). FIG. 17D, Control-3: non-sonoporated Panc1 cells with DEspR-targeted jNP-DNA-MBs. FIG. 17E, Control-4: non-sonoporated Panc1 cells with DEspR-targeted MB-DNA (no jNP). FIG. 17F, Control-5: non-sonoporated Panc1 cells with DEspR-targeted jNP-DNA (no MBs). FIG. 17G, Control-6: Panc1 cells sonoporated with non-targeted (isotype IgG) jNP-DNA-MBs. FIG. 17H, Control-7: Panc1 cells sonoporated with non-targeted (isotype) MBs-DNA. FIG. 17I, Control-8: Panc1 cells sonoporated with non-targeted (isotype) jNP-DNA. FIG. 17J, Kruskall Wallis non-parametric ANOVA P<0.0001 of 9 study groups represented in panel a: n=16, b: n=12, c: n=6, d: n=3,e: n=4, f: n=4, g: n=12, h: n=3, i: n=3, photomicroscopy images (0.54 mm²) of fluorescent areas, if any. Post-hoc test: Dunn's multiple comparisons test for all pair-wise comparison to panel-a, P<0.05; bar=100 µm, panels 17A-17I. Taken together, these data indicate that jNP-DNA can deliver reporter function DNA via internalization of jNP-DNA as a function of the targeting moiety through receptor internalization. In this example, DEspR is internalized upon engagement with its antibody. FIG. 17K, Relative efficacy of in vitro DNA delivery by jNP-MBs compared with current technology cationic microbubbles (CMBs) reported. Parameters for comparison: peak % cell transfection, and peak % cell viability. FIG. 17L, Comparison of DNA and MB doses used per ml media in in vitro transfection experiments.

FIG. 22A, Average photons per second per area $cm^2$ per solid angle of one steradian (sr) in jNP-MBs (n=4 tumors, with 2 measured at 24- and 48 hrs after sonoporation) compared with published CMB reports of reported CMBs*: targeted: CMB-3, Zhou et al. (2015) *Theranostics* 4(4):399-417; CMB-4, Xie et al. (2012) *JACC Cardiovasc Imaging* 5:1253-1262; non-targeted: CMB-5: Panje et al. (2012) *Theranostics* 2:1078-1091; CMB-6: Sun et al. (2014) *J Control Release* 182:111-120; CMB-7: Wang et al. (2012) *Radiology* 264:721-732. All used IVIS imaging of fluorescence or bioluminiscence. FIG. 22B, Bar graph of amount of DNA loaded onto MBs in picogram (pg), and the mechanical index (MI, in megapasals (MPa) used for in vivo sonoporation or ultrasound-mediated DNA delivery. FIG. 22C, Bar graph of dose of DNA and microbubbles (MB) used per gram body weight. jNP-MBs were tested in rat tumor model; CMBs were tested in mouse models.

FIG. 23 Schematics of test and corresponding control constructs. Additional controls comprised of: different % coverage of MBs by jNPs (0.05%, 1%, 10%, 50%), sonoporation.

DETAILED DESCRIPTION

Figure 1A:
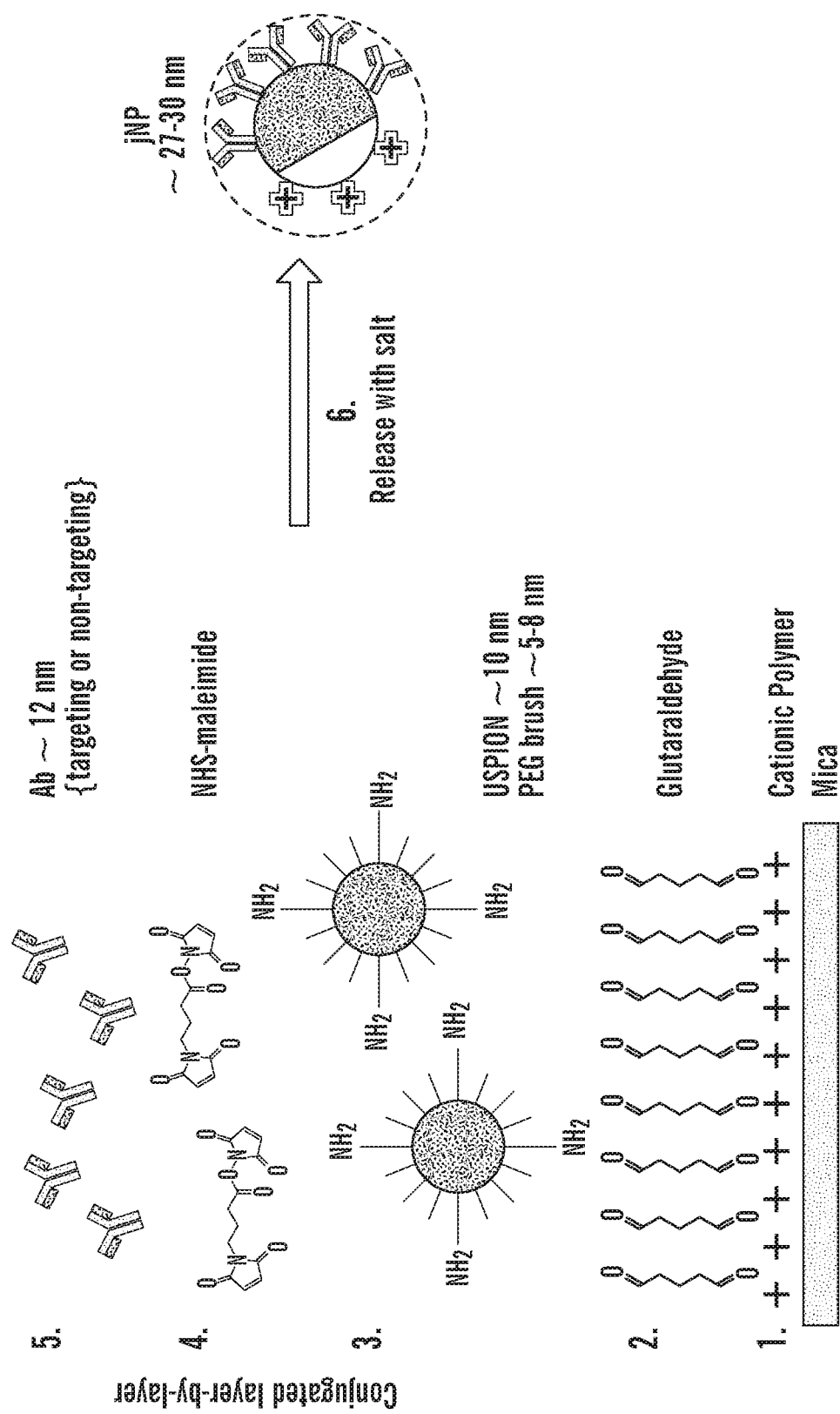
FIGS. 1A-1C Conjugated layer-by-layer preparation and cryo-TEM/AFM imaging of Janus nanoparticles (jNPs).

Provided herein are theranostic compositions comprising a Janus nanoparticle-coated microbubble that are useful for imaging (e.g., MRI, or ultrasound) and for delivering a therapeutic or bioactive agent (e.g., nucleic acid(s), drugs, etc).

Definitions

As used herein, the terms "functionalization", or "functionalized" are used to describe modifications to an iron oxide particle and can encompass, for example attaching a polymer, a linker, a particle, a targeting moiety, a chemical side group, a ligand, or any combination of these. Functionalization also encompasses attaching, for example a particle to a linker molecule on the surface of the cell As used herein, "a" or "an" means at least one, unless clearly indicated otherwise. As used herein, to "prevent" or "protect against" a condition or disease means to hinder, reduce or delay the onset or progression of the condition or disease.

The term "statistically significant" or "significantly" refers to statistical significance and generally means two standard deviations (2SD) or more above or below normal or a reference. The term refers to statistical evidence that there is a difference. It is defined as the probability of making a decision to reject the null hypothesis when the null hypothesis is actually true. The decision is often made using the p-value.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), and Current Protocols in Protein Science (CPPS), John E. Coligan (ed.), John Wiley and Sons, Inc., 2005 (ISBN 0471142735), the contents of which are all incorporated by reference herein in their entireties.

Imaging Using Contrast Agents

The use of contrast agents in medical diagnostic techniques to enhance tissue contrast or to facilitate the study of body processes is well established. The manner in which contrast enhancement occurs varies from imaging modality to imaging modality but in magnetic resonance imaging most of the conventional contrast agents derive their contrast enhancing power from their effects on the tissue selection times.

MRI, the most representative tomography technique, is a method used to obtain 3-dimensional images non-invasively and that has been widely used for the diagnosis of disease owing to its excellent contrast and spatial resolution. One of the great advantages of MR imaging is the high degree of intrinsic tissue contrast present from tissue relaxations times.

MRI contrast agents are used to improve the visibility of internal body structures by increasing contrast between normal tissues and abnormal tissues in MRI. MRI contrast agents alter the T1 and T2 relaxation times of tissues and body cavities where they are present. Depending on the image weighting, this can give a higher or lower signal. Most MRI contrast agents work through shortening the relaxation time of protons located nearby. Generally, MRI contrast agents are divided into two groups: paramagnetic contrast agents and superparamagnetic contrast agents.

Superparamagnetic nanoparticles comprising superparamagnetic iron oxide (SPIO) as magnetite ($Fe_3O_4$) and maghemite ($Fe_2O_3$) are used clinically. Characteristics of superparamagnetic iron oxide particles include (i) hydrophobicity, (ii) a high ratio of volume to surface area, (iii) can form clusters, (iv) has low stability indicating that both structural and magnetic characteristics can be easily changed; (v) biodegradable; and (4) toxicity. Surface modifications of the particle can be used to overcome toxicity when administered to subjects.

The application of superparamagnetic iron oxide in MR-imaging derives from their ideal combination of a large effect on tissue signal intensity which results in powerful contrast enhancement, and their highly specific targetability. The potential targets of particulate agents are many, depending on the administration route and the physicochemical properties of the particulate material, in particular the particle size and surface characteristics. Their two main applications are by enteral administration for gastrointestinal investigations, and by parenteral administration for investigations of the blood pool compartment and/or the reticuloendothelial system and regions of its anatomical distribution, e.g. the liver, spleen, bone marrow, and lymph nodes. Ultrasmall iron oxide particles with a diameter of less than approximately 30 nm have a relatively long intravascular half-life when compared to larger conventional iron oxide particles. In addition to the T2 shortening typically associated with the iron oxide particles, ultrasmall particles also produce T1 shortening thereby increasing signal within the vessels. Recent advances in particulate agents have also made targeting with receptor ligands or antibodies/antibody fragments possible. A brief summary of described applications of different superparamagnetic agents is given in Fahlvik et al., JMRI 3:187-194 (1993).

Superparamagnetic Iron Oxide Particles

Iron oxide based magnetic nanoparticles have been widely used in a variety of biomedical applications such as magnetic separation, magnetic resonance imaging, hyperthermia, magnetically-guided drug delivery, tissue repair, and molecular diagnostics. For most applications, a polymeric coating is needed to improve the nanoparticles' aqueous stability, biocompatibility and conjugation properties. Typically, dextran-coated iron oxide nanoparticles have been successfully used as magnetic resonance imaging (MRI) contrast agent, due to their strong ability to dephase water protons in surrounding tissue, which results in a decrease in the MRI signal. In addition, the dextran coating can be cross-linked and functionalized with amino groups to facilitate the conjugation of targeting ligands for MRI and in vitro diagnostics applications.

Superparamagnetic iron oxide crystals can be prepared using any method known to those of skill in the art. For example, superparamagnetic iron oxide crystals can be precipitated from an aqueous solution of a mixture of iron salts by rapid addition of a base to pH above 10 while stirring vigorously or during sonication. A wide range of iron salts can be used such as $FeC_{12}.nH_2O$, $FeCl_3.nH_2O$, Fe(III) citrate, Fe(II) gluconate, $FeSO_4.nH_2O$, $Fe_2(SO_4)_3$, Fe(II) oxalate, $Fe(NO_3)_3$, Fe(II) acetylacetonate, Fe(II) ethylenediammonium sulfate, Fe(II) fumarate, Fe(III) phosphate, Fe(III) pyrophosphate, ammonium Fe(III)citrate, ammonium Fe(II)sulfate, ammonium Fe(III) sulfate and ammonium Fe(II) oxalate. The ratio between ferrous and ferric iron can be within the range of 1:5 to 5:1. Such precipitated iron oxide crystals can be represented by the following formula: $(FeO)_x.Fe_2O_3$ where x can be a number in the range of $\leq x \leq 1$. Maghemite, $\gamma$-$Fe_2O_3$, represents the lower x-value while magnetite, $Fe_3O_4$, represents the upper value for x. Bases for precipitating superparamagnetic iron oxide can include a wide range of strong inorganic or organic bases such as NaOH, $NH_4OH$, LiOH, KOH, triethylamine and guanidine. In general, the counter ions for the metal and the base should be physiologically tolerable ions so as to minimize the need for the precipitated crystals to be cleansed of potentially toxic by-products.

The precipitation of iron oxide or, alternatively, the co-precipitation of iron oxide and at least one polymer, can take place in water, a mixture of water and organic solvent(s), or in a viscous medium. As an example, organic solvents like methanol, ethanol, acetone, ethers, and hexane may be used. The viscous matrix can consist of hydrogels of polysaccharides or polyamines, tri-iodinated aromatics, glycerol or polyethylene- and polypropylene-glycols. Precipitation from aqueous solution free from non-physiologically tolerable co-solvents is of course preferred as again the need for post-production purification is reduced. Nanoparticles of a desired size can be isolated and purified by differential column chromatography, centrifugation, and dialysis. Electron microscopy, X-ray diffraction and laser light scattering which may be used to measure median diameter of the resulting nanoparticles.

In one embodiment, the Janus nanoparticle is less than 75 nm in size (e.g., 70, 65, 60, 55, 50, 45, 40, 35, 30, 25, 20, 15 nm or smaller).

In another embodiment, the superparamagnetic iron oxide nanoparticle is less than 20 nm in size (e.g., 19, 18, 17, 16, 15, 14, 13, 12, 11, 10, 9, 8, 7, 6, or 5 nm or smaller).

Carrier Face

In some embodiments, the carrier face of the iron oxide preparation has a polyelectrolyte structure. Without wishing to be bound by theory, polyelectrolytes have the added advantage of improving stability and minimizing toxicity of iron oxide preparations. Polyelectrolytes can include polyanionic and polycationic compounds or a mixture of these that bind strongly to the iron oxide surface through e.g., multiple attachment points.

Coating materials can be grouped depending on their charge and functional groups, such as negatively charged polymers with functional groups containing phosphorus or sulphur atoms or carboxy groups, and positively charged polymers with functional groups containing nitrogen atoms. Examples of negatively charged polymers are certain modifications of carboxycellulose, alginates, carrageenans, polygalacturonate, heparins and heparinoid compounds such as chrondroitin-4-sulphate, dermatansulphate, keratin sulphate and hyaluronate, synthetic polymers such as poly-styrenesulphonate and amino acids such as polyglutamate and polyaspartate. Examples of positively charged polymers include chitosan and polylysine. In one embodiment, the polymer(s) must comprise multiple (more than one) functional groups to secure multiple attachment points to the metal oxide crystals and give the particles a charged surface.

Targeting Face

The targeting face of Janus nanoparticle comprises at least one targeting moiety, e.g., at least 2, at least 3, at least 4, at least 5, at least 6, at least 7, at least 8, at least 9, at least 10, at least 11, at least 12, at least 13, at least 14, at least 15, at least 20, at least 25 or more targeting moieties.

The targeting moiety can be a small molecular weight compound (e.g. mono or disaccharide) or a macromolecule (e.g. protein, polysaccharide) and can be associated with the nanoparticle by covalent or non-covalent interactions.

In certain embodiments, the targeting moiety can target the theranostic composition to a binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv)2 fragments), diabodies, tribodies or tetrabodies, which typically are covalently linked or otherwise stabilized (i.e., leucine zipper or helix stabilized) scFv fragments; and other targeting moieties include for example, aptamers, receptors, ligands, and fusion proteins.

In general, antibodies can be raised to any desired antigen, using the many conventional techniques now well known in the art.

When targeting a cancer cell, a specific antigen can be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2. For other forms of cancer and their metastases, a specific marker or markers may be selected from cell surface markers such as, for example, vascular endothelial growth factor receptor (VEGFR) family, a member of carcinoembryonic antigen (CEA) family, a type of anti-idiotypic mAB, a type of ganglioside mimic, a member of cluster designation differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, and a type of human carcinoma antigen.

Encapsulation of jNP

The Janus nanoparticles (jNP) described herein can be coated with a polymeric shell comprising e.g., non-biodegradable or biodegradable polymers, however, biodegradable polymers are preferred. The polymer can be natural or synthetic, with synthetic polymers being preferred due to the better characterization of degradation and, where appropriate, release profile of an incorporated agent. The polymer can be selected based on the period over which degradation or release of an agent is desired, generally in the range of at several weeks to several months, although shorter or longer periods may be desirable.

Representative, non-limiting examples of biodegradable polymers include synthetic polymers such as polymers of lactic acid and glycolic acid, polyanhydrides, poly(ortho) esters, polyurethanes, poly(hydroxybutiric acid), poly(valeric acid), and poly (lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin, and other hydrophilic proteins. The compositions described herein can also comprise bioerodible hydrogels which are prepared from materials and combinations of materials such as polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly (hexylmethacrylate), poly (isodecyl methacrylate), poly (lauryl methacrylate), poly (phenyl methacrylate), poly(methyl acrylate), poly(isopropyl acrylate), poly(isobutyl acrylate), and poly(octadecyl acrylate). Preferred biodegradable polymers are polyglycolic acid, polylactic acid, copolymers of glycolic acid and L- or D,L-lactic acid, and copolymers of glycolide and L- or D,L-lactide. Those of skill in the art will appreciate that the molecular weight of the polymer can be varied to tailor the properties of the particle.

The foregoing exemplary natural and synthetic polymers are, of course, either readily available commercially or are obtainable by condensation polymerization reactions from the suitable monomers, comonomers, or oligomers. For instance, homopolymers and copolymers of glycolic and lactic acids can be prepared by direct poly-condensation or by reacting glycolide and lactide monomers (Gilding, D. K., et al., Polymer, 20:1459 (1979)).

The compositions described herein can also include a conjugate of a lipid and a hydrophilic polymer, referred to as a 'lipopolymer.' Lipopolymers can be obtained commercially or can be synthesized using known procedures. For example, lipopolymers comprised of methoxy(polyethylene glycol) (mPEG) and a phosphatidylethanolamine (e.g., dimyristoyl phosphatidylethanolamine, dipalmitoyl phosphatidylethanolamine, 1,2-distearoyl-3-sn-glycerophosphoethanolamine (distearoyl phosphatidylethanolamine (DSPE)), or dioleoyl phosphatidylethanolamine) can be obtained from Avanti Polar Lipids, Inc. (Alabaster, Ala.) at various mPEG molecular weights (350, 550, 750, 1000, 2000, 3000, 5000 Daltons). Lipopolymers of mPEG-ceramide can also be purchased from Avanti Polar Lipids, Inc. Preparation of lipid-polymer conjugates are known in the art and are not described in detail herein.

The hydrophobic component of the lipopolymer can be virtually any hydrophobic compound having or modified to have a chemical group suitable for covalent attachment of a hydrophilic polymer chain. Exemplary chemical groups are, for example, an amine group, a hydroxyl group, an aldehyde group, and a carboxylic acid group. Preferred hydrophobic components are lipids, such as cholesterol, cholesterol derivatives, sphingomyelin, and phospholipids, such as phosphatidylcholine (PC), phosphatidylethanolamine (PE), phosphatidylglycerol (PG), phosphatidic acid (PA), phosphatidylinositol (PI), where the two hydrocarbon chains are typically between about 8-24 carbon atoms in length, and have varying degrees of unsaturation. These lipids are exemplary and are not intended to be limiting, as those of skill can readily identify other lipids that can be covalently modified with a hydrophilic polymer and incorporated into the particles described herein. In some embodiments, the lipopolymer is formed of polyethylene-glycol and a lipid, such as distearoyl phosphatidylethanolamine (DSPE), PEG-DSPE. PEG-DSPE has some degree of biodegradability in vivo, by virtue of the hydrolysable bonds between the fatty acids and the glycerol moiety.

It is also contemplated herein that the iron oxide nanoparticles are encapsulated in a polymer, for example, PLGA such that the PLGA forms a shell around the iron oxide nanoparticle. Encapsulation of the compositions described herein can be used e.g., to deliver poorly soluble drugs. The polymer-coated nanoparticles remain magnetic and can be prepared using the techniques described herein, for example, a surface layer-by-layer covalent coupling method. Other polymer shell compositions are also contemplated herein.

Bioactive Agents

In some embodiments, the compositions described herein further comprise a biologically active agent. A variety of different pharmaceutical/therapeutic agents can be used in conjunction with the methods and compositions described herein and include, but are not limited to, small molecules, proteins, antibodies, peptides and nucleic acids. In one embodiment, the bioactive agent comprises a nucleic acid, such as DNA, RNA, siRNA, miRNA, oligonucleotide, shRNA, etc.

In general, bioactive agents which can be administered via the invention include, without limitation: anti-infectives such as antibiotics and antiviral agents; chemotherapeutic agents (i.e. anticancer agents); anti-rejection agents; analgesics and analgesic combinations; anti-inflammatory agents; hormones (e.g., steroids); growth factors (e.g., bone morphogenic proteins (i.e. BMP's 1-7), epidermal growth factor (EGF), fibroblast growth factor (i.e. FGF 1-9), platelet derived growth factor (PDGF), insulin like growth factor (IGF-I and IGF-II), transforming growth factors (i.e. TGF-β-III), vascular endothelial growth factor (VEGF)); anti-angiogenic proteins such as endostatin, and other naturally derived or genetically engineered proteins, polysaccharides, glycoproteins, or lipoproteins. Additionally, the particles described herein can be used to deliver any type of molecular compound, such as for example, pharmacological agents, vitamins, sedatives, steroids, hypnotics, antibiotics, chemotherapeutic agents, prostaglandins, and radiopharmaceuticals. The compositions described herein are suitable for delivery of the above materials and others including, but not limited to, proteins, peptides, nucleotides, carbohydrates, simple sugars, anti-thrombotics, anti-metabolics, growth factor inhibitors, growth promoters, anticoagulants, antimitotics, fibrinolytics, anti-inflammatory steroids, drugs, and monoclonal antibodies, among others.

In one embodiment, the bioactive agent is a chemotherapeutic agent. Chemotherapeutic agents are typically cytotoxic antineoplastic drugs that find use as part of a standardized regimen of cancer treatment. Chemotherapy can be given with a curative intent or it may aim to prolong life or to palliate symptoms. It is often used in conjunction with other cancer treatments, such as radiation therapy or surgery. Certain chemotherapeutic agents also have a role in the treatment of other conditions, including ankylosing spondylitis, multiple sclerosis, Crohn's disease, psoriasis, psoriatic arthritis, rheumatoid arthritis, and scleroderma.

Linker Groups

In some embodiments, the compositions provided herein further comprise a linker group, for example, between the polymer and a targeting moiety or between the polymer and the iron oxide core. In some embodiments the linker moiety is cleavable by an enzyme e.g., an esterase present in a target tissue or cell. In some embodiments, the linker moiety is cleavable by one type of esterase (e.g., a first type of an esterase present in a first cell type, e.g., a kidney cell) and is not cleavable by another type of esterase (e.g., a second type of esterase present in a second cell type, e.g., a cardiac cell). Thus, cleavage of the linker and activation of the drug and detectable moieties can be specific for a targeted cell type.

In one embodiment, the linker group comprises a functionalized phospholipid, such as a thiol-functionalized phospholipids, an amine functionalized phospholipids, or any combination thereof. In another embodiment, the amine-functionalized phospholipids can comprise DSPE-PEG(2000)Carboxylic Acid, DSPE-PEG(2000)Maleimide, DSPE-PEG(2000)PDP, DSPE-PEG(2000)Amine, DSPE-PEG(2000)Biotin, or any combination thereof. In another embodiment, the thiol-functionalized phospholipids can comprise phosphatidylthioethanol (PTE).

The present invention may be as defined in any one of the following numbered paragraphs:

1. A composition comprising: a microbubble with a Janus nanoparticle associated with the surface, wherein the Janus nanoparticle comprises a superparamagnetic iron oxide nanoparticle having a nucleic acid delivery face and a targeting face, and wherein the nucleic acid delivery face and the targeting face are distinct from one another.

2. The composition of paragraph 1, wherein the Janus nanoparticle is less than 75 nm in size.

3. The composition of paragraph 1 or 2, wherein the superparamagnetic iron oxide nanoparticle is less than 20 nm in size.

4. The composition of paragraph 1, 2, or 3, wherein the Janus nanoparticle is asymmetrically shaped.

5. The composition of paragraph 4, wherein the Janus nanoparticle is avocado shaped.

6. The composition of paragraph 5, wherein the targeting face is situated at the upper part of the avocado shaped nanoparticle, and the carrier face is situated at the round, bottom part of the avocado shaped nanoparticle.

7. The composition of any one of paragraphs 1-5, wherein the targeting face comprises a targeting moiety selected from the group consisting of: a targeting peptide, a polyclonal antibody, a monoclonal antibody, an antibody binding fragment, a composite antibody, a recombinant antibody, a cell penetrating peptide and a matrix interacting peptide.

8. The composition of paragraph 7, wherein the targeting moiety binds to a cell surface or cell matrix protein.

9. The composition of any one of paragraphs 1-8, wherein the carrier face comprises a polymer.

10. The composition of paragraph 9, wherein the polymer comprises a polyelectrolyte.

11. The composition of paragraph 10, wherein the polyelectrolyte is a cationic polyelectrolyte or an anionic polyelectrolyte.

12. The composition of any one of paragraphs 1-11, wherein the Janus nanoparticle comprises an iron oxide core with a PEG brush.

13. The composition of any one of paragraphs 1-12, wherein the PEG brush is a mixed 3:1 short-long PEG brush.

14. The composition of any one of paragraphs 1-13, wherein the moieties in the targeting and carrier faces are covalently coupled or tethered to the long PEG in the mixed PEG-brush.

15. The composition of any one of paragraph 1-14, wherein the iron oxide core is encapsulated within a polymer.

16. The composition of paragraph 15, wherein the polymer-encapsulated iron oxide core further comprises a bioactive agent.

17. The composition of any one of paragraphs 1-16, wherein the composition further comprises a bioactive agent.

18. The composition of any one of paragraphs 1-17, wherein the bioactive agent comprises a nucleic acid molecule.

19. The composition of paragraph 18, wherein the nucleic acid molecule is sandwiched between the microbubble and the carrier face of the Janus nanoparticle.

20. The composition of any one of paragraphs 1-18, wherein the composition is formulated for use as a magnetic resonance imaging (MRI) contrast agent.

21. The composition of any one of paragraphs 1-20, wherein the MRI contrast agent comprises a shorter $T_2^*$-relaxivity.

22. The composition of paragraph 20, wherein the MRI contrast agent is a negative contrast agent.

23. A composition for use as an MRI contrast agent comprising: a Janus nanoparticle, which comprises a superparamagnetic iron oxide nanoparticle having a nucleic acid delivery face and a targeting face, and wherein the nucleic acid delivery face and the targeting face are distinct from one another.

24. The composition of paragraph 23, wherein the MRI contrast agent is a negative contrast agent.

25. The composition of paragraph 23 or 24 for use in detection and/or monitoring of electron paramagnetic resonance (EPR) imaging.

26. A composition for use as an MRI contrast agent for target-specific imaging, the composition comprising: a Janus nanoparticle, which comprises a superparamagnetic iron oxide nanoparticle having a nucleic acid delivery face and a targeting face, and wherein the nucleic acid delivery face and the targeting face are distinct from one another, and wherein the targeting face comprises an antibody directed to a target to be imaged.

27. The composition of paragraph 26, wherein the target to be imaged is a tumor.

28. A method for imaging, the method comprising: (a) administering to a subject an MRI contrast agent comprising: a Janus nanoparticle, which comprises a superparamagnetic iron oxide nanoparticle having a nucleic acid delivery face and a targeting face, and wherein the nucleic acid delivery face and the targeting face are distinct from one another, and (b) performing an MRI on the subject.

29. The method of paragraph 28, wherein the MRI comprises electron paramagnetic resonance (EPR) imaging.

30. A method for target-specific imaging, the method comprising: (a) administering to a subject an MRI contrast agent comprising: a Janus nanoparticle, which comprises a superparamagnetic iron oxide nanoparticle having a nucleic acid delivery face and a targeting face, wherein the nucleic acid delivery face and the targeting face are distinct from one another, and wherein the targeting face comprises an antibody directed to a target to be imaged, and (b) performing an MRI on the subject.

31. Use of a composition of any one of paragraphs 1-27 as an MRI contrast agent.

32. Use of a composition of any one of paragraphs 1-27 as a drug delivery device.

33. Use of a composition of any one of paragraphs 1-27 as a nucleic acid delivery device.

EXAMPLES

Nanotechnologies present great untapped potential to solve much needed minimally invasive cancer monitoring and effective delivery of nucleic acid, DNA and RNAi (siRNA/miRNA) therapies that directly address genetic and epigenetic changes associated with non-curable cancers. However, to date multifunctional nanotechnologies have shown key limitations in efficacy and/or safety that impede clinical translation.[1-3] Even with tumor-specific targeting, nanoplatforms dependent on endocytosis/macropinocytosis for intracellular delivery remain inefficient due to limited (<2%) escape of nucleic acid-cargo from endosomes into the cytosol[1,4] and the likelihood that the majority (>70%) of internalized nucleic acid-cargo will be exocytosed.[5] Even if delivered intact, DNA/RNAi-payloads must integrate into cellular machinery for functional efficacy.[1] Moreover, many of the efficient in vitro nano-delivery systems, e.g. self-assembled PEI-polyplexes, display toxic effects arising from excess cationic material and/or from release of high MW or branched-PEI$_{25kDa}$ resulting from disassembly in vivo.[2] While sonoporation-induced cytosolic-delivery of nucleic acids carried by microbubbles (MBs) may bypass some drawbacks associated with endosomal uptake, current MB technologies remain inefficient.[6,7] New nanoparticle designs should thus explore more efficient endocytosis-independent mechanisms to deliver DNA/RNAi-payloads, and at the same time, eliminate excess unincorporated materials.[1] Ideally, such a particle would also be modular, multifunctional,[12] and inherently versatile to accommodate multiple targeting and payload moieties to address genetic/epigenetic heterogeneity in cancers. Other considerations include charge, hydrophilicity, shape, and size,[8-11] as well as non-aggregability.

Janus nanoparticle designs spatially separate multifunctional components to eliminate confounding multicomponent steric/chemical interactions,[12,13] and thus have potential to meet criteria for versatility and multifunctionality. Although existing jNPs are typically >100 nm,[12-17] and hence too large for efficient cellular uptake and nucleic acid delivery, efficient delivery would be possible with ultrasmall jNPs capable of forming composites with MBs. Such composites offer the additional advantage of unexplored dual mode magnetic resonance (MR) and ultrasound diagnostic potential. This type of dual mode MR/ultrasound imaging has already been described for "nano-in-micro" composites of iron oxide nanoparticles encapsulated within microbubbles[1,14] or within their shell[18,19] but these composites are not designed for nucleic acid delivery.[1,14,18-19] Based on inherent advantages of Janus-designs and nano-in-micro composites, it was hypothesized that covalent-layered ultrasmall jNPs alone or composite[16,12] could facilitate tumor-specific detection and targeted nucleic acid delivery with modular versatility in targeting and payload.

Presented herein, in part, is the novel design and preparation of ultrasmall, covalent-layered jNPs comprised of a 10-nanometer (nm) iron oxide core surrounded by opposing antibody-targeting and cationic-payload faces. These jNPs and self-assembled jNP-MBs, comprise a modular targetable nanoplatform that enhances MR- and ultrasound-imaging of tumor-specific features, and delivers both DNA and miRNA to tumors more efficiently and safely than current technologies. These results demonstrate that jNPs and jNP-MBs provide a versatile and tunable theranostic platform to advance cancer detection and delivery of nucleic acid therapy.

Provided herein, in one embodiment, are Janus nanoparticles (jNPs; 20-30 nm by Cryo-TEM), consisting of an ultra-small (10 nm) superparamagnetic iron-oxide (USPIO) core with a mixed PEG-brush onto which a payload-face is covalently layered on one side and an antibody targeting-face layered on the opposing side. The jNPs are stable, bind DNA, exhibit shortened MR-T2* relaxivity for contrast-enhanced MRI-detection of tumors at 24-hours using 50 ng Fe/kg, without inducing adverse events or inflammation. The jNPs self-assemble with echogenic [DNA/miRNA]-coated microbubbles (MBs) to form non-aggregating jNP [DNA/miRNA]MB-heteroplexes. jNP heteroplexes enhance ultrasound molecular-imaging of tumor microvessels and can deliver reporter-gene DNA and tumor suppressor miRNA-126 by sonoporation to breast and pancreatic tumor models, resulting in expected tumor-fluorescence and decreased oncogenic-KRAS protein levels, respectively. The jNPs can encapsulate pharmacologically incompatible drugs or small molecules in order to have favorable pharmacokinetic or pharmacodynamics profiles for efficacious delivery, for efficacious targeted delivery via the jNP targeting moieties, and for combinatorial delivery of nanocapsule encapsulated bioagents. Greater efficiency is noted in imaging and delivery compared to current technologies. Altogether, these data provide proof-of-principle that jNPs and jNP/MB-heteroplexes are a modular dual imaging and delivery platform for DNA/miRNA-therapy for cancer.

Example 1: Results

Covalently layered, ultrasmall Janus-nanoparticle (jNPs) Janus-nanoparticles were sequentially covalent-layer-coupled via modified surface-initiated conjugation[10] (FIG. 1). Layer-1 ("payload-face"), is comprised of 1PEI$_{25K}$ adsorbed onto mica to enable unidirectional sequential layering (FIG. 1A). Layer-2 (glutaraldehyde) covalently links amines in 1PEI$_{25K}$ (Layer-1) with amine-terminated PEG chains in Layer-3 (USPIONs pre-synthesized with a mixed polymer brush).[20] The mixed PEG$_{2K/3.4K-NH2}$ brush was selected to prevent USPION aggregation[21,22] and to expose free amines for antibody targeting[23] (FIG. 1A). The 10-nm USPION-size was selected to optimize MR-imaging[24] and enhance MR-T2*-weighted contrast by PEI.[25] Layer-4 (N-hydroxysuccinimide-ester-maleimide (NHS-MAL))[22,26] crosslinks free amines on Layer-3 to cysteine thiol groups of targeting-antibodies (Layer-5).

Figure 1B:
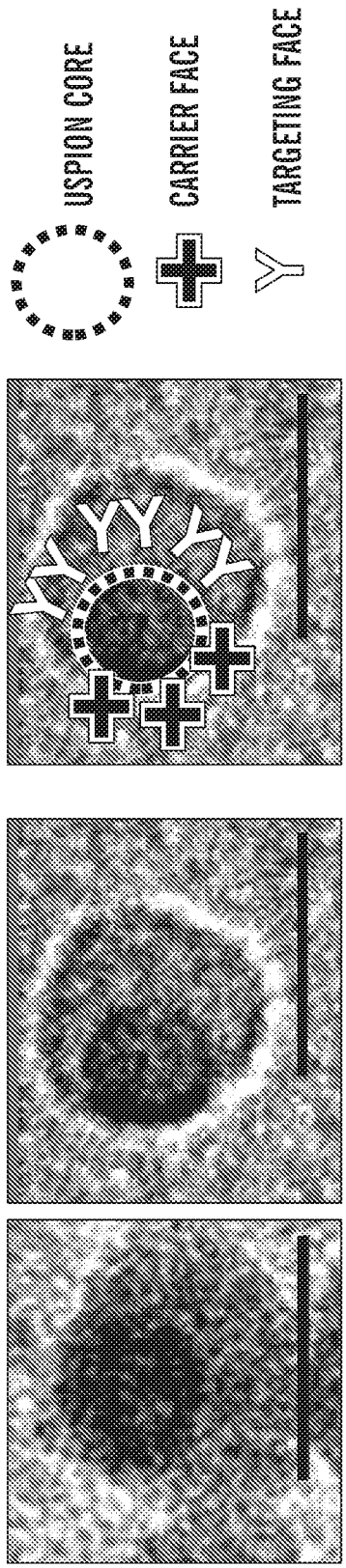
Figure 1C:
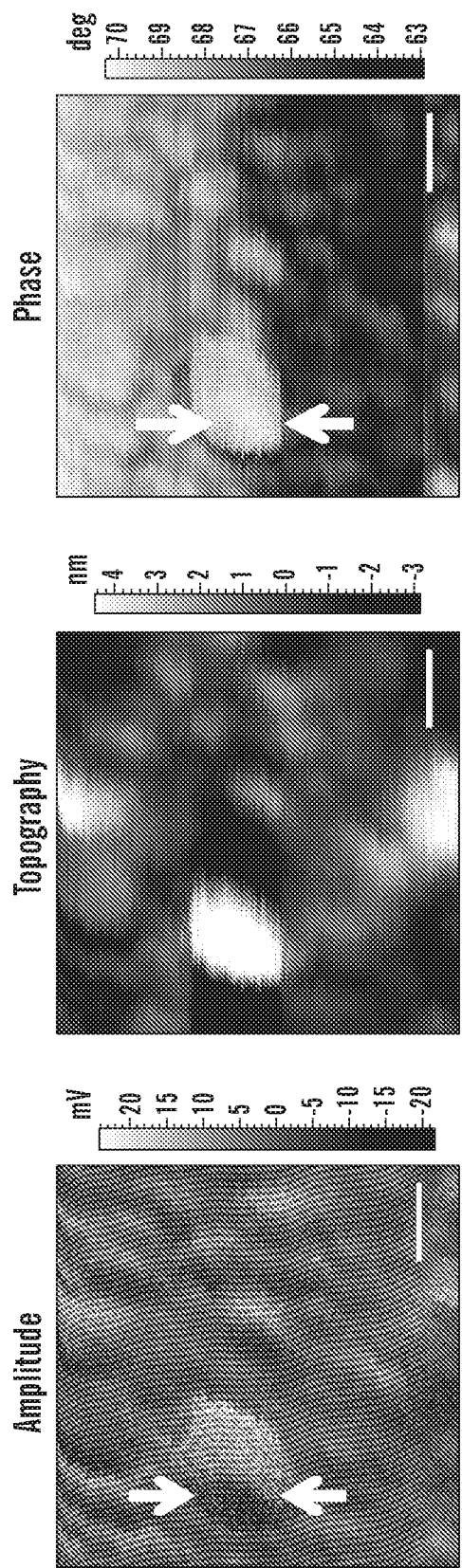

The jNP is projected to be ~27-30 nm based on a 10-nm USPION-core, and ~5-8-nm PEG mixed brush layer. Cryo-transmission electron microscopy (cryo-TEM) revealed asymmetric 22-30-nm particles with the USPION-core resembling an "avocado pit" and a ~12-nm opposing tapered face (FIG. 1B). Mostly single jNPs were observed, but free USPIONs, doublets, triplets, or clusters of jNPs (~35-70% in different cryo-TEM images) were also seen, permitting room for further optimization. Atomic force microscopy (AFM) confirmed asymmetrically functionalized USPION cores, distinguishing dense USPIONs from less dense material (FIG. 1C). AFM measurements (~55-nm avocado-shape) were slightly larger than cryo-TEM measurements, likely due to flattening of 3-dimensional jNPs during imaging (FIG. 1C).

Figure 2A:
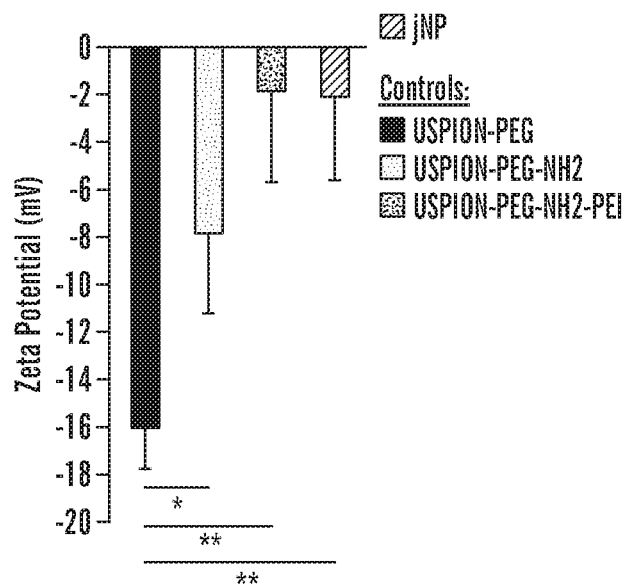
FIGS. 2A-2F In vitro characterization of jNPs.
Figure 2B:
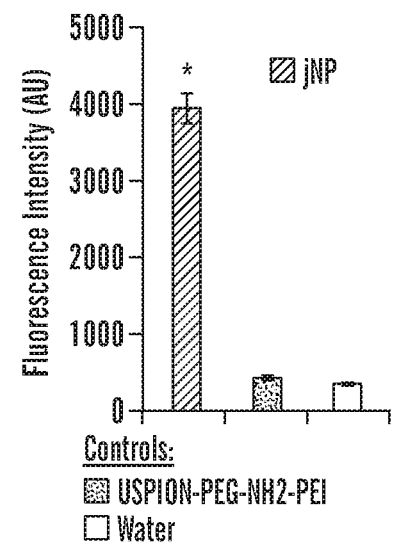
Figure 2C:
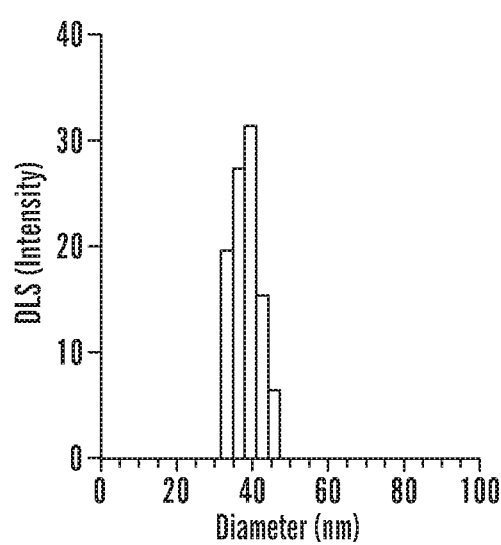

Coupling of layer-specific components was confirmed by measuring changes in zeta-potential with each layer addition (FIG. 2A) and by gain of fluorescence upon fluorophore-labeled antibody attachment (FIG. 2B). Measurement of protein/jNP in 3 independent jNP batches detected a range of 3-12 antibody molecules/jNP (Table 1), providing multivalency for improved targeting.[27] This finding is consistent with the 9 antibodies/jNP predicted theoretically if antibodies are approximated as 12-nm diameter spheres.[27] Typically, $10^{12}$-$10^{13}$ jNPs/mica[29] ($10^{12}$ jNPs~5-ng Fe) were obtained. Dynamic light scattering (DLS) gave larger average hydrodynamic diameters ~30-47 nm (FIG. 2C), consistent with known surface charge effects.[30,31]

TABLE 1

Determination of the number of antibodies per jNP

| | DLS (nm) | # jNPs/ml | 1:20 dilution μg protein/ml | 1:1 μg protein/ml | μg protein/jNP | # of ab/jNP: |
|---|---|---|---|---|---|---|
| 1 | 143 | $1.3 \times 10^{13}$ | 1.97 | 39.46 | 3.0E+14 | 12 abs/jNP |
| 2 | 50.6 | $3.3 \times 10^{13}$ | 3.47 | 69.38 | 2.3E+14 | 9 abs/jNP |
| 3 | 32 | $9.2 \times 10^{13}$ | 4.02 | 80.43 | 8.9E+13 | 3.5 abs/jNP |

Legend: ab, antibody; DLS, dynamic light scattering; μg, microgram; nm, nanometer. Calculation of ab/jNP based on $2.5 \times 10e-13$ μg/ab.

The number of antibody particles to janus nanoparticle was estimated at 9 mAbs/jNP by using assumptions of 12-nm globular-shaped IgG antibody molecule arranged around a 10 nm-USPION core while sitting on a flat surface (mica sheet in the layer-by-layer covalent conjugation process). To verify this estimate, 3 independent preparations of jNPs were analyzed—each with different measured diameters by dynamic light scattering (DLS), and specific number of jNPs per batch prepared. Protein amounts were determined by standard BCA assays following manufacturer's specifications, and within the ideal optimal sensitivity-range for assay detection.

~3.5 to 12 antibody molecules were detected per jNP. The number of antibodies per jNP trended with DLS measurement of average diameter of jNPs. It is noted that the 50 nm diameter jNP has 9 antibody molecules as predicted.

jNP Stability in Serum and Nucleic Acid Binding Affinity

Figure 2D:
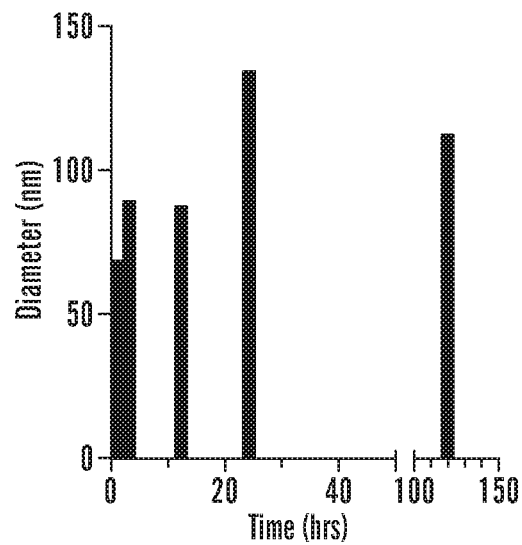
Figure 2E:
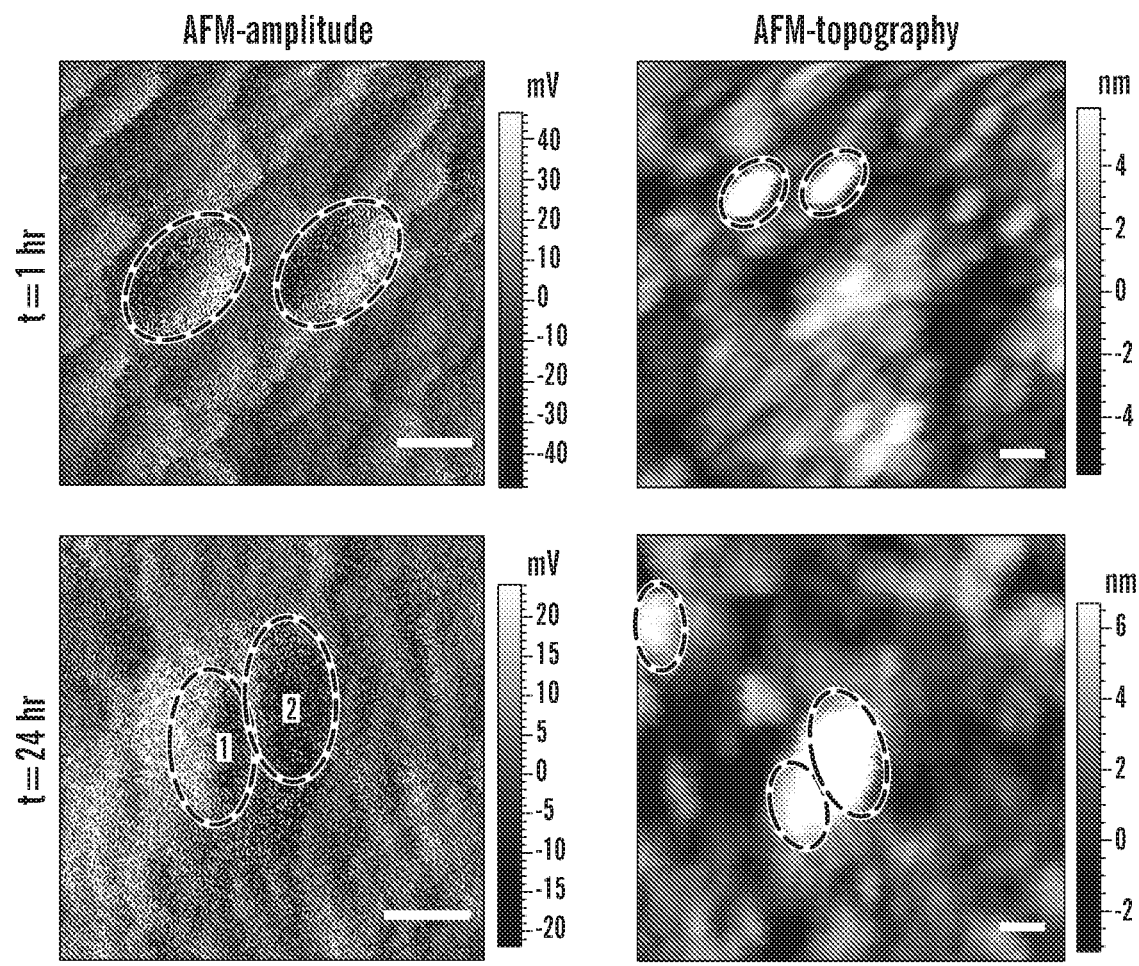

To test jNP stability for in vivo applications, the inventors assessed changes in jNP size and morphology over 24-hr in 75%-serum. A representative jNP batch showed size stability at ~85 nm for 12-hrs, increasing to 134.5-nm by 24-hr and 112-nm at 3 days (FIG. 2D). Although batch-to-batch variations occur, size increases were limited and non-progressive (FIG. 2D). Likewise, AFM amplitude and topography images showed that jNPs retain characteristic avocado-shaped morphologies seen on cryo-TEM for at least 24-hr in 75%-serum (FIG. 2E).

Figure 2F:
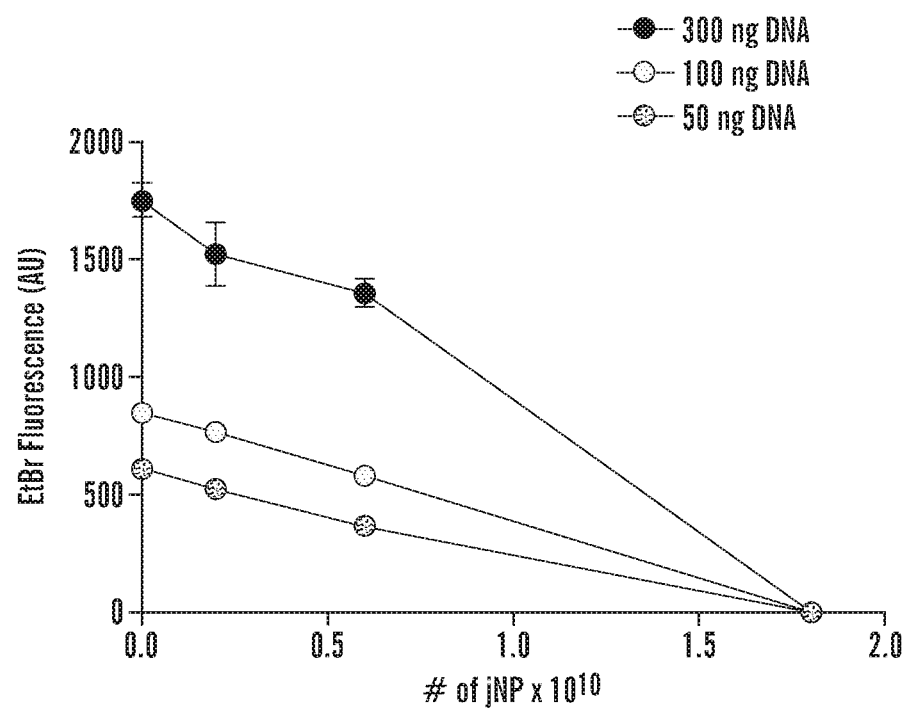
Figure 2F:
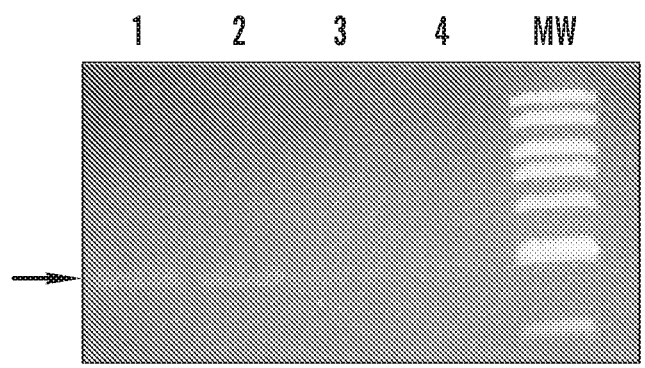
Figure 7A:
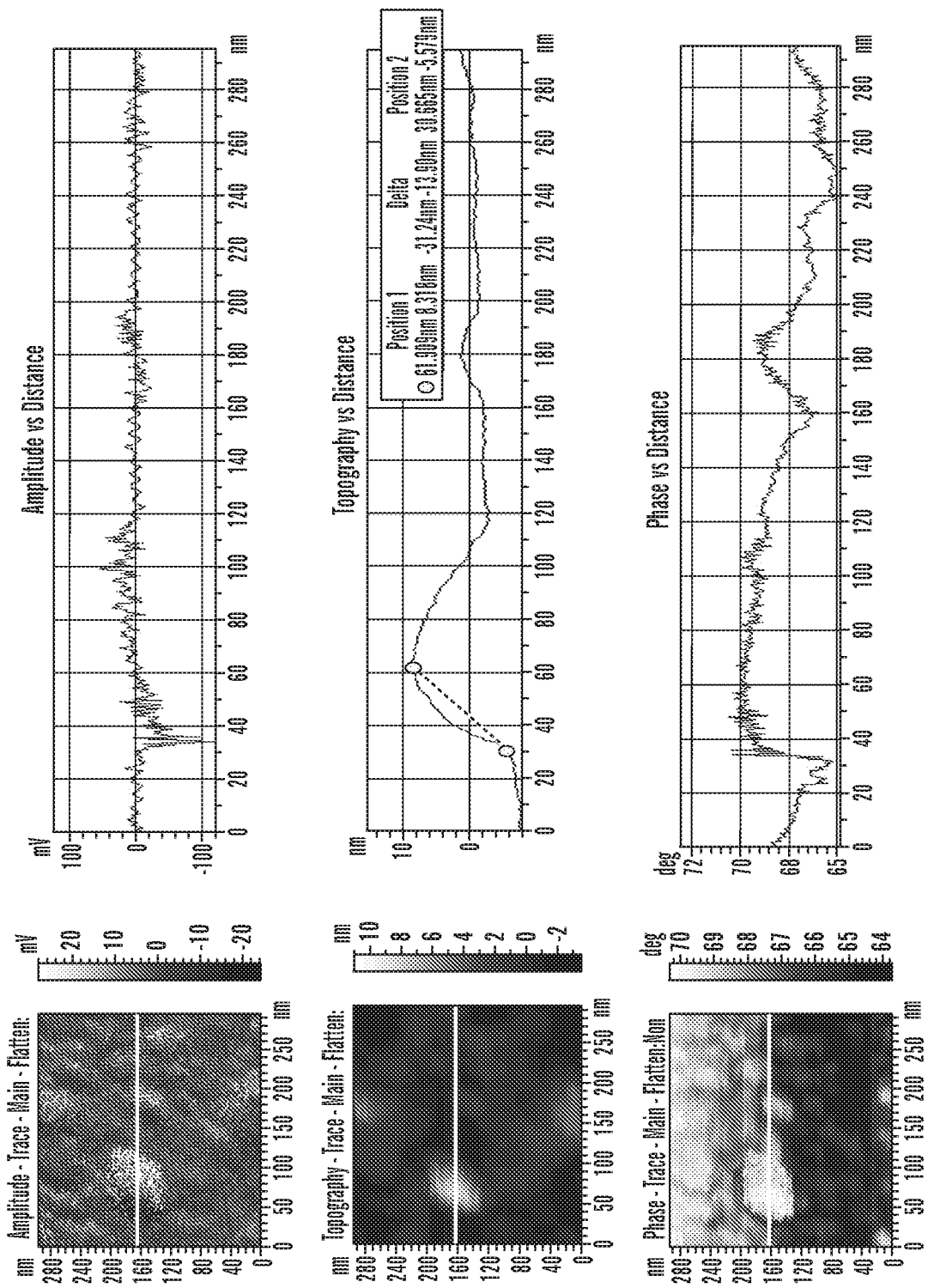
FIGS. 7A-7B Representative Atomic Force Microscopy (AFM) images showing (FIG. 7A) analysis of an individual jNP showing amplitude, topography, and phase images with respective trace plots and (FIG. 7B) jNP binding to deposited lambda phage DNA on a mica surface.
Figure 7B:
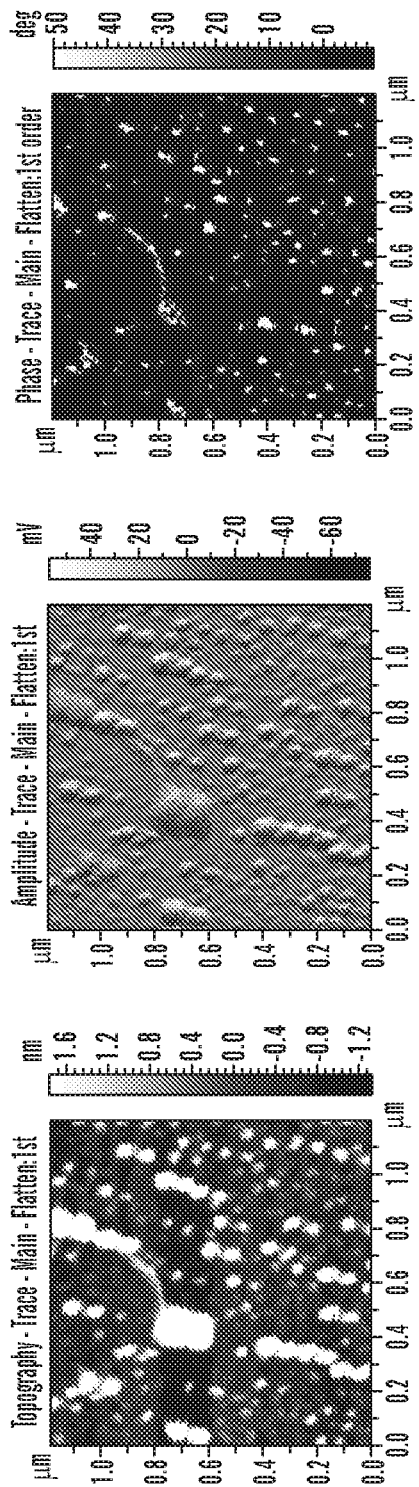
Figure 8A:
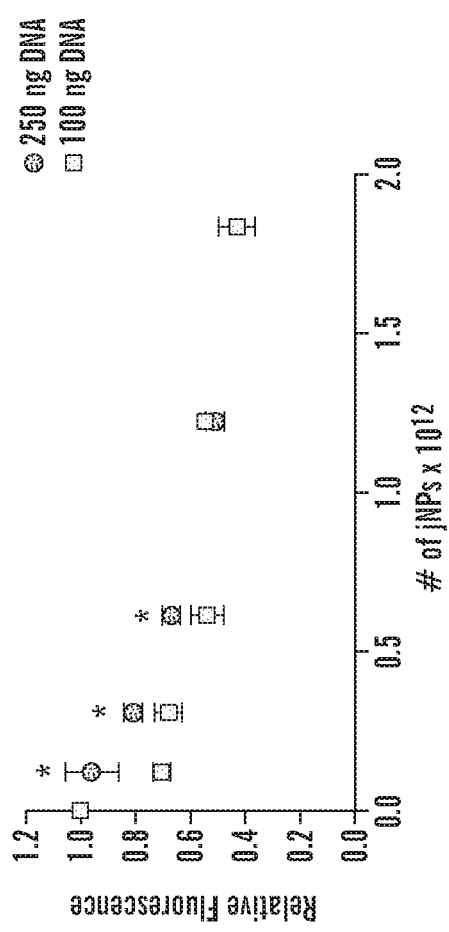
FIGS. 8A-8C Additional in vitro characterization of jNP binding to DNA, and to [DNA]MBs.

To demonstrate jNP function as carriers for nucleic acids, the inventors visualized binding of lambda phage double-stranded DNA to jNPs by AFM (FIG. 7B) and confirmed jNP-DNA binding via an ethidium bromide (EtBr) dye exclusion assay.[32,33] In the latter, jNPs bind DNA in a concentration-dependent manner and compete with EtBr-intercalation into DNA base-pairs, resulting in decreasing EtBr-fluorescence with increasing jNP concentrations (FIG. 2F). jNP-dependent binding to, and resultant protection of DNA from EtBr intercalation, was confirmed on agarose gel electrophoresis (FIG. 2F). Moreover, the reverse experiment showed that jNPs displace EtBr intercalated into DNA using a 4:1 DNA-EtBr ratio prior to addition of jNPs (FIG. 8A).

Self-Assembly of jNP-MBs

Figure 3A:
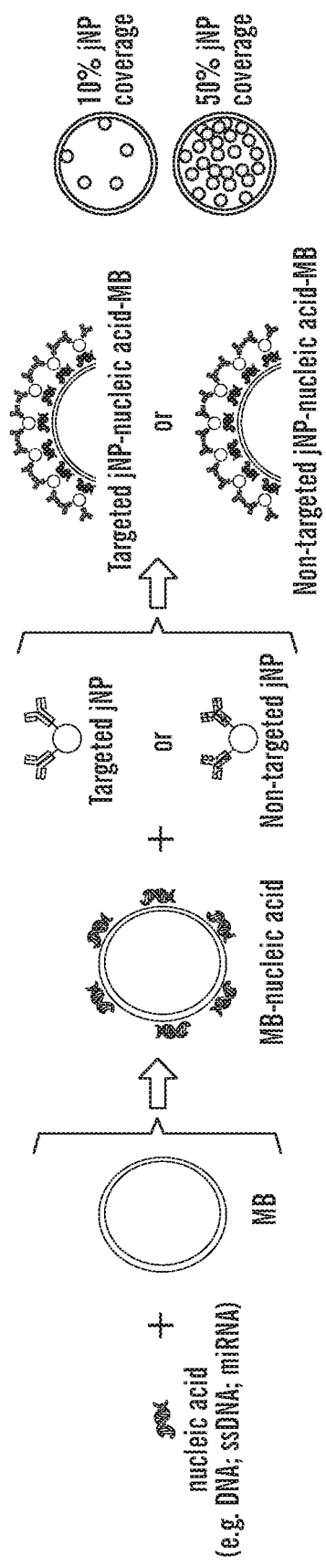
FIGS. 3A-3E In vitro analysis of Janus nanoparticle (jNP) targeting and carrier functions.
Figure 3B:
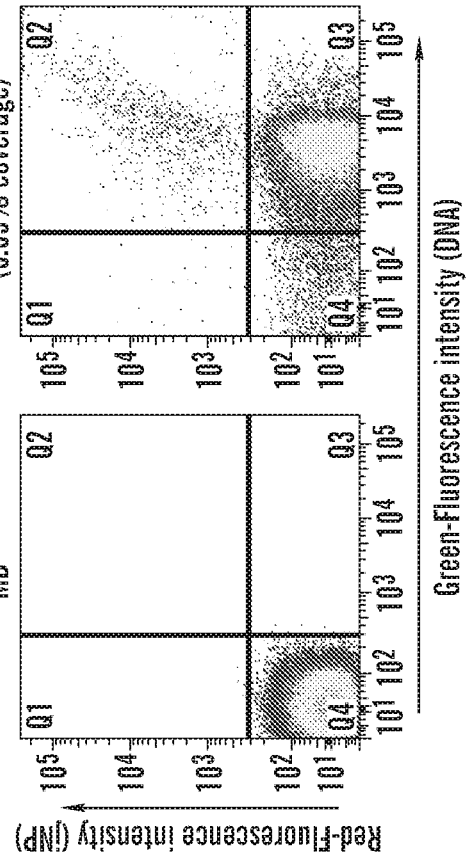

We next verified jNP-MB self-assembly (FIG. 3A) using differential-fluorophore fluorescence-activated cell-sorting (FACS) analysis (FIG. 3B). From 1 to 24-hours after addition of jNPs, the inventors detected DNA binding to ~60-90% of non-fluorescent MBs by single-fluorescent AF488-positive MBs (Q3, FIG. 3B), and detected jNP (0.05% MB-coverage) binding to 3-4% of MB-DNA, forming jNP-DNA-MBs as detected by double-fluorescence (Q2, FIG. 3B). Similar findings at 1-hr (data not shown) and 24-hr indicate relative stability of MB-DNA and of jNP-DNA-MBs in 150 mM NaCl.

Figure 3C:
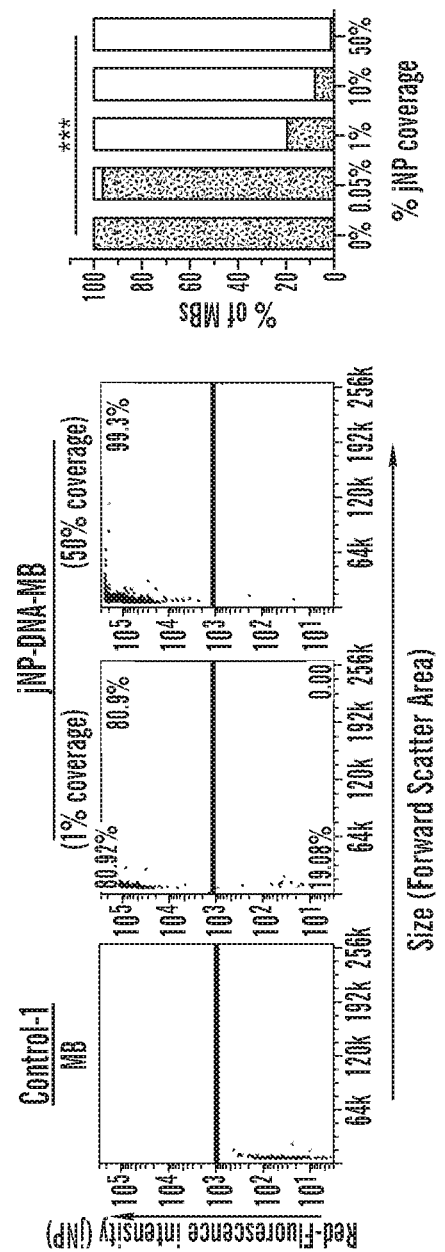
Figure 8B:
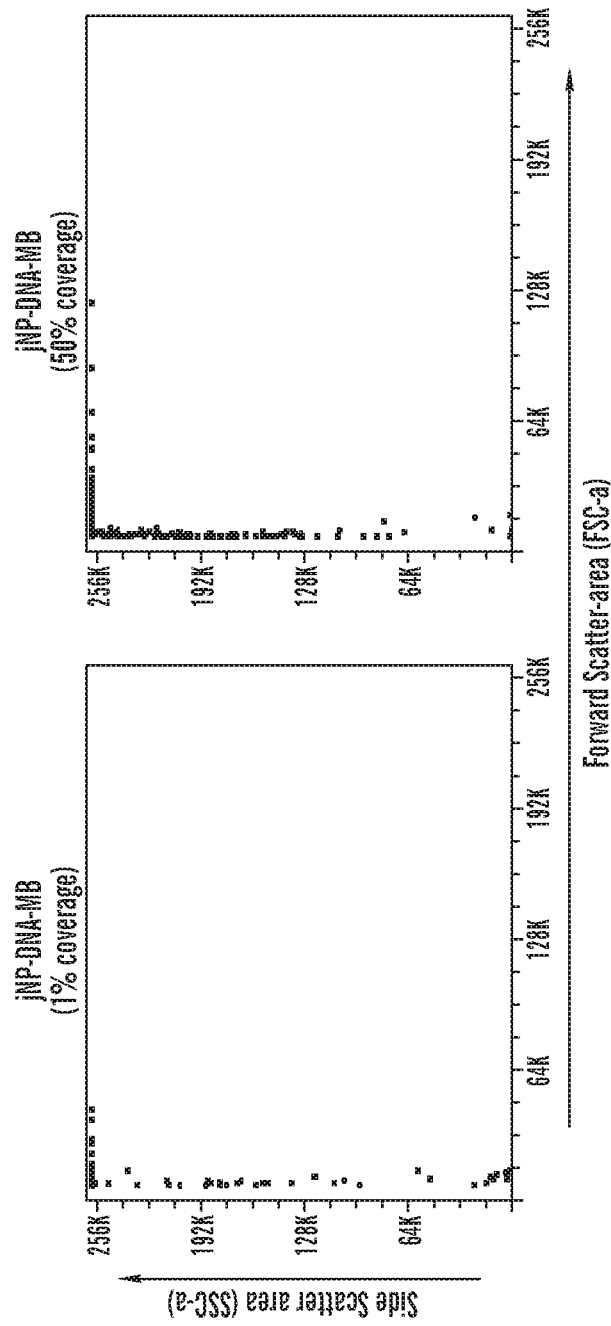
Figure 8C:
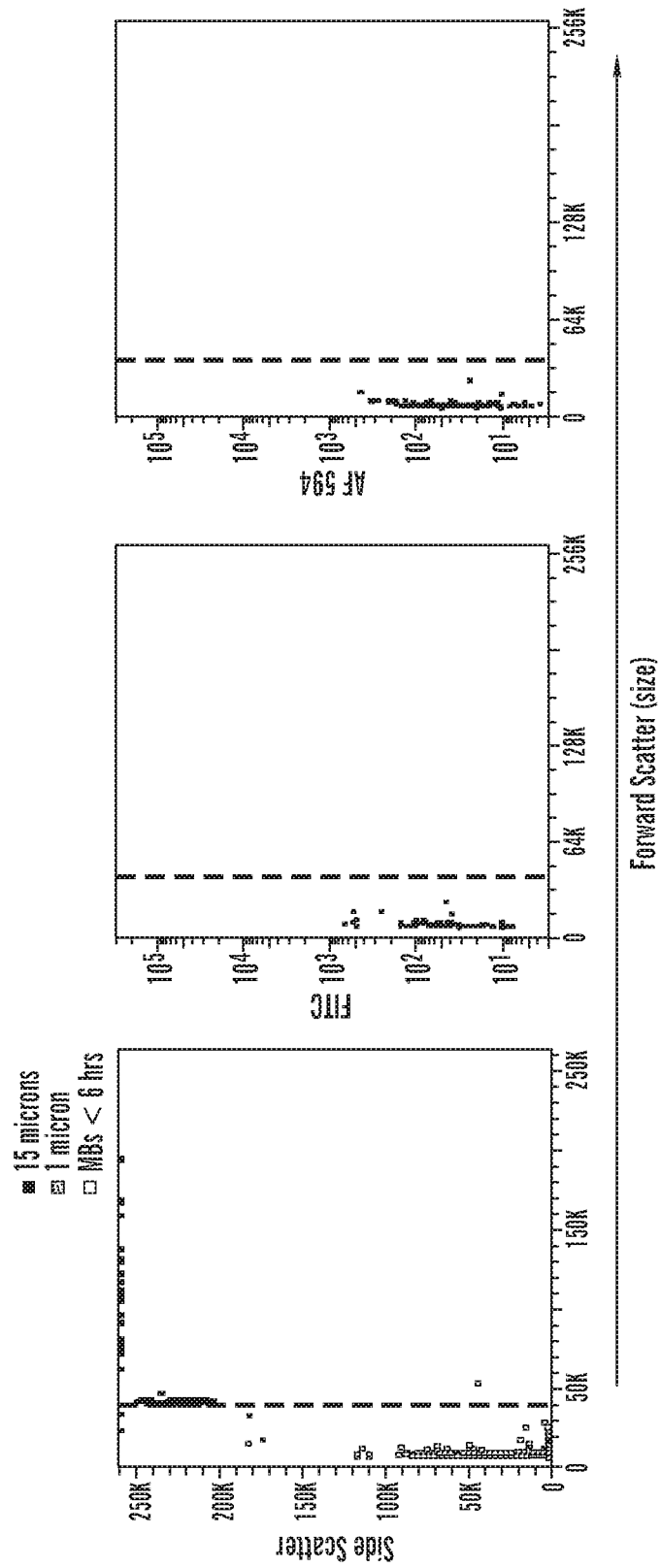

To obtain a higher yield of jNP-DNA-MBs and test 'dose-response' specificity of jNP binding to MB-DNA, increasing amounts of jNPs were added to increase %-MB surface coverages: 1% ($10^3$ jNPs/MB), 10% ($10^4$ jNPs/MB) and 50% ($5 \times 10^4$ jNPs/MB) (FIG. 3A) and studied results by FACS. In contrast to control non-fluorescent MBs (FIG. 3C—left panel), increasing %-MB surface coverage—1%, 10% (data not shown) and 50%—led to increasing levels of fluorescent jNP-DNA-MBs (80%, 97%, 99%), respectively, p<0.0001 (FIG. 3C). Concordantly, FACS side-scatter analysis showed dose-dependent increases in jNP-MB granularity (FIG. 8B). For all subsequent experiments, $10^4$ jNPs/MB were used (10%—coverage), which would project to 97% of the MBs associated with jNPs.

jNP-MBs In Vitro Multifunctionality

Figure 3D:
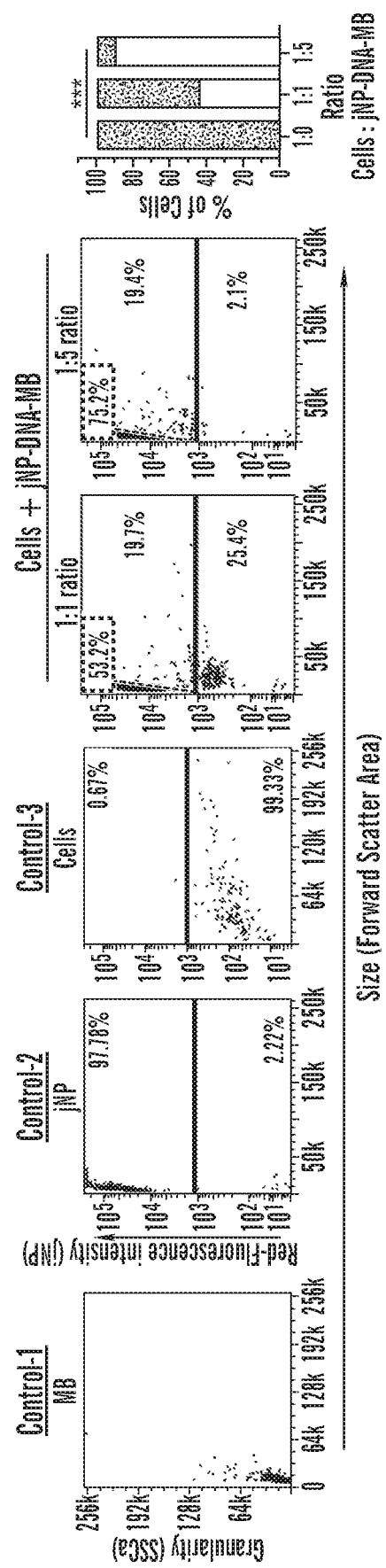
Figure 3E:
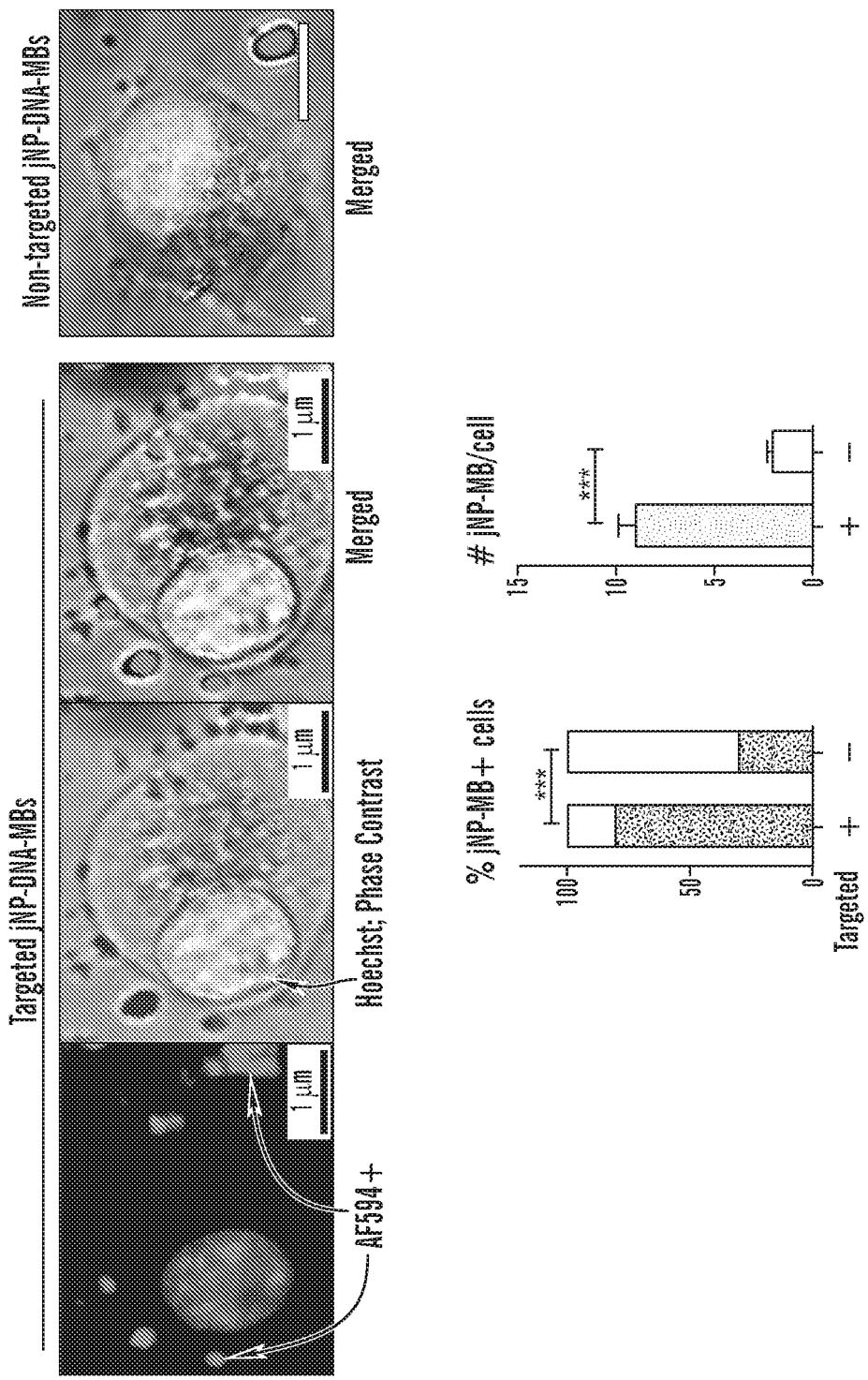

FACS was then used to test targeting functionality of jNPs prepared with AF594-fluorescent-labeled monoclonal antibody against the dual endothelin1/VEGFsp receptor (DEspR), a cell-surface receptor increased on tumor vascular endothelium and tumor cells.[34] Fluorescently labeled targeted jNP-DNA-MBs were prepared, using $10^{12}$ jNPs, 30 μg DNA, and $10^8$ MBs (~10% jNP-coverage of MBs), and binding to DEspR-positive human pancreatic cancer (Panc1)-cells[34] was tested in vitro. Panc1-cells gained fluorescence upon binding of fluorescently labeled targeted jNP-DNA-MBs in a dose-dependent manner, in contrast to non-fluorescent MBs and cells alone (FIG. 3D). Notably, 1:1 jNP-MB-to-cell ratio resulted in ~40% binding of total Panc1 cells, whereas a 5:1 ratio resulted in ~90% binding of total cells, p<0.0001 (FIG. 3D). Microscopy confirmed fluorescent targeted jNP-DNA-MBs bind significantly more (80%) of Panc1 cells compared to non-targeted jNP-DNA-MBs (30%), p<0.0001 (FIG. 3E). Similarly, significantly more targeted than non-targeted jNP-DNA-MBs bound to a given cell, p=0.006 (FIG. 3E).

It was next investigated whether targeted jNP-DNA-MBs can deliver RFP-minigene DNA into DEspR-positive Panc1-cells by sonoporation more efficiently than multiple controls. Cells were incubated with test and pertinent control constructs (FIG. 23), unattached jNP-MBs or MBs were removed after 45 min through media change, and sonoporation was performed to test delivery of DNA-payloads.

Figure 4E:
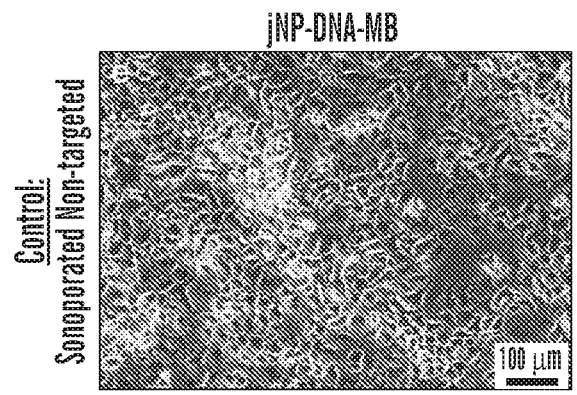
Figure 4F:
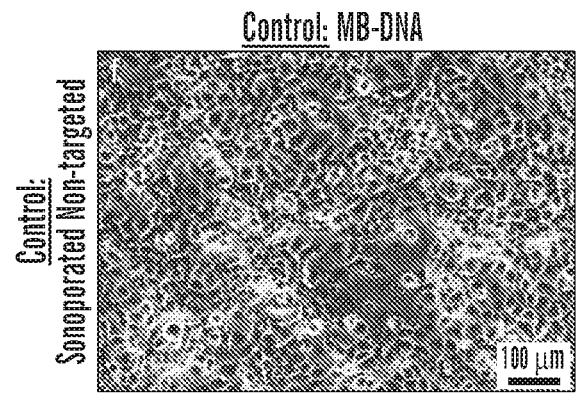
Figure 4G:
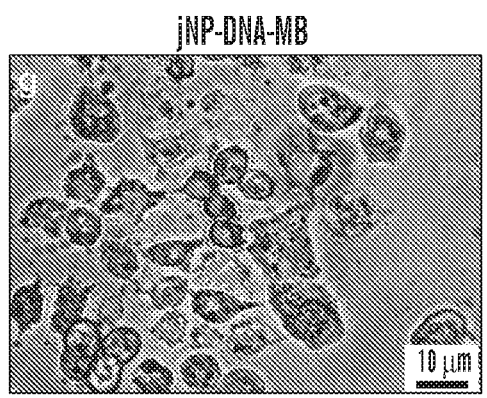
Figure 4H:
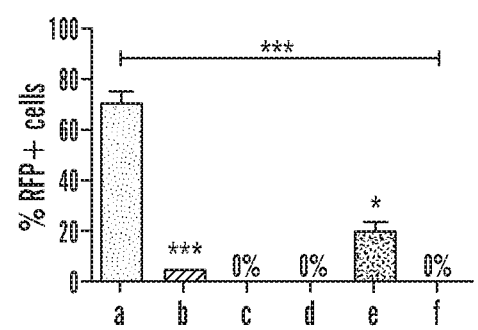
Figure 13:
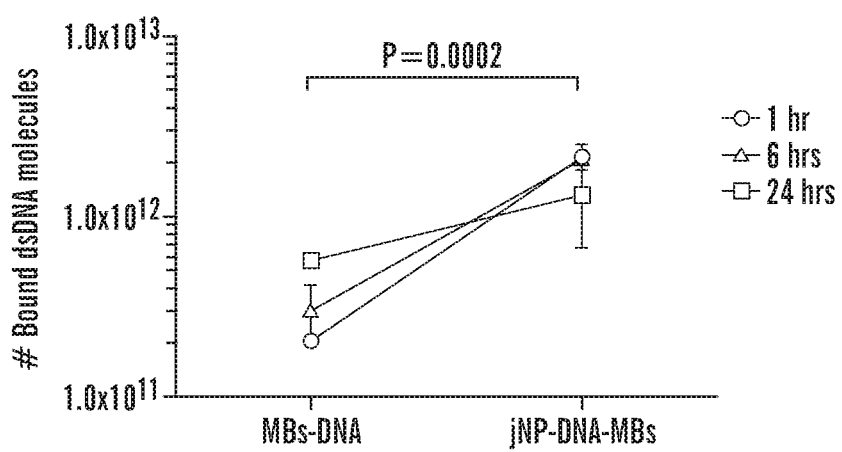
FIG. 13 Analysis of the amount of double strand (ds) plasmid DNA payload (4707 bp-long plasmid dsDNA) assembled into MBs-DNA compared with payload amount assembled into jNP-DNA-MBs. At 1 hr, 6-hrs, and 24-hrs, jNP-DNA-MBs had significantly more dsDNA payload (up to 9-fold, 6-fold and 2-fold greater at 1-, 6- and 24-hours) than the amount incorporated into MBs-DNA, P<0.0013, two-way ANOVA (time×delivery system), showing that significant variation is due to the delivery system MBs-DNA vs jNP-DNA-MBs, and not due to time. Identical dsDNA and MB (MicroMarker Visual Sonics Inc) stocks were used. It is noted that at 1 and 6 hours after assembly of jNP-DNA-MBs, the DNA payload contains $\geq 10^4$ dsDNA molecules per MB in jNP-DNA-MBs. This suggests that jNPs have an increased DNA payload by 9-fold at 1 hour compared to MBs-DNA. However, we also note that although MBs-DNA have less DNA bound than jNP-DNA-MBs, we detect $\geq 10^{11}$ DNA molecules in $10^8$ MBs, or $10^3$ DNA molecules per MB in MBs-DNA FIGS. 14A-14B Comparative analysis of in vivo fluorescence imaging by IVIS.

After 48-hours, fluorescence microscopy showed that Panc1-cells sonoporated with targeted jNP-DNA-MBs exhibit significantly more fluorescence (index of successful delivery of functionally intact red fluorescent protein (RFP)-DNA and subsequent RFP-expression) (FIG. 4A) than those sonoporated with non-targeted jNP-DNA-MBs (FIG. 4B), targeted MB-DNA (FIG. 4E), or non-targeted MB-DNA (FIG. 4F). Non-sonoporated cells exhibit little, if any, red fluorescence (FIG. 4C, 4D). High magnification confirms intracellular location of fluorescence (FIG. 4G). Quantitative analysis detects significant differences (FIG. 4H), confirming advantages of jNP-DNA-MBs as a DNA-delivery system via sonoporation. This is further supported by detection of 10- and 7-fold greater DNA payloads carried by jNP-DNA-MBs compared with the parent MBs at 1- and 6-hours of self-assembly respectively (FIG. 13).

jNP In Vivo Diagnostic Multifunctionalities

Figure 5A:
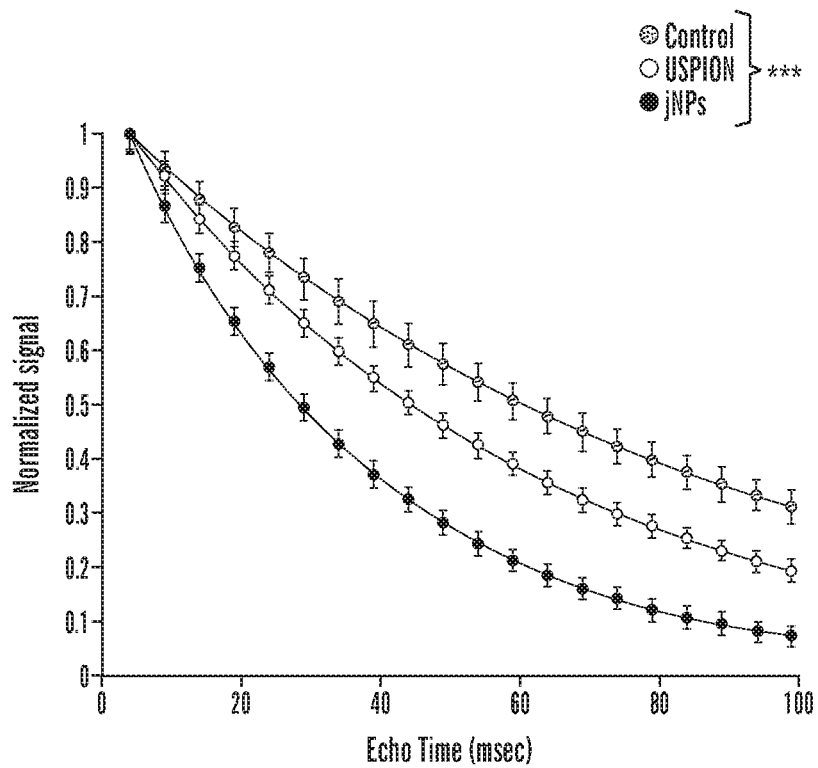
FIGS. 5A-5E Analysis of jNP diagnostic functionality for contrast-enhanced MR- and ultrasound imaging.
Figure 5B:
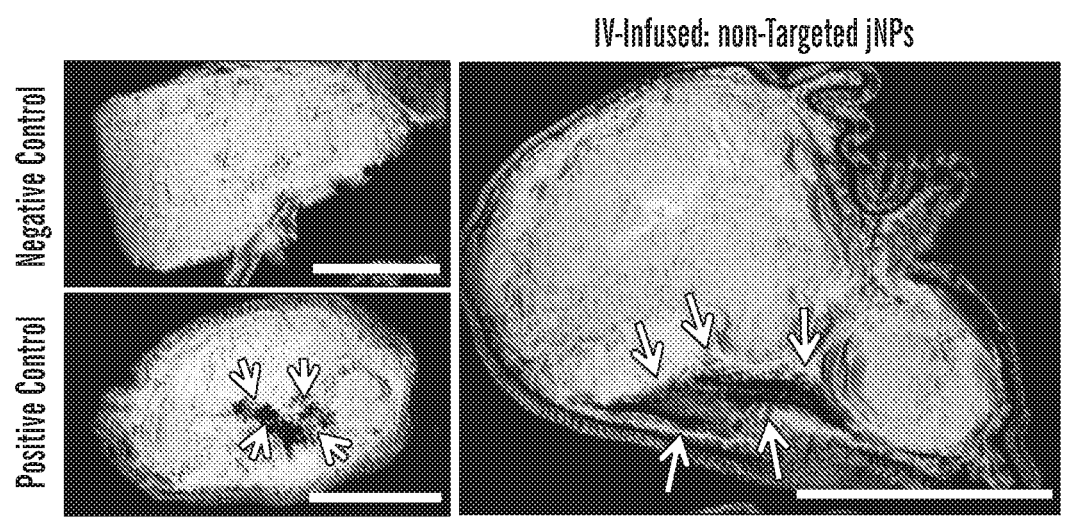
Figure 9:
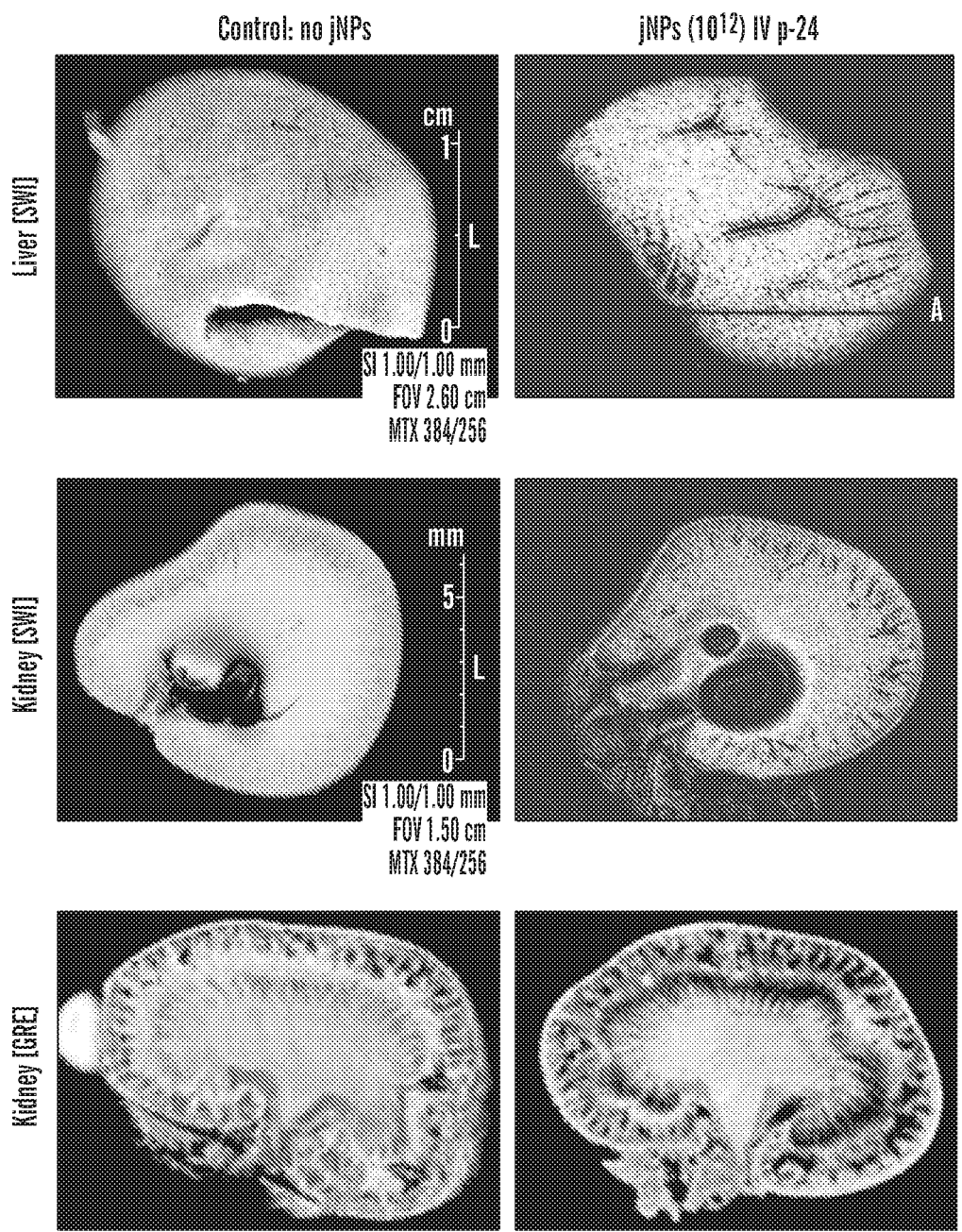
FIG. 9 Representative MR-imaging of liver and kidney comparing control rats (no jNPs infused) and test rats ($10^{12}$ jNPs/rat or 5 ng Fe/rat) 24 hours after IV infusion. Ex vivo 11.7T MR-susceptibility weighted images (SWI) of liver and kidney from xenograft tumor rats show differential hypointensities in the liver and kidney consistent with defined anatomical structures rather than confluent areas of hypointensities seen in xenograft tumors (FIG. 5B). Ex vivo 9.4T gradient echo (GRE) MR-images of control and test normal rat kidneys confirms T2*-MR hypointensities in jNP-infused rat kidney but not in the renal pelvis. Comparison of liver and kidney MR-images indicate hepatic clearance but not kidney excretion. MR-images were obtained with organs placed in fomblin. Determination of histological correlates needs to be studied FIG. 10 Schematic diagram of targeted ultrasound contrast-enhanced imaging. Infused ultrasound contrast agent microbubbles (MBs) are confirmed at approximately 1 minute from bolus infusion (t–1 min) with increased contrast intensity signals (CIS) filling the blood vessel lumen. After 5 min (t–5 min), clearance of unbound "free" MBs is documented with decrease in contrast intensity (dashed line). At t–20 min, only adherent receptor targeted-MBs remain and impart contrast-intensity signals detected for targeted jNP[DNA]MBs, and for targeted non jNP[DNA] MBs. To show that increased contrast intensity signals are indeed from attached 'endothelial receptor-targeted' MBs, a high-intensity ultrasound (US) destruct sequence is done at approximately t–21 min, disrupting microbubbles as detected by a drop in CIS from release of MB-gas. Based on blood vessel size, run-off of MB-gas in the circulation can present as either a steep drop in CIS levels (fast runoff), as seen in larger blood vessels, or a sloping decline in CIS levels, as seen in lower flow microvessels, or with slower degradation of MBs. The sequence of imaging-destruction-imaging can be repeated multiple times in different tumor areas (e.g., at t–10, 20, 25, 30-min) depending on stability of the antibody-receptor interaction. jNP, Janus nanoparticle; MB, microbubbles; min, minutes; std, standard; t, timepoint; , microbubbles; , disrupted MBs after ultrasound destruct sequence; US, ultrasound.

Given the USPION core and ability of jNPs to assemble with echogenic MBs, jNPs were tested for dual modality contrast-enhanced magnetic resonance (MR)-imaging and ultrasound molecular imaging. For MR-contrast-imaging, it was first determined that jNPs exhibit shorter T2*-relaxivity compared with precursor-USPIONs and control blanks across a range of 10-100 milliseconds echo times, P<0.001 (FIG. 5A). An in vivo test was next conducted to determine whether jNPs localize to tumors by tumor-selective enhanced permeability and retention (EPR) effects and provide contrast-enhanced MR-imaging. Compared to control tumors receiving no jNPs, tumors injected intra-tumorally ex vivo with ~50 µl of jNPs [$10^{12}$/ml] as a positive control exhibited significant MR-T2*-hypointensity. Similar results were seen in tumors from rats infused with $10^{12}$ jNPs; these tumors exhibited MR-T2*-hypointensity confluent 'regions-of interest' [(ROI)~60 mm$^2$] with scattered intratumoral hypointensities (FIG. 5B). It was also found that contrast-enhanced imaging is better at 24-hr (FIG. 5B) compared with 1- and 4-hr after infusion (data not shown). Because non-targeted jNPs were used to test universal MR-imaging of tumors, the MR-T2*-hypointensity ROIs detected only in tumors and not in liver or kidney (FIG. 9) suggest jNP tumor-localization via EPR-effects, a known time-dependent and tumor-selective characteristic requiring exposure to a contrast reagent for more than 6-hrs at a high plasma concentration[35]. In contrast, MR-T2*-hypointensities in the liver at 24-hrs exhibit structural patterns consistent with clearance via the hepatic Mononuclear Phagocyte System, as expected (FIG. 9). Likewise, detection of MR-T2*-hypointensities with anatomical structural features in the kidney cortex but not in the renal medulla or pelvis (FIG. 9) indicate jNP-presence in the microvascular space and non-clearance through the kidney. This is consistent with observations that kidney clearance occurs only for nanoparticle sizes <6 nm$^{36}$.

Figure 5C:
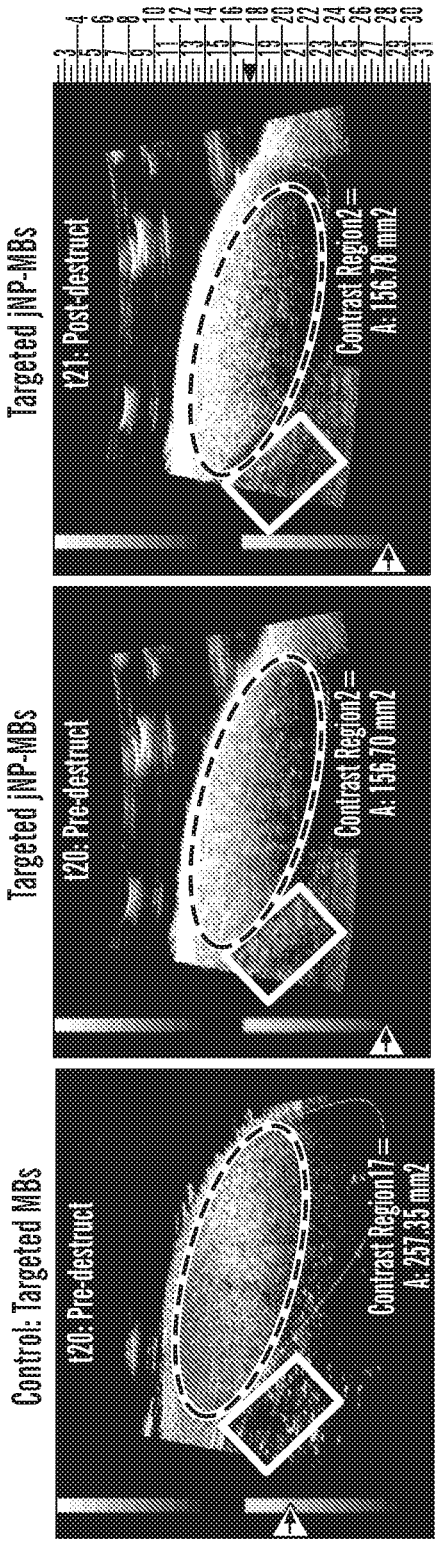
Figure 5D:
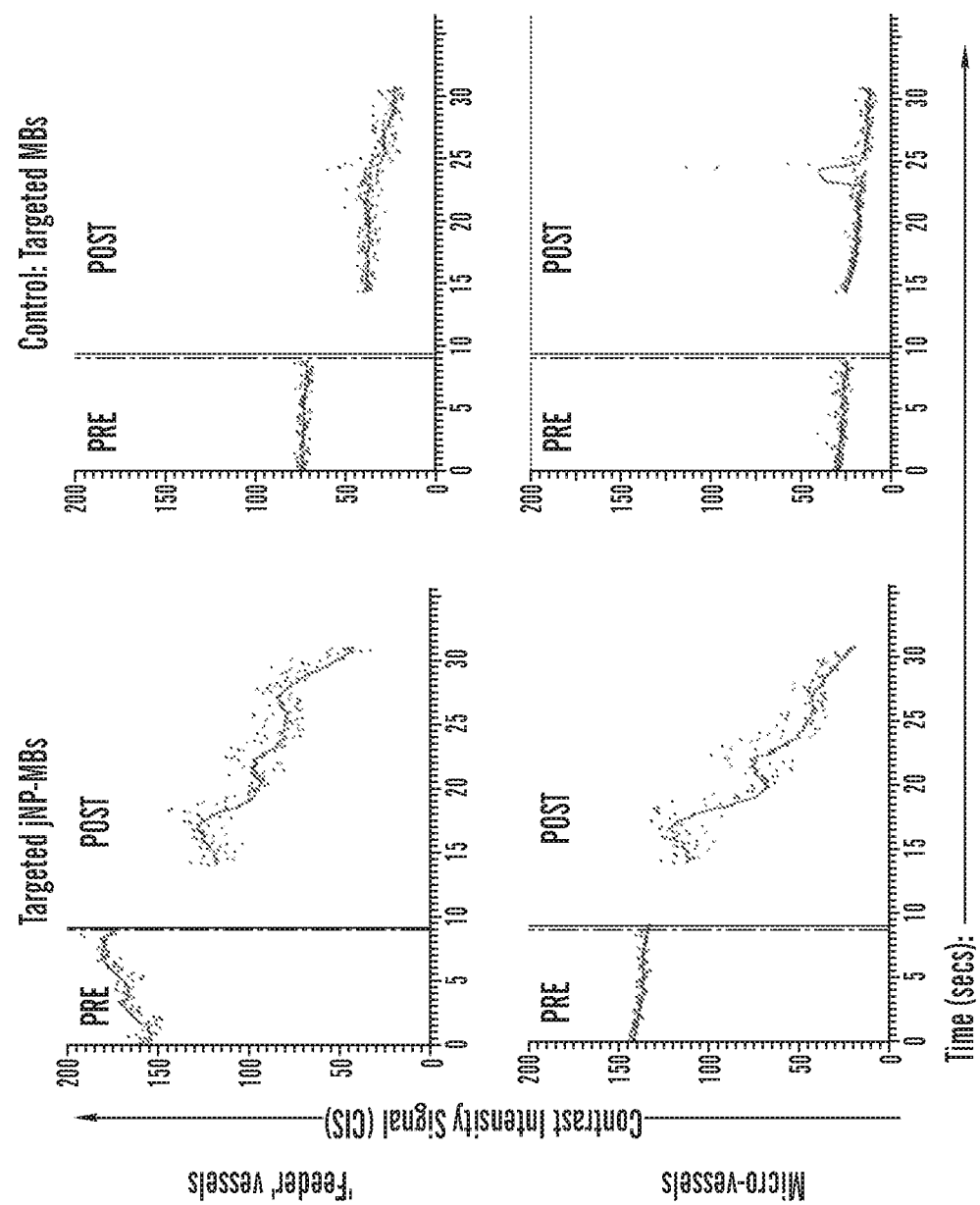
Figure 5E:
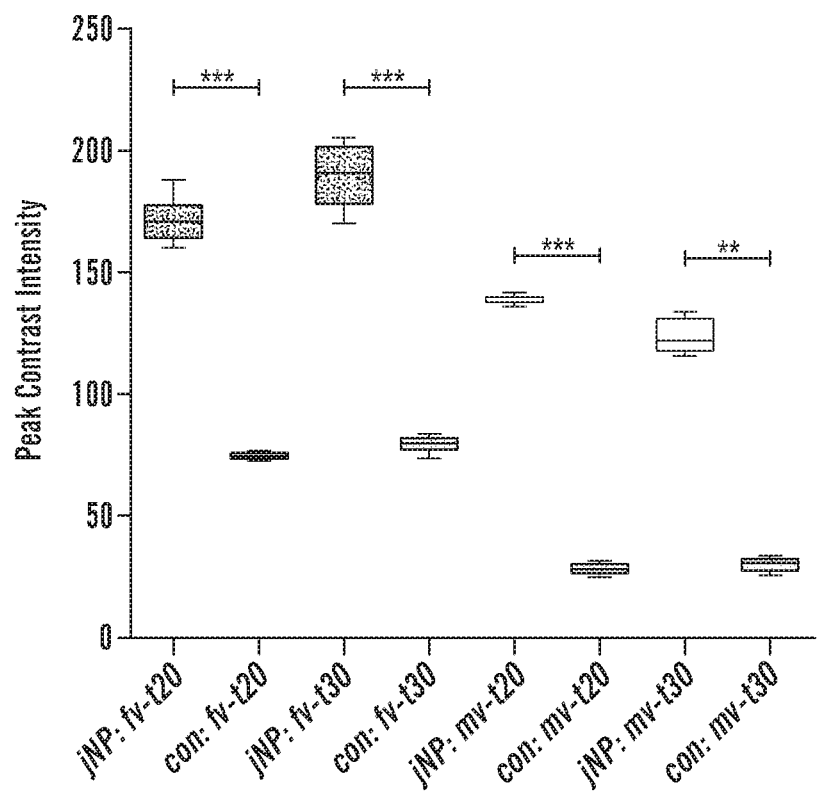
Figure 10:
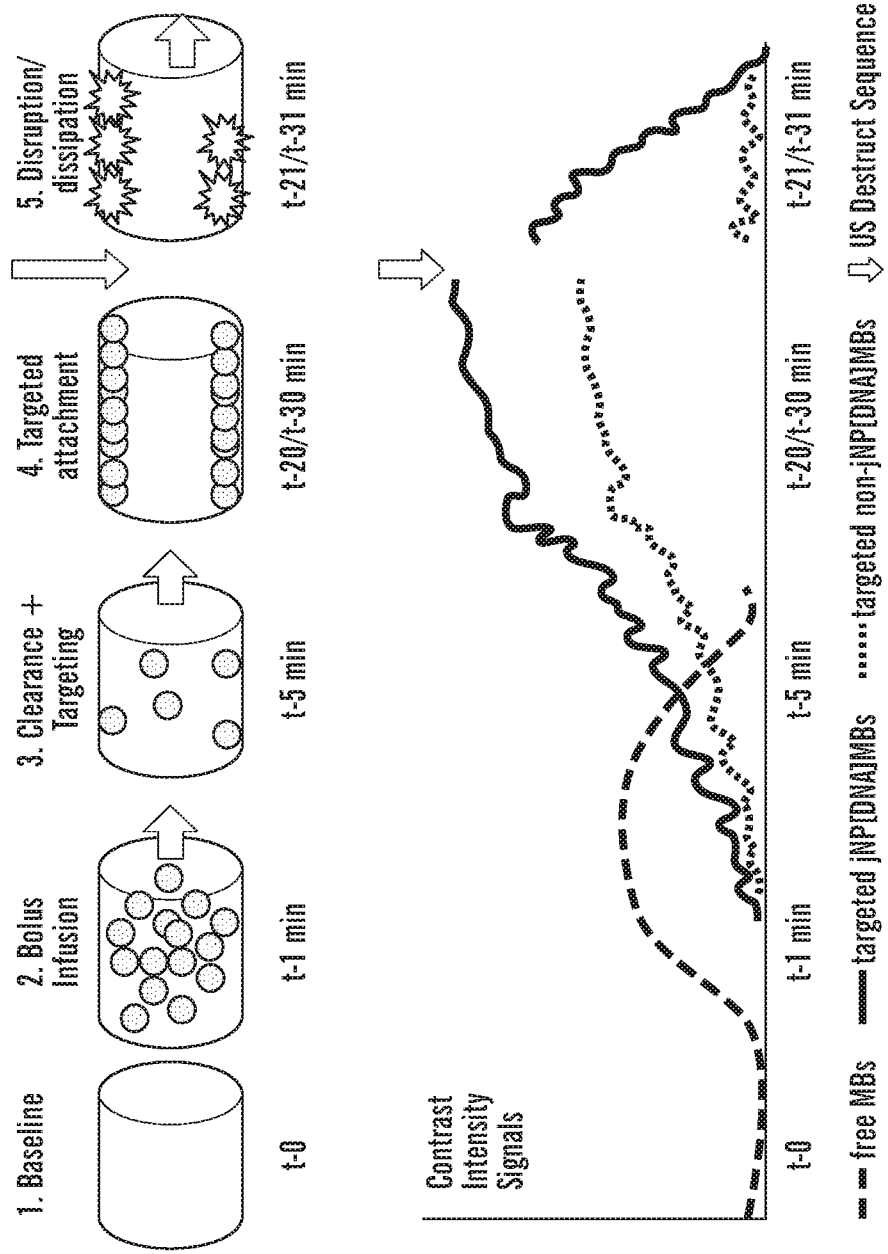
Figure 11B:
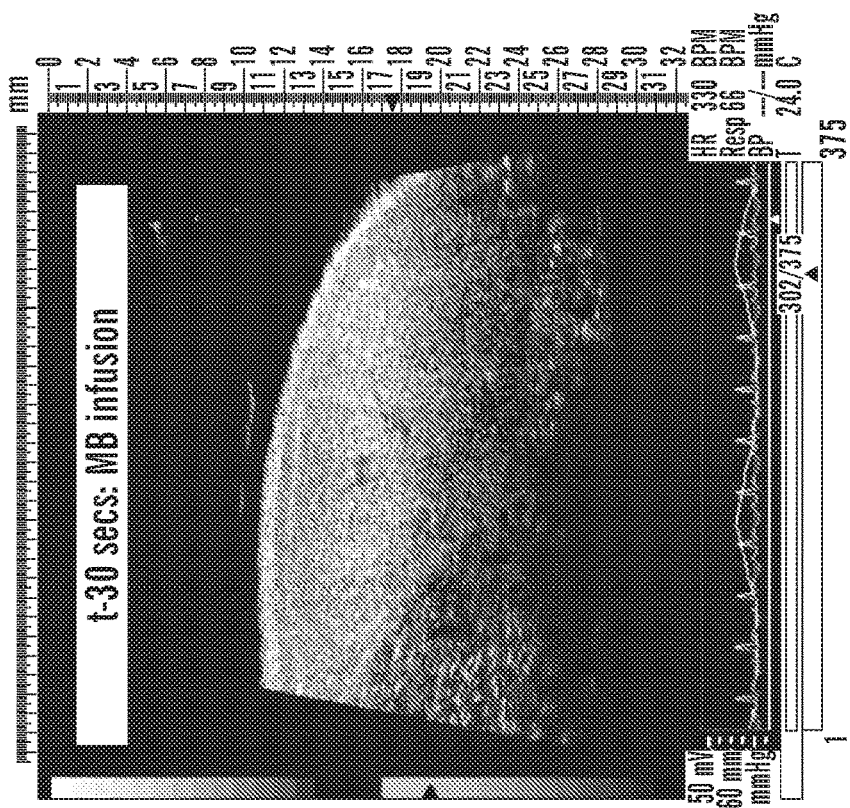
FIGS. 11A-11F Representative ultrasound images of spontaneous mammary tumors in post-menopausal rats and corresponding contrast intensity signal (CIS) plots of bolus infusion and subsequent contrast-enhanced imaging using DEspR-targeted non jNP MBs.
Figure 11A:
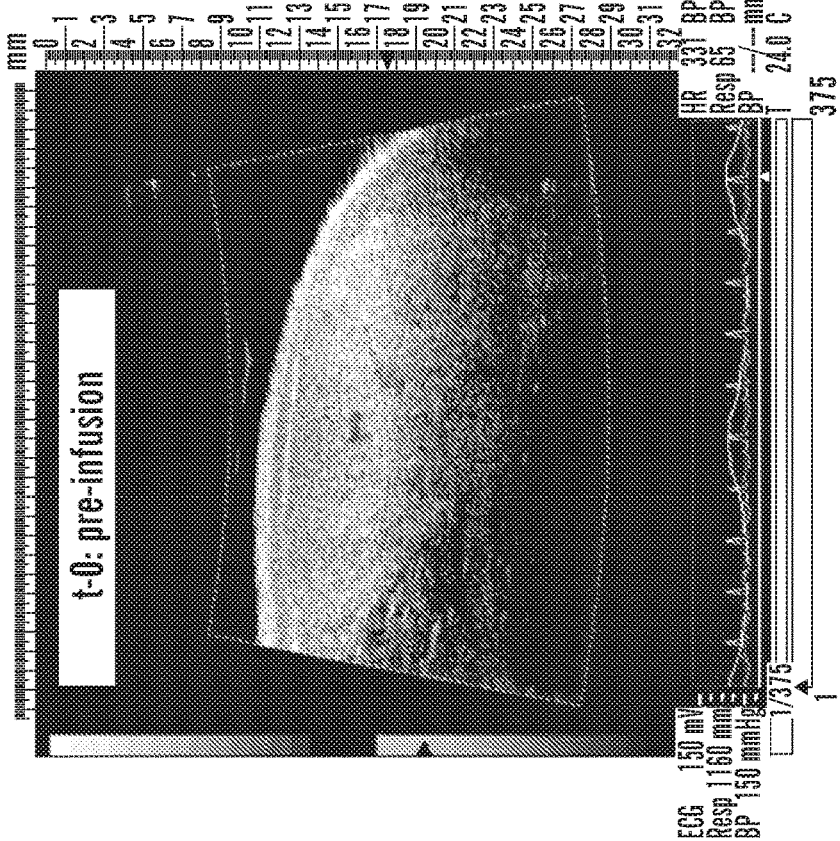
Figure 11C:
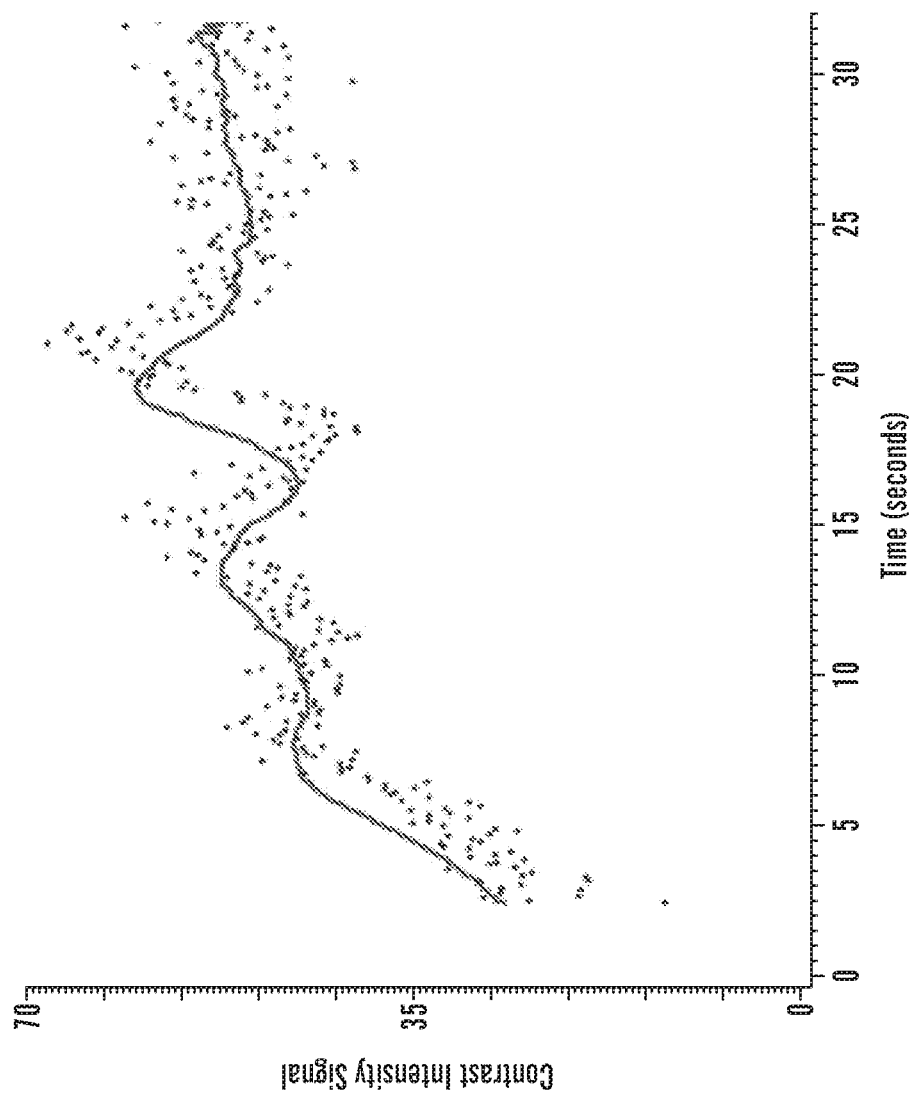
Figures 11D, 11E:
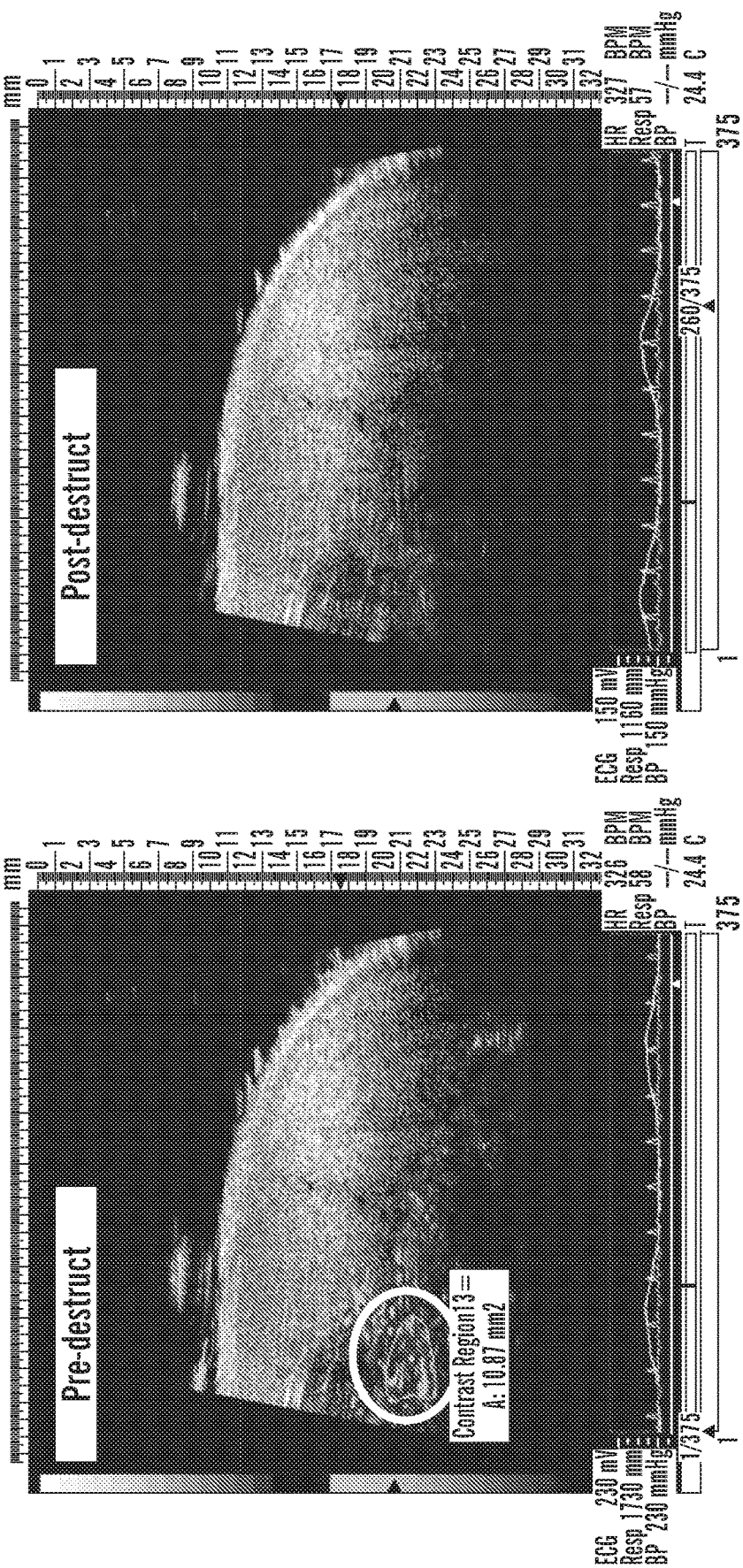
Figure 11F:
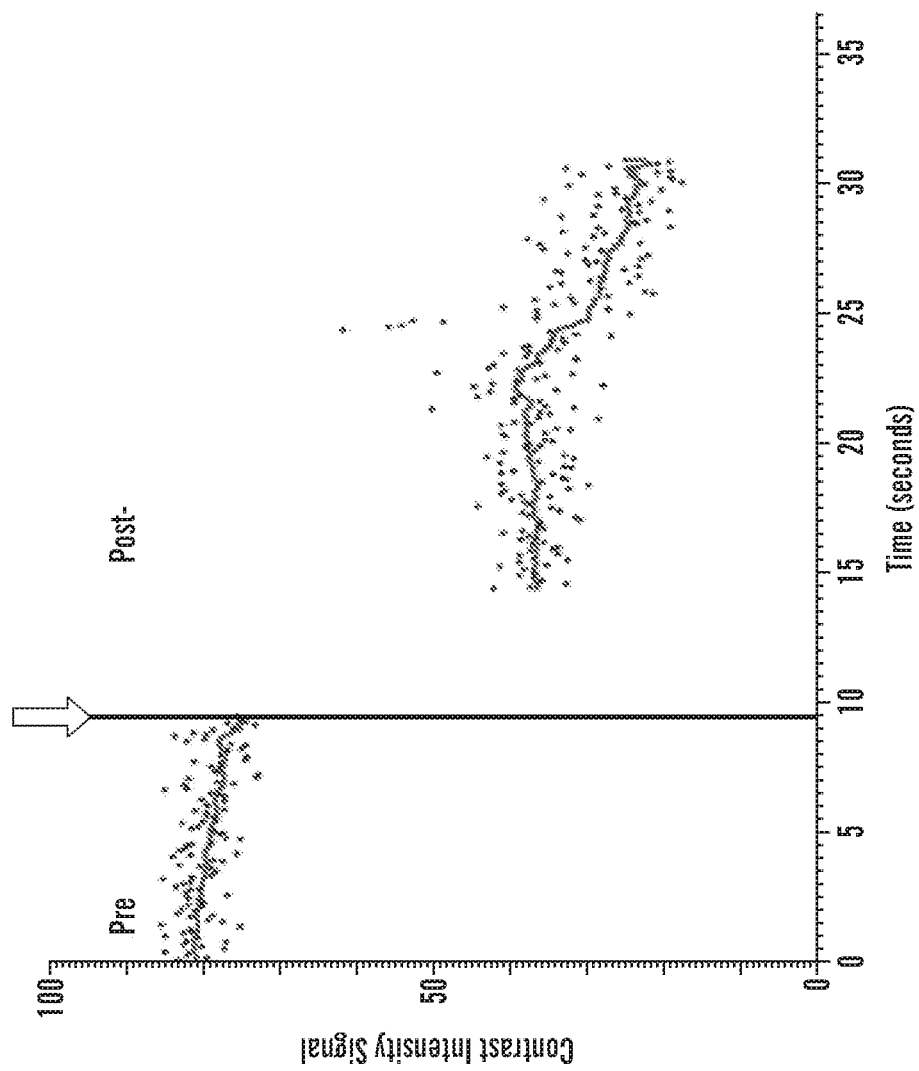
Figure 12:
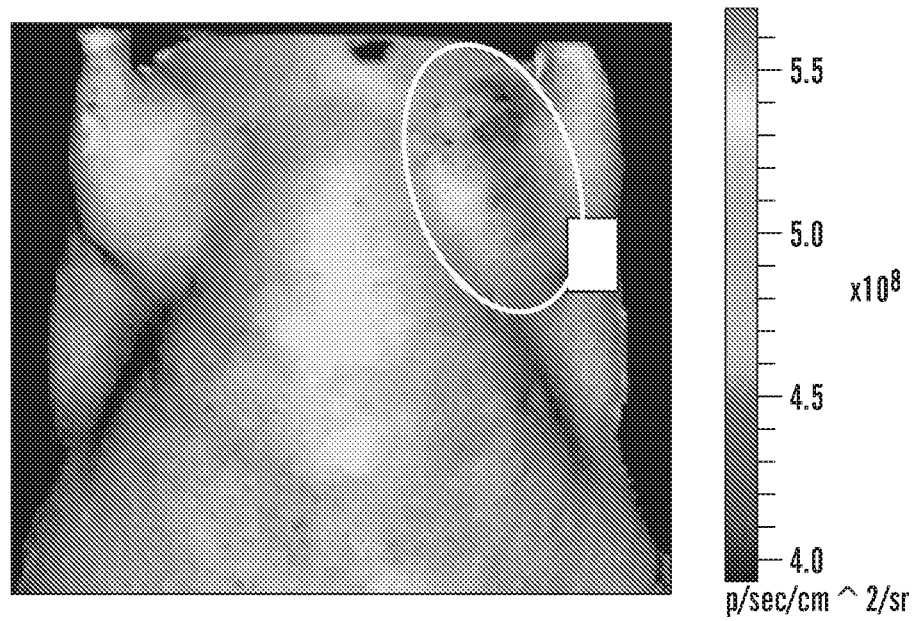
FIG. 12 Baseline imaging of zero-background in vivo fluorescence using IVIS. Zero-fluorescence shown at baseline prior to delivery of red fluorescent protein (RFP) minigene-DNA by sonoporation using jNP[DNA]MB-heteroplexes. Spontaneous mammary tumor in post-menopausal rat encircled in red. Any fluorescence after sonoporation indicates presence of functional red fluorescent protein, which implies that minigene-DNA was delivered intracellularly, transcribed into RNA, and translated into a functional protein that exhibits red-fluorescence.

As a second imaging modality, it was next tested whether targeted jNP-MBs enhance ultrasound molecular imaging of tumor vasculature. For receptor-targeted ultrasound molecular imaging, peak contrast intensity signals (CIS) were measured from successful receptor-targeted/adherent MBs persisting after clearance of freely circulating MBs typically by 5-min,[37] and confirmed that CIS derive from MBs by demonstrating subsequent loss of increased CIS-levels upon operator-triggered MB-destruction (FIG. 10). Compared to targeted MBs (FIG. 5C, left), targeted jNP-MBs exhibited greater contrast-enhanced ultrasound imaging of extratumoral feeder vessels and intratumoral microvessels (FIG. 5C, middle)—confirmed by decreased CIS upon operator-triggered ultrasound destruction of attached MBs (FIG. 5C, right). Analysis of contrast-intensity signal (CIS) time curves showed that targeted jNP-MBs attain 2×-higher peak CIS-levels in feeder vessels and 6×-higher CIS-levels in intratumoral microvessels at t−20 and t−30-min compared to targeted MBs (FIGS. 5D, 5E), and also compared to peak CIS levels after bolus infusion (FIGS. 11A-11F). While jNP-MBs exhibit a slower decline in CIS after ultrasound destruction, CIS levels still reach baseline levels equivalent to control targeted MBs after 15-seconds (FIG. 5D).

jNP In Vivo Delivery Efficacy and Safety Profile

Figure 6A:
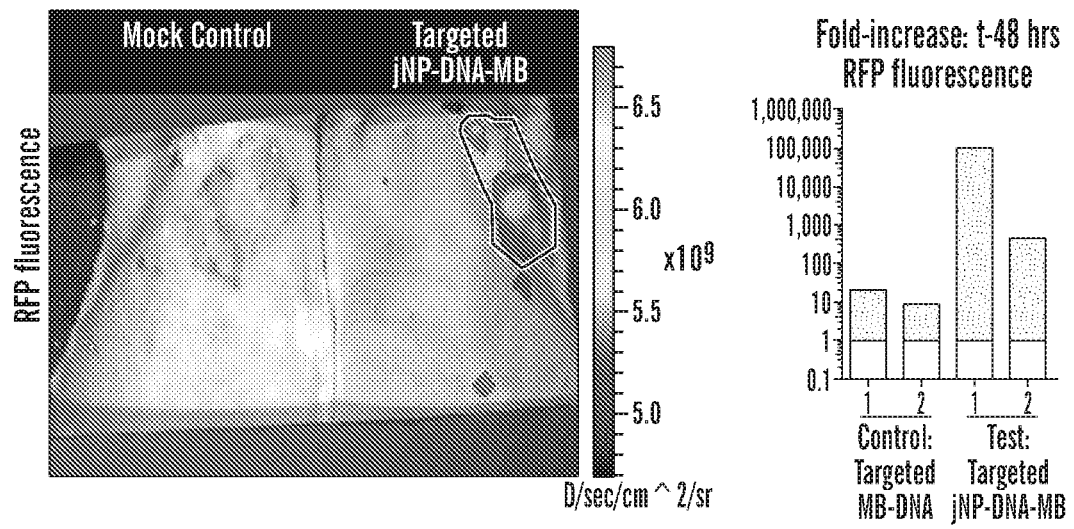
Figure 6B:
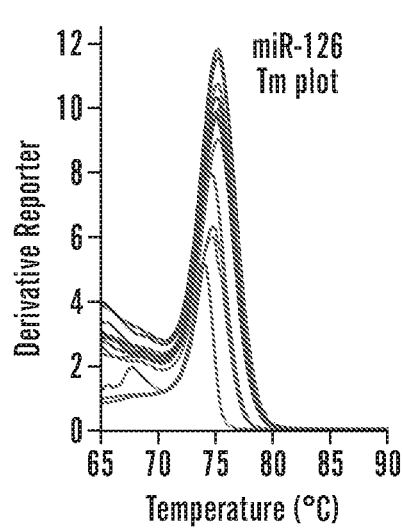
Figure 14A:
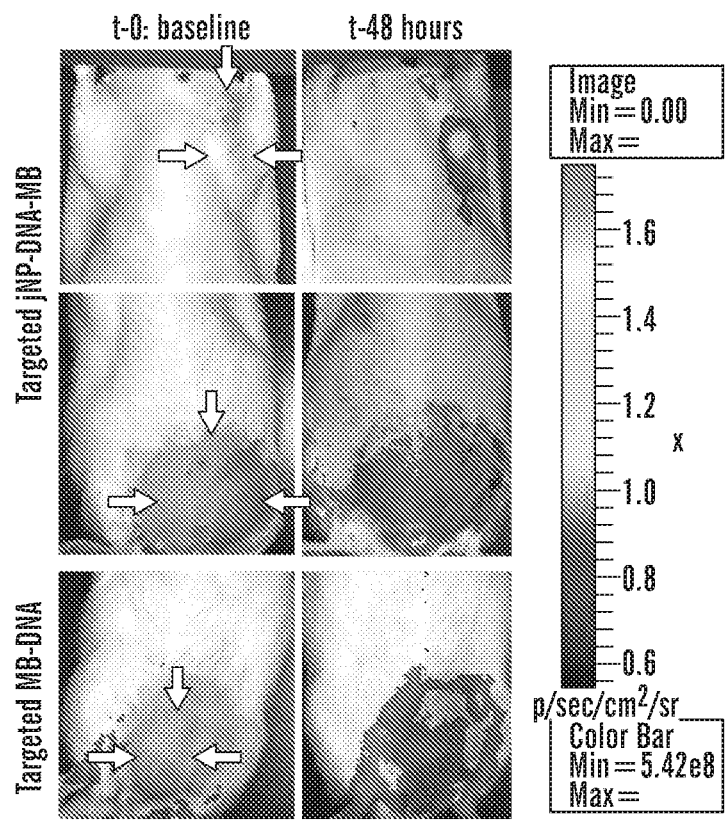
FIG. 14A, Representative in vivo fluorescence images by IVIS at baseline and 48-hours after sonoporation. Zero-fluorescence shown at baseline prior to delivery of red fluorescent protein (RFP) minigene-DNA by sonoporation using targeted jNP-DNA-MBs and targeted MBs-DNA. Spontaneous mammary tumor in post-menopausal rat is designated by red arrows. Color bar scale: 5.42e8 to 1.7 e9 FIG. 14B, Comparative in vivo fluorescence images obtained by IVIS-imaging 48-hours after sonoporation. Sonoporation was done using MBs-DNA immediately after infusion while MBs filled the intravascular space (<5 min) using a SoniGene sonoporator. Identical number of MBs and amount of RFP-DNA, and sonoporation settings were used. Color bar scale: 1176 to 3930.
Figure 14B:
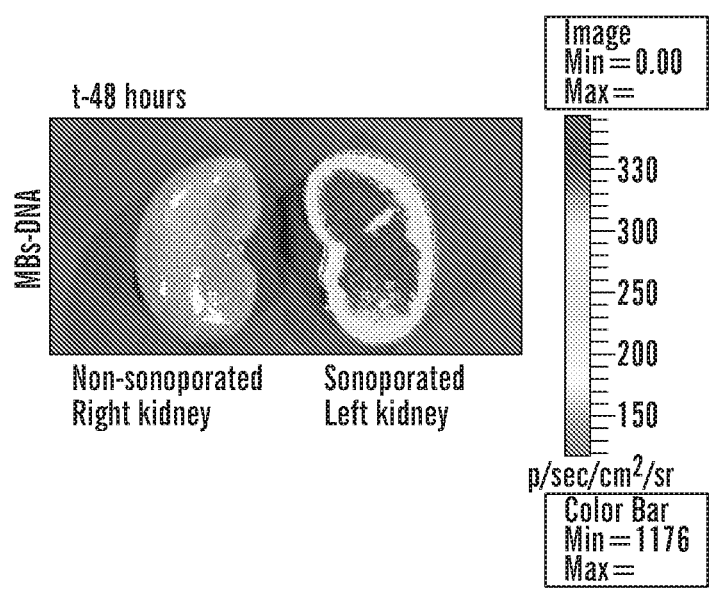

The inventors next investigated in vivo jNP-MB delivery functions for nucleic acid payloads to tumors via sonoporation (FIG. 6), which a priori requires successful target interaction and payload-binding, carrying, release and delivery. After establishing baseline zero-fluorescence (FIG. 14A), sonoporation of tumors with i) targeted RFP-loaded jNP-DNA-MBs [$10^{12}$ jNPs/30 µg DNA/$10^8$ MBs], ii) control targeted RFP-loaded MB-DNA and iii) mock control tumor was performed. Forty-eight hours later, in vivo fluorescence-imaging (IVIS) detected no fluorescence in mock control compared with marked RFP-fluorescence in rat tumors sonoporated with targeted jNP-DNA-MBs (FIG. 6A, FIG. 14a). In vivo RFP-fluorescence obtained with targeted jNP-DNA-MBs was also significantly greater than that attained with control targeted MBs (FIG. 6A bar-graph, FIG. 14a), and non-targeted MBs (FIG. 14B).

Figure 6C:
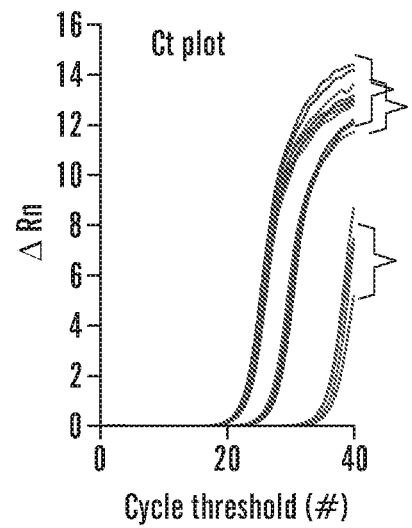

To test modular versatility in payload delivery, it was tested if targeted jNP-MBs could deliver miRNA-126, a tumor suppressor miRNA markedly decreased in human breast and pancreatic cancers. Decreases in miRNA-126 levels contribute to increased KRAS (Kirsten rat sarcoma viral oncogene homologue), which promotes cancer progression, metastasis and tumor-resistance,[38-40] thus successful delivery of functionally active miRNA-126 would be expected to decrease KRAS protein levels. Following procedures used for successful RFP-DNA delivery, miRNA-126 delivery was tested by targeting jNP-MBs to two xenograft tumor models: breast cancer KRAS$^{G13D}$-mutant MDA-MB-231 cancer stem-like cells (CSCs), and pancreatic cancer KRAS$^{G12D}$-mutant Panc1-CSCs. Real-time quantitative reverse transcriptase PCR (real-time qRT-PCR) analysis confirmed specificity of miRNA-126 amplification products (expected ~74.8° C. melting temperature for miRNA-126) (FIG. 6B) and showed >1000-× increase in miRNA-126 levels (P<0.0001) in xenograft breast and pancreatic tumors sonoporated with jNP-miRNA-126-MBs relative to the levels in non-manipulated tumors (FIGS. 6C, 6D). Moreover, delivery of miRNA-126 in these studies resulted in tumor levels similar to normal-high levels of miRNA-126 detected in normal liver and kidney tissues (FIG. 6D). In contrast, delivery of 4-fold lower dose of miRNA did not work in identical conditions (data not shown), indicating that dosing is important and delivery-specific.

To validate delivery of functionally intact miRNA-126, Western blot analyses of KRAS, a key target gene for miRNA-126, were performed. Notably, KRAS-levels were decreased up to 2.8-fold in xenograft breast tumors (FIG. 6E), indicating functional association of delivered miRNA-126 with RNA-induced silencing complex (RISC), a prerequisite for inhibition of target gene translation. Variation in extent of KRAS-decrease among tumors with delivered miRNA-126 observed in xenograft Panc1 tumors and breast tumors (data not shown) indicate need for further study, along with analysis of other downstream targets and off-target effects.

Figure 15A:
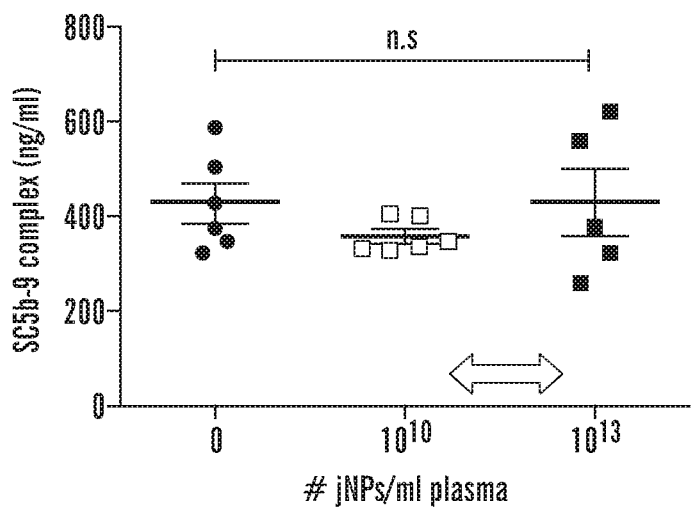
FIGS. 15A-15B In vitro analysis of Terminal Complement Complex (Sc5b-9) levels in plasma with and without jNPs.
Figure 15B:
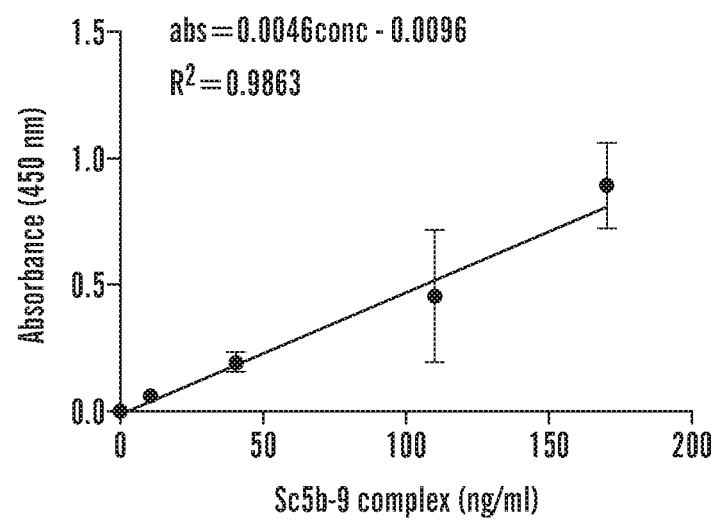
Figure 16B:
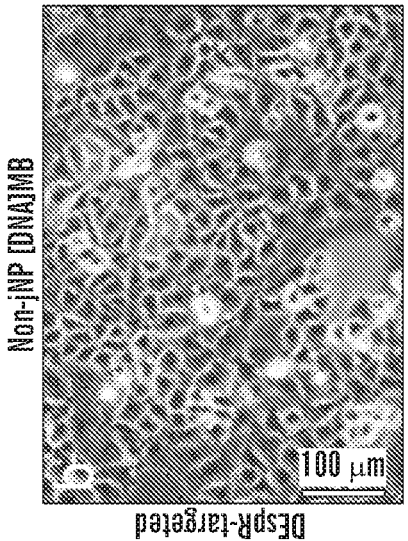
FIGS. 16A-16D Demonstration that jNPs can be targeted with different antibody targeting moieties using the same covalent-layering methodology and function to deliver reporter function DNA (RFP-minigene construct) by sonoporation in vitro to Panc1 tumor cells.
Figure 16A:
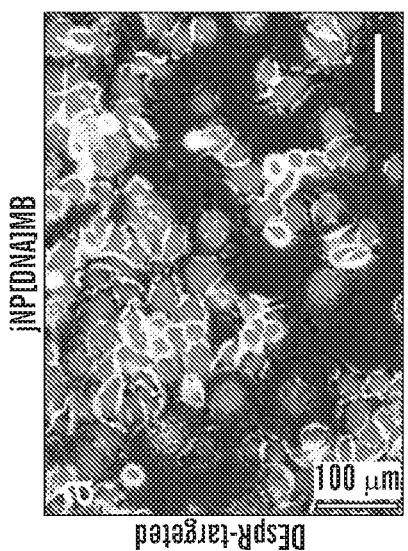
Figure 16C:
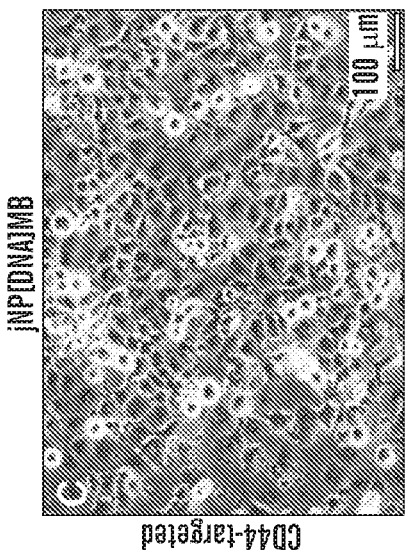
Figure 16D:
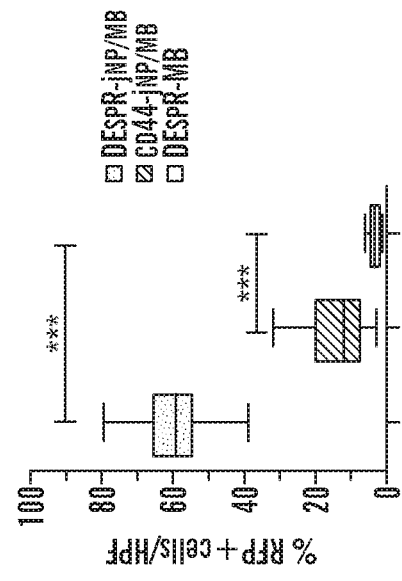

To assess in vivo safety of jNPs and jNP-MBs, daily monitoring was performed on all tumor model rats infused with $10^{12}$ jNPs or jNP-MBs, as well as hypertensive stroke-prone rats infused with $10^{12}$-jNPs, and normal rats infused with $10^{-13}$-jNPs. No adverse events were observed acutely or up to 2-weeks. Additionally, measurements of plasma levels of cytokines/chemokines two-weeks after infusion of $10^{12}$ and $10^{13}$ jNPs, respectively, in stroke-prone and normal rats showed that jNPs do not induce inflammation, endothelial activation or complement activation compared with control rats (FIG. 6F). Concordantly, in vitro analysis for SC5b-9, the complement activation end-product regardless of activation mechanism, corroborated non-activation of complement system by jNPs in vivo (FIG. 15). These data contrast with toxicities reported in studies using larger lipopolyplexes[42] and other SPIO MR-contrast agents for tumor imaging[24], but are similar to observed in vivo safety of LINEAR-PEI$_{25K}$ polyplexes in mice.[42]

In contrast to previously reported Janus nanoparticles, all larger than 100 nm,[12-17] covalently layered ultrasmall jNPs reported here exhibit modularity and multifunctionality that offer key advantages: efficient and safe delivery of nucleic acid therapies and dual-mode imaging of tumor-specific features. Attaining 10-fold greater reporter-gene fluorescence compared to MBs, the jNP-MB nucleic acid delivery system uses 6-fold less payload (~30 µg/rat) and 10-fold fewer microbubbles ($10^8$-MBs/rat) compared to recent mouse studies (200 µg DNA/mouse and $10^9$ MBs/mouse,[44] or 500 µg DNA/mouse and $10^8$ MBs/mouse)[7] despite rats being ~5-10-fold heavier than mice. Thus, our system is hundreds-fold more efficient than systems used in published mouse studies. This efficiency is likely attributable at least in part to stable DNA-binding by jNPs and 10-fold greater payloads in jNP-MBs compared with MBs. The advantage of jNP-MBs is further demonstrated by observations that jNP-MBs attain DEspR-positive molecular imaging of intra-tumoral vessels compared to minimal detection by MBs despite their identical targeting moiety, and attain effective DEspR-targeted delivery of both DNA and miRNA-payloads at clinically safe ultrasound energies, 153 kPa. The low acoustic energy requirement is also a distinct advantage over polymer microbubbles that typically require higher energy.

In vivo RFP-fluorescence detection and decreased KRAS protein levels demonstrate delivery of functionally intact DNA and miRNA that are properly processed by the cell. These data validate cytosolic delivery by jNP-MB sonoporation as a highly efficient, endosomal-independent[6,45] delivery paradigm, thereby avoiding cellular toxicity associated with intra-endosomal inflammatory pathways reported for PEI-DNA/siRNA nano-polyplexes.[46] Because targeted jNP-MB sonoporation can potentially overcome limitations of passive delivery systems relying on EPR[16,49] and subsequent endocytic-uptake and escape,[50] this system has the potential to restore the reduced tumor suppressor miRNA levels often associated with cancer aggressiveness (e.g. miRNA-126).[38]

Contrast-enhanced MR-imaging of tumor-specific EPR-sites indicates the hypothesis that hemispherical segregation of payload—from targeting-face in jNP-design is key. Notably, using $10^{12}$-jNPs/rat or 0.05 lag Fe/kg dose is $10^3$- to $10^4$-fold less than clinically approved human doses for Resovist™ (60 nm, 90 µg Fe/kg) and Ferridex™ (120-180 nm, 560 µg Fe/kg), respectively. Better contrast-enhanced MR-imaging at 24-hours compared with 4-hours indicate jNP circulation at high levels beyond 6-hours since a minimum 6-hours is required for MR-imaging of tumor-selective EPR-effects.[35]

Although formal toxicity studies are needed prior to clinical translation, the initial safety profile show that jNPs do not trigger adverse events, inflammation or complement activation, which contrasts reported acute adverse events for PEI-DNA/siRNA nano-polyplexes,[10,46-47] and 500-× higher cytokine levels for free linear[25-kDa]-PEI in culture.[48] Altogether, these data indicate that the nano-design is safe and effective for use of linear-PEI$_{25kDa}$, at a maximum 10 µg PEI in $10^{12}$ jNPs/dose. Without wishing to be bound by theory, it is hypothesized that the observed 'inflammation/complement-stealth' property is due to the antibody targeting-face design that allows for IgG-like long circulation times using targeting-antibody isotypes with insignificant ADCC and CDC for targeted jNPs, or non-specific antibodies that do not engage antigen for non-targeted jNPs.[41]

In summary, jNP theranostic multifunctionality, relative structural stability, sufficient circulation time, and initial safety profiles collectively are indicative of a balanced efficacy/safety ratio, thus providing proof-of-concept that jNPs and jNP-MBs comprise an ideal theranostic nanosystem for cancer.

Example 2: Exemplary Methods & Materials

Preparation of Janus Nanoparticles (jNP).

Ultrasmall superparamagnetic iron oxide nanoparticles[52] were assembled through covalent coupling of sequential layers. Monodisperse citric acid-coated $Fe_3O_4$ USPIONs (~10-nm in diameter) were functionalized to have a 4:1 PEG$_{2K/3.4K-NH2}$ mixed brush as previously described[53]. A modified "layer-by-layer" technique[54,55] was used to prepare asymmetrically functionalized jNPs—resulting in nanoparticles with cationic PEI on one face, and a targeting monoclonal antibody (mAb) moiety (anti-DEspR mAb[37]) on the opposite face. Non-targeted jNPs are prepared using isotype IgG2 or non-specific IgG antibodies (Pierce Thermo Scientific™, Rockford, Ill.) for the antibody-face. Stepwise layering was documented by changes in zeta potential or gain of fluorescence. To prepare fluorescently labeled jNPs for heteroplex assembly studies, the inventors used antibodies labeled either with red-fluorescent AF594 (jNP$^{AF594}$) or with AF568 (jNP$^{AF568}$) for the targeting-face.

In Vitro Characterization of jNPs.

Cryo-transmission electron microscopy (cryo-TEM) was performed to visualize jNPs using a CM12 Transmission Electron Microscope (Philips Electron Optics™, Eindhoven, Netherlands). AFM was performed on jNPs. Determination of jNP diameters by DLS was performed per manufacturer's specifications. Study of jNP binding to DNA-payload was done via ethidium bromide (EtBr) dye exclusion assay as described,[35] with jNPs and DNA mixed prior to addition of EtBr, and via EtBr dye displacement assay[36] with DNA and EtBr mixed first in a 4:1 ratio, followed by addition of jNPs. Dose-response was done with increasing number of jNPs using different DNA concentrations.

Assembly and Analysis of jNP[DNA]MB-Heteroplexes.

Stepwise assembly of the jNP[DNA]MB heteroplex is done in physiological saline at room temperature with mild rotation. For heteroplex assembly, the inventors used commercially available ~2-µm diameter microbubbles (Micro-Markers™, Visual Sonics-Fuji™, Canada) characterized for acoustic properties and successful delivery of DNA[44,56]. The inventors used the following formulation: $10^8$ MBs, 30-µg RFP-minigene DNA as nucleic acid payload, and $10^{12}$ jNPs for projected 10% coverage of $10^8$ MBs, or $10^4$ jNPs/MB. Gain of fluorescence marks assembly and cell-targeting endpoints as tracked by FACS analysis using fluorescently labeled DEspR-targeted jNP$^{AF594}$. FACS analysis was used to quantify dual-labeled heteroplex assembly to show binding of DNA to MBs, and jNP binding to [DNA]MBs after 1- and 24-hr, using differential fluorescent labeling of nucleic acid payload: oligoDNA$^{AF468}$ (Integrated DNA Technologies™, Coralville, Iowa), and jNPs$^{AF568}$.

In Vitro Analysis of jNP[DNA]MB-Heteroplex Multifunctionality.

Targeting and stable binding of DEspR-targeted jNP [DNA]MB heteroplexes to Panc1 cancer cells is documented in vitro by FACS analysis and confocal fluorescence microscopy fluorescently labeled jNPsAF594. In vitro delivery of red fluorescent protein (RFP) mini-gene DNA was done by sonoporation and gene expression assessed by confocal microscopy in vitro. Quantitation was done on 12-16 high power fields from 8 independent sonoporation sites per study group (n=8).

In Vivo Analysis of jNPs and jNP[DNA]MB-Heteroplex Multifunctionality.

In vivo tests of jNP[DNA]MB-heteroplexes were done using identical component ratios validated in vitro for heteroplex assembly. Three rat tumor models were used: spontaneous mammary tumors in post-menopausal female rats for ultrasound contrast-enhanced molecular imaging and for DNA delivery; nude rat heterotopic, xenograft tumor models of human pancreatic cancer (Panc1) and breast cancer (MDA-MB-231) developed from Panc1- and MDA-MB-231 cancer stem-like cells (CSCs) isolated from each line as described[37]).

Ex vivo 11.7-Tesla (T) MR-imaging of tumors was done 24-hr after intravenous infusion of mock/non-targeted jNPs ($10^{12}$ jNPs/ml) using susceptibility weighted imaging (SWI) analysis. Comparative 9.4 Tesla MR-imaging of jNP, precursor-USPIONs and blank control phantoms in 1% agar was conducted using gradient-echo at varying echo times (TE). Targeted molecular imaging was performed using identical conditions for test and control rats via Vevo770 ultrasound contrast-imaging system at different time points schematically described in FIG. 10. Visual imaging of contrast is obtained with intensity scales optimized for visual (only) overlay of contrast and 2D-B-mode images, but quantitation is performed on identical scales. The average contrast intensity signals (CIS) are obtained at different ROIs (n=10) showing peak CIS among extratumoral feeder vessels at the base of tumors or in areas of intratumoral microvessels at each time point.

After molecular imaging, in vivo sonoporation was performed using a 1-MHz SoniGene sonoporator (Visual Sonics-Fuji™, Canada): 1 MHz, 1.5 Watt/cm2×60 seconds, 50% duty cycle. Two days after sonoporation, in vivo imaging of RFP-mediated fluorescence was performed using IVIS (Xenogen™, Inc) per manufacturer's specifications.

Analysis of jNP[miRNA]MB-Heteroplex Delivery of miRNA-126 to Tumors In Vivo.

Assembly of miRNA payload into heteroplexes and in vivo delivery is done identical to jNP[DNA]MB-heteroplexes. The inventors use 27-30 µg miRNA/$10^8$-MBs per rat (21-bp double-strand miRNA-126 mimic, Stem Loop ID: hsa-miRNA-126-5p; Ambion Life Technologies™). Two-days after miRNA-126 delivery by sonoporation of DEspR-targeted jNP[miRNA-126]MB-heteroplexes to nude rat heterotopic xenograft tumors, detection of full length miRNA-126 is performed by miRNA-126-specific quantitative real-time RT-PCR analysis. KRAS protein levels were determined by Western blot analysis.

Analysis of Circulating Cytokine Levels after jNP Infusion In Vivo.

Safety studies are done in Dahl salt-sensitive hypertensive rats using $10^{12}$- and $10^{13}$-jNPs/rat infused via tail vein without microbubbles compared to age-matched controls. Daily health monitoring is performed, and analysis of serum cytokine levels is done 2 weeks later by ELISA following manufacturer's specifications (Rat Cytokine/Chemokine Array, RayBiotech™, GA). ELISA is done in duplicates per cytokine per rat, with 2 rats/group for 3 study groups.

Statistical Analysis.

All data are checked for normality, and the appropriate statistical test applied. One-way ANOVA with Tukey's test for multiple pairwise comparisons was used to assess differences of pertinent study groups e 3, with (n=8-10 measures/study group) in different experimental systems; students t-test (normality passed) or non-parametric Wilcoxon rank sum test were used accordingly for differences in group means. Two-way ANOVA repeated measures was used for 3-group time course analysis of T2* relaxivity (n=20 measures/timepoint, n=20 timepoints). GraphPad PRISM™ (Release 5.0, GraphPad™, CA) software was used for statistical analyses.

References

1 Nguyen, J. & Szoka, F. C. Nucleic acid delivery: the missing pieces of the puzzle? *Acc. Chem. Res.* 45, 1153-1162 (2012).

2 Chen, Y., Gao, D.-Y. & Huang, L. In vivo delivery of miRNAs for cancer therapy: Challenges and strategies. *Adv. Drug Deliv. Rev.* (2014).

3 Lammers, T., Aime, S., Hennink, W. E., Storm, G. & Kiessling, F. Theranostic Nanomedicine. *Acc. Chem. Res.* 44, 1029-1038 (2011).

4 Gilleron, J. et al. Image-based analysis of lipid nanoparticle-mediated siRNA delivery, intracellular trafficking and endosomal escape. *Nat. Biotech.* 31, 638-646 (2013).

5 Sahay, G. et al. Efficiency of siRNA delivery by lipid nanoparticles is limited by endocytic recycling. *Nat. Biotech.* 31, 653-658 (2013).

6 Lentacker, I., De Cock, I., Deckers, R., De Smedt, S. C. & Moonen, C. T. Understanding ultrasound induced sonoporation: definitions and underlying mechanisms. *Adv. Drug Deliv. Rev.* 72, 49-64 (2014).

7 Sirsi, S. R. et al. Polyplex-microbubble hybrids for ultrasound-guided plasmid DNA delivery to solid tumors. *J. Control. Release* 157, 224-234 (2012).

8 Ballarin-Gonzalez, B. & Howard, K. A. Polycation-based nanoparticle delivery of RNAi therapeutics: adverse effects and solutions. *Adv Drug Deliv Rev* 64, 1717-1729 (2012).

9 Beyerle, A. et al. Inflammatory responses to pulmonary application of PEI-based siRNA nanocarriers in mice. *Biomaterials* 32, 8694-8701 (2011).

10 Tros de Ilarduya, C., Sun, Y. & Duzgunes, N. Gene delivery by lipoplexes and polyplexes. *Eur. J. Pharm. Sci.* 40, 159-170 (2010).

11 Zhou, J. et al. Biodegradable poly(amine-co-ester) terpolymers for targeted gene delivery. *Nat. Mater.* 11, 82-90 (2012).

12 Hu, S.-H. & Gao, X. Nanocomposites with Spatially Separated Functionalities for Combined Imaging and Magnetolytic Therapy. *JAGS* 132, 7234-7237 (2010).

13 Lattuada, M. & Hatton, T. A. Synthesis, properties and applications of Janus nanoparticles. *Nano Today* 6, 286-308 (2011).

14 Schick, I. et al. Multifunctional Two-Photon Active Silica-Coated Au@MnO Janus Particles for Selective Dual Functionalization and Imaging. *JACS* 136, 2473-2483 (2014).

15 Vasquez, E. S., Chu, I. W. & Walters, K. B. Janus Magnetic Nanoparticles with a Bicompartmental Polymer Brush Prepared Using Electrostatic Adsorption to Facilitate Toposelective Surface-Initiated ATRP. *Langmuir* 30 (2014).

16 Xie, J., Lee, S. & Chen, X. Nanoparticle-based theranostic agents. *Adv. Drug Deliv. Rev.* 62, 1064-1079 (2010).

17 Yen, S. K., Padmanabhan, P. & Selvan, S. T. Multifunctional iron oxide nanoparticles for diagnostics, therapy and macromolecule delivery. *Theranostics* 3, 986-1003 (2013).

18 Barrefelt, A. et al. Biodistribution, kinetics, and biological fate of SPION microbubbles in the rat. *Int. J. Nanomedicine* (2013).

19 Yang, F. et al. Superparamagnetic iron oxide nanoparticle-embedded encapsulated microbubbles as dual contrast agents of magnetic resonance and ultrasound imaging. *Biomaterials* 30, 3882-3890 (2009).

20 Budijono, S. J., Russ, B., Saad, W., Adamson, D. H. & Prud'homme, R. K. Block copolymer surface coverage on nanoparticles. *Colloids Surf, A* 360, 105-110 (2010).

21 Jokerst, J. V., Lobovkina, T., Zare, R. N. & Gambhir, S. S. Nanoparticle PEGylation for imaging and therapy. *Nanomedicine* 6, 715-728 (2011).

22 Migneault, I., Dartiguenave, C., Bertrand, M. J. & Waldron, K. C. Glutaraldehyde: behavior in aqueous solution, reaction with proteins, and application to enzyme crosslinking. *Biotechniques* 37, 790-802 (2004).

23 Cruz, L. J., Tacken, P. J., Fokkink, R. & Figdor, C. G. The influence of PEG chain length and targeting moiety on antibody-mediated delivery of nanoparticle vaccines to human dendritic cells. Biomaterials 32, 6791-6803 (2011).

24 Li, M. et al. Comparison of Two Ultrasmall Superparamagnetic Iron Oxides on Cytotoxicity and MR Imaging of Tumors. *Theranostics* 2, 76-85 (2012).

25 Duan, H. et al. Reexamining the Effects of Particle Size and Surface Chemistry on the Magnetic Properties of Iron Oxide Nanocrystals: New Insights into Spin Disorder and Proton Relaxivity. *J. Phys. Chem. Lett.* 112, 8127-8131 (2008).

26 Torchilin, V. P. Multifunctional nanocarriers. *Adv. Drug Deliv. Rev.* 64, Supplement, 302-315 (2012).

27. Tan, Y. H. et al. A nanoengineering approach for investigation and regulation of protein immobilization. *ACS Nano* 2 (2008).

28. Liu, J. et al. Computational model for nanocarrier binding to endothelium validated using in vivo, in vitro, and atomic force microscopy experiments. *Proc. Natl. Acad. Sci. U.S.A.* 107, 16530-16535 (2010).

29 Park, Y. et al. Stability of Superparamagnetic Iron Oxide Nanoparticles at Different pH Values: Experimental and Theoretical Analysis. *Langmuir* 28 (15) 6246-6255 (2012).

30 Mukhopadhyay, A., Joshi, N., Chattopadhyay, K. & De, G. A Facile Synthesis of PEG-Coated Magnetite (Fe3O4) Nanoparticles and Their Prevention of the Reduction of Cytochrome C. *ACS Appl. Mater. Interfaces* 4, 142-149 (2011).

31 Wang, L., Neoh, K. G., Kang, E. T., Shuter, B. & Wang, S.-C. Superparamagnetic Hyperbranched Polyglycerol-Grafted Fe3O4 Nanoparticles as a Novel Magnetic Resonance Imaging Contrast Agent: An In Vitro Assessment. *Adv. Funct. Mat.* 19, 2615-2622 (2009).

32 Kleemann, E. et al. Nano-carriers for DNA delivery to the lung based upon a TAT-derived peptide covalently coupled to PEG-PEI. *J. Control. Release* 109, 299-316 (2005).

33 Taratula, O. et al. Multifunctional nanomedicine platform for cancer specific delivery of siRNA by superparamagnetic iron oxide nanoparticles-dendrimer complexes. *Curr. Drug Deliv.* 8, 59-69 (2011).

34 Herrera, V. L. et al. DEspR Roles in Tumor Vasculo-Angiogenesis, Invasiveness, CSC-Survival and Anoikis Resistance: A 'Common Receptor Coordinator' Paradigm. *PLOS ONE* 9 (1) e85821 (2014).

35 Taurin, S., Nehoff H Fau-Greish, K. & Greish, K. Anticancer nanomedicine and tumor vascular permeability; Where is the missing link? *J. Control. Release* 164, 265-275 (2012).

36 Soo Choi, H. et al. Renal clearance of quantum dots. *Nat. Biotech.* 25, 1165-1170 (2007).

37 Decano, J. L., Moran, A. M., Ruiz-Opazo, N. & Herrera, V. L. Molecular imaging of vasa vasorum neovascularization via DEspR-targeted contrast-enhanced ultrasound micro-imaging in transgenic atherosclerosis rat model. *Mol. Imaging Biol.* 13, 1096-1106 (2011).

38 Frampton, A. E. et al. Loss of miR-126 is crucial to pancreatic cancer progression. *Expert Rev. Anticancer Ther.* 12, 881-884 (2012).

39 Hamada, S. et al. MiR-126 acts as a tumor suppressor in pancreatic cancer cells via the regulation of ADAMS. *Mol. Cancer Res.* 10, 3-10 (2012).

40 Tavazoie, S. F. et al. Endogenous human microRNAs that suppress breast cancer metastasis. *Nature* 451, 147-152 (2008).

41 Marshall, J. S. Mast-cell responses to pathogens. *Nat. Rev. Immunol.* 4, 787-799 (2004).

42 Kawakami, S., Ito, Y., Charoensit, P., Yamashita, F. & Hashida, M. Evaluation of proinflammatory cytokine production induced by linear and branched polyethylenimine/plasmid DNA complexes in mice. *J Pharmacol. Exp. Ther.* 317, 1382-1390 (2006).

43 Lattuada, M. & Hatton, T. A. Preparation and Controlled Self-Assembly of Janus Magnetic Nanoparticles. *JACS* 129, 12878-12889 (2007).

44 Wang, D. S. et al. Cationic versus neutral microbubbles for ultrasound-mediated gene delivery in cancer. *Radiology* 264, 721-732 (2012).

45 Delalande, A., Kotopoulis S., Postema, M., Midoux, P., Pichon, C. Sonoporation: mechanistic insights and ongoing challenges for gene transfer. *Gene* 525 (10) 191-199 (2013).

46 Gao, X. et al. The association of autophagy with polyethylenimine-induced cytotoxicity in nephritic and hepatic cell lines. *Biomaterials* 32, 8613-8625 (2011).

47 Hunter, A. C. & Moghimi, S. M. Cationic carriers of genetic material and cell death: a mitochondrial tale. *Biochim. Biophys. Acta* 1797, 1203-1209 (2010).

48 Tay, C. Y., Menon, N., Leong, D. T., & Tan, L. P. Molecular architecture governs cytotoxicity and gene transfection efficacy of polyethylenimine based nanoplexes in mammalian cell lines. *J Inorg Organomet Polym* 25, 301-311 (2015).

49 Caldorera-Moore, M. E., Liechty, W. B. & Peppas, N. A. Responsive Theranostic Systems: Integration of Diagnostic Imaging Agents and Responsive Controlled Release Drug Delivery Carriers. *Acc. Chem. Res.* 44, 1061-1070 (2011).

50 Guo, S. & Huang, L. Nanoparticles Escaping RES and Endosome: Challenges for siRNA Delivery for Cancer Therapy. *J. Nanomat.* 2011, 1-12 (2011).

Example 3: Supplementary Methods

Synthesis and Surface Modification of jNPs

Janus functionalized nanoparticles are prepared using the following materials: Iron tri(acetylacetonate) (99.9%), citric acid (CA; 99.5+%), methanol (99.8%), acetone, benzyl ether (99%), N-hydroxysuccinimide ester (NHS ester; 98%), oleic acid (OA; 90%), oleyl amine (OAm; 70%)$_1$-ethyl-3-(3-dimethylamino-propyl)carbodiimide hydrochloride (EDC; 97%) (Sigma™, St. Louis, Mo.); 1,2-dichlorobenzene (DCB; 99%), N,N2-dimethylformamide (DMF; 99.8%), diethyl ether (99.9%), and hexane (99.9%) (Acros™, Morris Plains, N.J.). Ethanol (ACS grade) (Pharmco™, Lees Summit, Mo.); amine-terminated polyethylene glycol (mPEG-NH2) with molecular weight 2000 Da (Laysan Bio™, Inc, Arab, Ala.); NH2-mPEG-NH2 with molecular weight 3400 Da (Creative PEGWorks™, Winston Salem, N.C.); RFP minigene (pTurbo FP635-N cat # FP722, Evrogen™, Moscow, Russia), Alexafluor 594 or 568 labeling kits (Invitrogen™, Carlsbad, Calif., USA); anti-rat DEspR monoclonal antibodies (ProMab™, CA) and IgG2 isotype (Santa Cruz Biotechnology™, Sta. Cruz, Calif.); MicroMarker microbubbles (Visual Sonics-Fuji™, Inc., Canada). Iron oxide NPs are first synthesized according to the method described by Sun et al'. Briefly, NPs are produced by an organic phase process reacting $Fe(acac)_3$ and a long-chain alcohol, and then modified to yield monodisperse citric acid-coated $Fe_3O_4$ NPs about 10 nm in diameter. The NPs are then functionalized to contain a mixture of different polyethylene glycol (PEG) chains on their surface and attached as previously been described.[2] The mixed PEG brush is comprised of: molecular weight 2000 Da (PEG2000) and 3400 Da (PEG3400) in a 4:1 ratio. PEG2000 molecules are amine-terminated at one end, while PEG3400 molecules are amine-terminated in both ends. PEG chains are attached to carboxyl groups of citric acid on the USPION surface through N-hydroxysuccinimide (NHS) ester and 1-ethyl-3-(3-dimethylaminopropyl) carbodiimide hydrochloride (EDC) coupling[2]. This results in a mixed PEG brush coat around the USPION[3], referred to as the precursor-USPION for production of Janus-functionalized nanoparticles (jNPs).

The asymmetric functionalization method is based on previously reported layer-by-layer methods[4,5]. In order to prepare jNPs, a freshly 3x cleaved mica surface is placed in a 100 mm-diameter petri dish. The square mica sheet is adjusted in size to fit in the dish. Magnets are attached to the underside of the petri dish in order to keep the magnetic USPIONs in place during the functionalization procedure. Upon placement in the petri dish, the mica sheet is incubated with 0.1% solution of linear polyethyleneimine of MW 25 kDa (PEI), followed by incubation with 5% glutaraldehyde solution to react with secondary amines on PEI. After a wash step, Mixed-brush PEGylated USPIONs are then introduced to the mica sheet with just enough SPIONs to cover the mica plate with a thin layer of USPIONs and held down by the magnet. The glutaraldehyde is allowed to react with amine groups on PEG3400, creating a monolayer of USPIONs bound on one side to the mica surface. The unbound face of the USPIONs oriented away from the mica is then reacted with N-hydroxysuccinimide maleimide (NHS-MAL) at 100 μg/mL to convert free amines on the PEG3400 to a MAL. Targeting antibodies (ab), anti-DEspR, or control non-targeting non-specific IgG are presented to USPIONs for test jNPs and control jNPs respectively, and allowed to attach overnight with gentle agitation. Attachment of the ab-protein to the USPION is achieved by coupling MAL on USPIONs to thiol groups on cysteine residues in the antibodies. Based on exposed USPION surface volume and antibody 12-nm diameter, approximately 9-13 antibodies are attached to each USPION. Upon attachment of targeting antibodies to the USPIONs, the mica sheet is washed and the now functionalized Janus nanoparticles, jNPs, released using 0.2 M NaCl, disrupting the electrostatic interaction between the mica sheet and PEI. Upon release, the solution is diluted with dI H2O to yield a final NaCl concentration of 0.15 M. The resulting particles encompass asymmetric functionalization with one face, the payload-face, comprised of polycationic PEI, and the 2nd face, the targeting-face, presenting antibodies.

Verification of Layer-by-Layer Functionalized jNPs

In order to verify different steps of the functionalization, tests are conducted at different points of the procedure. The synthesis of PEGylated USPIONs had previously been verified in the inventors' laboratory through transmission electron microscopy, dynamic light scattering, zeta potential, elemental analysis and iron quantification.[6] In order to verify that the USPION surface is functionalized with a mixed layer of PEG2000 and amine-terminated PEG3400, analysis of increases in hydrodynamic radius from a 100% PEG 2000 layer to a 80%/20% PEG2000/PEG3400-NH2 layer are measured on a Brookhaven 90Plus (Brookhaven Instrument™, Holtsville, N.Y.) using dynamic light scattering (DLS). A positive shift in the zeta potential using the same instrument also provides confirmation. In order to verify the attachment of PEI, USPIONs are released before attachment of the targeting antibody, and a further positive shift of the zeta potential are measured. In order to confirm attachment of targeting antibodies, the antibodies are fluorescently labeled, and fluorescence is measured upon release from mica and subsequent wash of the targeted jNPs. Antibodies are fluorescently labeled using the Alexa Fluor® Protein Labeling Kit from Invitrogen™.

Quantitation of jNPs

The number of jNPs produced by the method are quantified using the following materials: Thioglycolic acid 98%, Hydroxylamine hydrochloride, 1,10-Phenathroline, sodium citrate, Concentrated $H_2SO_4$, Ammonium iron(II) sulfate hexahydrate (Sigma Aldrich™, MO, USA). jNPs are quantified using an adapted method from Nitin et al'. The number of jNPs is determined by CCD camera (Gauting, Germany) using EMMENU4 Program. A low dose kit minimizes irradiation damage to the sample.

Atomic Force Microscopy (AFM) Images of jNPs

AFM imaging is performed using an Agilent 5500 AFM operated in intermittent contact mode (Acoustic AC (AAC) mode) using a Mac II cantilever (Agilent Technologies™) with a resonant frequency of approximately 75 kHz and a spring constant of 2.8 N/m. AFM images are recorded at a resolution of 512×512 pixels at a line rate of 1 line/sec. Scan sizes ranged from 300 nm×300 nm up to 1.5 m×1.5 m.

Ethidium Bromide Dye Exclusion and Displacement Assays

The binding of jNPs to DNA is tested by ethidium bromide (EtBr) dye exclusion assay (Kleenman et al 2005) based on the principle that EtBr fluoresces only when it intercalates into DNA base pairs. Fluorescence therefore indicates free DNA base pairs that are not bound to jNPs. To demonstrate specificity, increasing amounts of jNPs (0, 0.2, 0.6, 1.8×10[10] jNPs) are mixed together with two different amounts of DNA (100 ng and 300 ng) and tested for EtBr fluorescence at two time points: 10 min and at 1 hr. Fluorescence reads are done at 260 nm excitation/590 nm emission, and background autofluorescence of non-intercalated EtBr is subtracted. Afterwards, samples are then run in 0.8% agarose gels and fluorescence from EtBr intercalated into DNA is visualized with UV 260 nm excitation and photographed.

To further test affinity of jNP for DNA, we use an EtBr displacement assay (Taratula et al 2011), based on loss of fluorescence upon displacement of EtBr from DNA base pairs (bp) by jNPs binding to DNA with deduced equal or greater affinity. Aliquots of DNA plasmid in a 96-well plate (100 ng or 250 ng plasmid GFP-DNA per well) in physiological salt solution (150 mM NaCl, pH=7) are incubated for 10 min with a molar ratio of 4:1 bp:EtBr. Increasing amounts of a solution containing $1.22 \times 10^{13}$ jNPs/ml in 150 mM NaCl is added to aliquots of DNA plasmid and brought to a final working concentration of 200 l with additional physiological salt solution. Fluorescence of intercalated EtBr is measured at Ex./Em. of 480/590 nm using a Spectramax™ M5 plate reader (Molecular Devices™, Sunnyvale, Calif.), and relative fluorescence values are reported as the ratio of fluorescence intensity of the sample containing jNP to samples containing EtBr/DNA plasmid alone (n=6).

Analysis of jNP Stability in Serum

Stability against aggregation and loss of particle functionalization is demonstrated by observing the effective diameter of jNPs in 85% rat serum solution using both Dynamic Light Scattering (DLS) and Atomic Force Microscopy (AFM). Briefly, 250 µl of jNP in 150 mM NaCl is mixed with pure rat serum for a final jNP concentration of $8.5 \times 10^{11}$ particles/ml in 75% rat serum. Mean jNP diameters are determined via DLS using a Brookhaven 90Plus (Brookhaven Instrument™, Holtsville, N.Y.) over several time points: 0, 1 hr, 3 hr, and 24 hr. Additionally, at each time point, 10 µl is removed from the sample and deposited on a mica slide under a magnet. After allowing jNPs to deposit on the surface for one hour, slides are rinsed with DI water and dried for 48 hr before imaging using AFM. Due to the nonsymmetrical shape of the jNP, AFM effective diameter is reported as the longest diameter through the SPION core.

AFM Imaging of Modeled jNP Interaction with Lambda Phage DNA

To further document interaction of jNPs with DNA, we use AFM to directly image jNP binding to deposited lambda phage DNA strands. Both 1 µl of a $1 \times 10^{13}$ solution of jNP and 25 µl of 1 mg/ml»phage DNA are co-deposited on a mica slide under a magnet. After allowing 1-hour for jNPs and DNA to interact and deposit, the slide is rinsed with deionized water and air dried for 48-hours prior to AFM imaging. Images are taken as described above.

Stepwise jNP[DNA]MB-Heteroplex Assembly

The heteroplex is assembled stepwise in physiological phosphate buffered saline under constant slow rotation. The inventors used commercially available MicroMarker™ microbubbles (VisualSonics-Fuji™, Inc) which have been characterized by others (Escoffre J M et al 2011; Escorfree et al 2013; Olive K P et al 2009; Sun C et al 2014) as follows.

Size: 2-3 microns
Shell: phospholipids, PEG, fatty acids
Gas: $N_2C_4F_{10}$
Surface charge: negative MicroMarker™ MBs with streptavidin (Target-Ready MicroMarker™ MBs, Visual Sonics Inc™), used for control DEspR-targeted non-jNP-MBs for in vivo molecular imaging and used for control DEspR-targeted [DNA]MBs in DNA delivery studies, were characterized and described by different research groups (Helfield et al 2013; Lee D J et al 2008; Loveless M E et al, 2009; Lyshchik et al 2007; Rychak J J et al 2007; Willmann J K et al 2008; Willmann J K et al 2010) and found to have the following characteristics:

MicroMarker MBs with streptavidin: 1-2 microns or 2-3 microns
7,600 streptavidin molecules/2 (Willmann et al, 2008); and 4 moles of biotin bind 1 mole streptavidin (ProZyme)
Streptavidin-positive MicroMarker MBs have been validated for molecular imaging by different groups using antibodies targeting VEGFR2, and integrin.

MicroMarker microbubbles have also been characterized for delivery of DNA via sonoporation, as well as acoustical behavior, and transfection efficiency in vitro. (Piron et al 2010; Escoffre J M et al 2013a; Delalande A et al 2013; Escoffre J M, et al 2013b).

For jNP[DNA]MB-heteroplex assembly, MBs are resuspended in normal saline (150 mM NaCl) for 10 min following manufacturer's specifications. Then 30 g of RFP-plasmid DNA, or 27 g of miRNA-126, or 15 g of single strand oligoDNA$^{AF468}$ is incubated with $1 \times 10^8$ microbubbles for 15 mM, followed by incubation with jNPs calculated to cover 0.05%, 1%, 10%, or 50% ($1 \times 10^{12}$ jNPs for 10% coverage of $10^8$ MBs/rat, or $10^4$/MB) of the microbubble surface for another 45 mM before further use or analysis.

FACS Analysis of jNP[DNA]MB-Heteroplex Stepwise Assembly

To document assembly of the jNP[DNA]MB-heteroplex, the inventors followed the identical stepwise assembly described above, and used fluorescent jNPs prepared using fluorescently labeled anti-DEspR monoclonal antibodies (Alexa Fluor AF594) as the targeting moiety in the layering preparation of jNPs. Assembly of fluorescent jNPs with [DNA]MBs would therefore result in fluorescent jNP[DNA] MB-heteroplexes as distinguished from non-fluorescent jNP-negative [DNA]MBs on FACS analysis (LSRII flow cytometer, Becton Dickinson™, Inc). Increased granularity is assessed by side scatter. Increasing coverage (1%, 10% and 50% coverage) of the 2 µm microbubble by jNPs is tested by FACs analysis.

To directly demonstrate binding of nucleic acid to microbubbles followed by complexing of jNPs onto [DNA] MBs, the inventors used double-labeled FACS analysis using commercially available 50 nucleotide-long AF488-labeled oligoDNA (DNA$^{AF488}$) and fluorescent jNPs with non-targeted AF568-labeled IgG (goat anti-rabbit IgG, Pierce Thermo Scientific™, Rockford Ill.). After resuspension of commercially available, non-fluorescent microbubbles (MicroMarkers™, VisualSonics-Fuji™, Inc., Canada), an aliquot of $10^8$ MBs is mixed with 15 ug oligoDNA$^{AF488}$ for 15 min with gentle mixing on a rotator, and an aliquot analyzed by FACS analysis to document fluorescence of MBs upon DNA. Then fluorescent [oligoDNA$^{AF488}$]MBs are mixed with fluorescent jNPs (jNP$^{AF868}$) for 45 min and then analyzed by FACS analysis (t−1 hr; t−24 hr) for double fluorescent fully assembled jNP[DNA]MB-heteroplexes to distinguish from single fluorescent oligo-DNA bound MBs and non-fluorescent free MBs. Although the measured zeta potential of MBs alone is ∼−20 mV, FACS analysis show efficient and stable (up to 24 hr) binding of DNA to MBs (50-90% of MBs bound), thus indicating that MBs have amphoteric surfaces.

FACS of jNP[DNA]MB-Heteroplex Binding to Cells

Human pancreatic cancer (Panc1) tumor cells are cultured as specified (ATCC™) and maintained at 37 C in a humidified 5% $CO_2$ incubator. Panc1 tumor cells are isolated, washed then incubated with fluorescent jNP$^{AF594}$[DNA] MB-heteroplexes at room temperature with gentle rotation at 1:1 and at 1:5 cell-to-jNP[DNA]MB-heteroplex ratio for 45-60 min. Targeting efficiency is analyzed comparing the % of Panc1 tumor cells that gain fluorescence between the two ratios by FACS analysis (LSR II, BD Sciences, USA). Detection of fluorescent cells would indicate successful targeting of cells by fluorescent jNP[DNA]MB-heteroplexes through anti-DEspR ab interactions with the cognate receptor (DEspR) on Panc1 tumor cells[10]. Quantitation of relative amounts of gain-of-fluorescence by Panc1 tumor cells bound to fluorescent jNP[DNA]MB-heteroplexes to non-fluorescent Panc1 tumor cells, and free jNP[DNA]MB-heteroplexes is achieved using FACS analysis and FloJo™ analysis software.

In Vitro Analysis of jNP[DNA]MB-Heteroplex Binding to Panc1 Cell Under Flow

Panc1 cells are grown as described above in IBIDI perfusion 6-lane micro-slide VI (ibidiGmbH, Germany), and the DEspR-targeted jNP[DNA]MB-heteroplex labeled with AlexaFluor 594 on the targeting antibody moiety is introduced into the chamber and incubated for 45 min with vertical rotation. Afterwards, the media is flushed with 1× phosphate buffered saline to wash off free fluorescent jNP[DNA]MB-heteroplexes. Cell nuclei are counterstained with DAPI (blue fluorescence). Imaging is done using a Nikon epi-fluorescence microscope (Nikon, Japan) for red fluorescence (AlexaFluor-labeled DEspR-targeted jNP* [DNA] MB), blue fluorescence (DAPI nuclear stain), as well as phase-contrast imaging to delineate cell membranes. Non-specific binding of the heteroplex is analyzed using jNPs functionalized with AlexaFluor 594-labeled IgG2 isotype antibody.

Analysis of jNP[DNA]MB-Heteroplex Payload Delivery

Panc1 tumor cells are grown in OptiCell closed cell-culture system (Nunc/Thermo Scientific™, USA) with 75-m thick gas-permeable membrane walls. The inventors used a Vevo770 ultrasound imaging system with contrast-enhanced capabilities (Visual Sonics-Fuji™, Inc., Canada) to demonstrate echolucency of membrane walls for sonoporation and to be able to detect and sequence-destruct bound microbubbles (Micromarkers™, VisualSonics™, Inc). Following identical conditions, test and control jNP[DNA]MB-heteroplexes, prepared as described above, and non-jNP[DNA]MB controls are allowed to interact with cells for 45 min with constant vertical rotation of OptiCell™ systems to simulate shear. Excess unbound targeted and non-targeted jNP[DNA]MB-heteroplexes and control non-jNP targeted 'standard' [DNA]MBs, as well as any free jNPs, DNA and MBs are removed, followed by one wash with media after 45 min, and new media added. Sonoporation is performed using a 1 MHz SoniGene™ sonoporator (VisualSonics-Fuji, Inc™, Canada) at 1.5 watts/cm$^2$ for 60 sec, 50% duty cycle (n=8 independent sonoporation-sites in 2 different OptiCell™ culture systems per group, with a designated non-sonoporated area as a control in each OptiCell™ culture system.)

After 48 hr, analyses of cell health and RFP-mediated fluorescence are done using a Nikon™ epi-fluorescent microscope as described above. Targeted jNP[DNA]MBs had anti-human DEspR monoclonal ab (mAb) (in-house development) as the targeting moiety for the jNP. DEspR is present on Panc1 tumor cells (Herrera et al., 2014). The inventors compared DEspR-targeted jNP[DNA]MB-heteroplexes to non-targeted [DNA]MBs, non jNP/DEspR-targeted[DNA]MBs, and control non-specific ab jNP[DNA]MB-heteroplexes to determine efficiency of targeted-delivery. The inventors also compared sites in the same OptiCell™ culture system with and without sonoporation. Quantitative analysis is performed by determining the % fluorescent RFP-positive cells over total cells in two high power fields (HPF) per 8 independent sonoporation sites and 4 independent non-sonoporation sites, (n=8-16 HPF sites).

MR-Imaging Analysis of Tumors and Normal Liver and Kidney

MRI is performed in an 11.7 Tesla vertical-bore Bruker Avance spectrometer. The inventors use a clinical MRI sequence called susceptibility weighted imaging (SWI) to analyze tumor tissue samples. SWI is a unique pulse sequence which combines both the phase and magnitude information, which has been proven to show sensitivity to iron particles—detected in venous blood, hemorrhage, iron storage or nanoparticles. For MRI of liver and kidney, the Fast Low Angle SHot™ (FLASH) clinical MRI sequence is used.

MR-Imaging Comparing jNPs and SPION-PEG-NH2.

Three 5 mm NMR tubes are filled with agar alone, or with agar containing jNPs or SPION-PEG-NH2 at a concentration of $0.5 \times 10^{12}$ jNPs/ml in 1% agar. These tubes are then embedded in 2% agar inside a 26 mm diameter plastic tube, with their long axes parallel to the long axis of the outer tube. This assembly is placed at the isocenter of a 9.4T horizontal axis MRI scanner (Bruker Biospec™, Billerica, Mass.) with the tubes oriented parallel to the magnetic field. Axial and coronal T2-weighted rapid acquisition with relaxation enhancement (RARE) images are acquired with TR/TE=3300/22 ms, echo train length=4 ms.

T2* relaxation times in the three vials are assessed using a multi-gradient echo sequence with TR=300 ms, 26 degree flip angle, and 20 echoes per image acquired at echo times ranging from 4.08 to 99.08 ms in 5 ms steps. To minimize effects of macroscopic magnetic field variations (which can shorten T2*), two steps are taken. First, prior to each measurement, the magnetic field is shimmed locally using a point-resolved spectroscopy (PRESS) sequence to minimize the proton linewidth in a 5-6 mm cube centered on the vial of interest. The line width (FWHM) ranged from 7-13 Hz in the three vials prior to T2* measurement in each vial. Second, each multi-gradient echo image series is acquired with two voxel sizes. A first acquisition is performed with 1 mm slice thickness and 0.312 mm in-plane resolution, and a second is then acquired with 0.5 mm slice and 0.156 mm in-plane resolution. The second acquisition had half the voxel size of the first, and hence will have approximately half as much intravoxel dephasing due to macroscopic magnetic field inhomogeneities. Under these conditions, the T2* measurements are consistent (within error) between the two data sets. T2* in each voxel is determined by fitting the pixel intensities within a region of interest centered within the vial to a function of the form Ae-TE/T2*+b, where b is an overall offset representing the noise floor in these magnitude images.

Analysis of jNP[DNA]MB-Heteroplex Targeted Molecular Imaging

After obtaining baseline ultrasound 2-dimensional B-mode imaging and baseline IVIS documentation of zero-fluorescence of tumors, experiments are done using jNP[DNA]MB-heteroplexes with an estimated 10% jNP-coverage of microbubbles. Heteroplexes comprise: [30 ug DNA], [$1 \times 10^8$ MBs], and [$1 \times 10^{12}$ jNPs]. Rats are infused with either test DEspR-targeted jNP[DNA]MB-heteroplex or control non-jNP DEspR-targeted DNA/MBs in which the same anti-DEspR antibody is linked to MBs via biotin-streptavidin coupling.[11] After allowing most microbubbles to clear the circulation (about ~5 min),[11] target-bound microbubbles are visualized by contrast-enhanced imaging of tumor feeder vessels at the base of the tumor and intratumoral microvessels, using the Vevo770 contrast-enhanced imaging program and software analysis at 10- 20-, and 30-min post-infusion (t–20, t–30).

The inventors performed contrast-enhanced ultrasound imaging using with identical settings for all tumors following precautions to minimize movement artifacts: rats were anesthetized, scanhead was immobilized using the Vevo770™ scanhead-specific rail-system, and imaging was gated to respirations. The inventors used the Vevo770™

Contrast Mode parameters as per manufacturer's specifications similar to published description by Lee et al., 2008, and Willmann et al., 2008 and 2010, except that the inventors use a rat-appropriate scanhead—the RMV16, and modified the contrast-imaging protocol in terms of timing as described below.

More specifically, the inventors used a Vevo770™ (VisualSonics-Fuji Inc™) ultrasound imaging system and RMV-16 with broadband frequency up to 23.5 MHz, axial resolution of 85 microns and lateral resolution of 215 microns at focal length 17.5 mm, field of view up to 33 mm. B-mode imaging was optimized with acoustic focus entered at the level of the spontaneous mammary tumor. Rats were maintained on 1.2-1.5% isoflurane during scanning; and all imaging settings were kept constant for all imaging sessions. Tail vein infusions of test and control MBs (total $10^8$ MBs/rat) were done respectively with documentation of increased contrast intensity signals (CISs) from the inflow of MBs. After 5 minutes, ascertainment of clearance of most, if not all. MBs from the circulation was checked. At t–10, the first molecular imaging tumor scan was done gated to respirations, and with the scanhead immobilized on the Vevo770™ rail system to eliminate movement artifacts manifested as speckle variance. 200 ultrasonographic frames were obtained at a temporal resolution of 10 seconds, followed by a destruction pulse [20 cycles, 10 MHz, mechanical index of 0.59] for 3 seconds followed by imaging for another 20 seconds (~400 frames) post-destruction.

Image processing and quantification are done using the Vevo770™ contrast Mode analysis offline for regions of interest (ROI) corresponding to feeder vessels and intratumoral vessels. As described Lyshchik et al., 2007, "image processing in the Vevo770™ system relies on 2 sets of images: a predestruction set and a postdestruction data set . . . . Images from the predestruction set were paired to their partner images in the postdestruction set using an absolute sum-of-differences technique . . . . Once the image pairs were calculated, the subtracted image was generated and displayed in shades of green on top of the B-mode image by a blending algorithm to provide a map of the spatial distribution of the ultrasound contrast agents retained by the tissues." (Lyshchik et al., 2007) Offline analysis with the Vevo770™ Contrast Enhanced Imaging software of operator-selected ROIs then plots contrast intensity signals against time (time intensity plots) demarcating predestruction and postdestruction CISs.

This protocol is repeated in 2-3 other regions of the tumors and the sequence repeated detecting stable receptor-targeted adherent MBs. Comparative analysis was then done using 10 ROIs per study group comprised of: the later two time points (t20, t30), two vessel types (extratumoral feeder vessels and intratumoral microvessels, and analysis of test (DEspR-targeted jNP[DNA]MBs], and control non-jNP DEspR-targeted MBs.

In Vivo DNA/miRNA-Payload Delivery by Sonoporation Using jNP[DNA/miRNA-126]MB-Heteroplexes After contrast-enhanced ultrasound molecular imaging, sonoporation is performed using the SoniGene sonoporator with a 1 cm-diameter 1 MHz probe with a half-value depth of 2.3 cm. Sonoporation is performed with the following settings: 50% duty cycle, for 1.5 watts/cm2, for 60 seconds, 153 kPa (Sonigene, Visual Sonics Inc, Canada).

Delivery and functional expression (transcription, translation) of the RFP-minigene is determined by imaging red fluorescence in tumors by IVIS (Xenogen™, Inc) two days after sonoporation. Mock-sonoporated rats (sonoporation, no microbubbles) serve as negative controls and are imaged side-by-side with the jNP[DNA]MB-heteroplex-sonoporated rat to ascertain identical conditions and set-up for valid comparative fluorescence imaging studies.

RNA Isolation and Quantitative Real-Time RT-PCR Analysis for miRNA-126 Levels

RNA is isolated from 50 mg of pulverized frozen xenograft tumor tissue using the miRNeasy™ Mini Kit (Qiagen™, Maryland USA) following the manufacturer's recommended protocol. Reverse transcription (RT) is performed using the miScript™ II Reverse Transcription Kit (Qiagen™, Maryland USA) with the following conditions: Two micrograms of total RNA are reverse transcribed in HiSpec™ Buffer, which facilitates selective conversion of mature miRNAs into cDNA. Twenty microliter reactions are set up following manufacturer's specifications and incubated at 37° C. for 1 hr, then 95° C. for 5 min. Real-time quantitative reverse transcriptase-polymerase chain reaction (qRT-PCR) for detection of mature miRNA-126 is performed using the miScript™ SYBR Green PCR Kit (Qiagen™, Maryland USA) together with the miRNA-126 miScript™ Primer Assay (Qiagen™, Maryland USA). Cycling is done in a StepOnePlus™ machine (Applied Biosystems™, California USA) with the following thermal profile: 95° C. for 15 min; 40 cycles of 94° C. for 15 sec, 55° C. for 30 sec, 72° C. for 30 sec with optics on; followed by a melt curve analysis. miRNA-126 sequences for rat and human are identical.

Western Blot Analysis of KRAS Protein Levels as a Downstream Target of Delivered miRNA-126.

Cytosolic proteins are isolated from an aliquot of frozen pulverized xenograft tumors used for miRNA-126 real-time qRT-PCR analysis. Western blot analysis is done as described[10] using equal amounts of cytosolic protein extract (30 µg) isolated from MDA-MB-231 and Panc1 CSC-derived xenograft tumors from test and control tumors. Cytosolic extracts are prepared by tissue homogenization in buffer containing 20 mM Tris-HCl pH 7.4, 1 mM EDTA, 250 mM Sucrose, protease inhibitors, followed by centrifugation (11000 g×10 min) and final collection of supernatant (cytosolic fraction). Proteins are separated on a 15% SDS-PAGE and are transferred to PVDF membrane (Bio-Rad™). The Western blot is reacted sequentially with anti-KRAS (Abcam™ cat # ab55391 at 20 µg/ml) followed by anti-β-actin (Santa Cruz™ cat # sc-47778 at 1 µg/ml) antibodies. Immunoreactive proteins are detected by chemiluminescence using the ECL Western Detection kit (GE Healthcare™).

References for Supplementary Methods
1. Sun, S. Monodisperse $MFe_2O_4$ (M=Fe, Co, Mn) Nanoparticles. 126, 273-279 (2004).
2. Lattuada, M. & Hatton, T. A. Functionalization of monodisperse magnetic nanoparticles. 23, 2158-2168 (2007).
3. Budijono, S. J. Block copolymer surface coverage on nanoparticles. 360, 105-110 (2010).
4. Sardar, R., & Shumaker-Parry, J. S. Asymmetrically functionalized gold nanoparticles organized in one-dimensional chains. 8, 731-736 (2008).
5. Wang, B., Li, B., Zhao, B., & Li, C. V. Amphiphilic Janus gold nanoparticles via combining "solid-state grafting-to" and "grafting-from" methods. 130, 11594-11595 (2008).
6. Park, Y. C. Effect of PEG molecular weight on stability, T2 contrast, cytotoxicity, and cellular uptake of superparamagnetic iron oxide nanoparticles (SPIONs). . 11, 106-14 (2014).

7. Nitin, N. Functionalization and peptide-based delivery of magnetic nanoparticles as an intracellular MRI contrast agent. 9, 706-712 (2004).
8. Dubochet, J., Groom, M. & Mueller-Neuteboom, S. The mounting of macromolecules for electron microscopy with particular reference to surface phenomena and the treatment of support films by glow discharge. 8, 107-135 (1982).
9. Dubochet, J. Cryo-electron microscopy of vitrified specimens. 21, 129-228 (1988).
10. Herrera V L, Decano J L, Tan G A, Moran A M, Pasion K A, Matsubara Y, Ruiz-Opazo N. 2014. DEspR roles in tumor vasculo-angiogenesis, invasiveness, CSC-survival and anoikis resistance: a 'common receptor coordinator' paradigm. 9, e85821.
11. Decano, J. L., Moran, A. M., Ruiz-Opazo, N., Herrera, V. L. M. Molecular Imaging of vasa vasorum neovascularization via DEspR-targeted contrast-enhanced ultrasound micro-imaging in transgenic atherosclerosis rat model. 13, 1096-1106 (2011).
12. Escoffre J M1, Novell A, Piron J, Zeghimi A, Doinikov A, Bouakaz A. "Microbubble attenuation and destruction: are they involved in sonoporation efficiency?" (2013) *IEEE Trans Ultrason Ferroelectr Freq Control.* 2013 January; 60(1):46-52.
13. Kleemann, E. Nano-carriers for DNA delivery to the lung based upon a TAT-derived peptide covalently coupled to PEG-PEI. *J Controlled Release* 109:299-316 (2005).
14. Taratula, O. Multifunctional nanomedicine platform for cancer specific delivery of siRNA by superparamagnetic iron oxide nanoparticles-dendrimer complexes. *Current Drug Delivery* 8:59-69 (2011).
15. Delalande A, Kotopoulis S, Postema M, Midoux P, Pichon C. Sonoporation: mechanistic insights and ongoing challenges for gene transfer. *Gene* (2013) 525:191-199.
16. Escoffre J M, Zeghimi A, Novell A, Bouakaz A. (2013-b). In vivo gene delivery by sonoporation: recent progress and prospects. *Current Gene Therapy* 13:2-14 (2013).
17. Escoffre J M, Piron J, Novell A, Bouakaz A. Doxorubicin delivery into tumor cells with ultrasound and microbubbles. *ACS Molecular Pharmaceutics* 8:799-806, 2011.
18. Escoffre J M, Novell A, Serrier S, Lecomte T, Bouakaz A. Irinotecan delivery by microbubble-assisted ultrasound: in vitro validation and a pilot preclinical study. *Mol Pharmaceutics* 10:2667-2675, 2013.
19. Lentacker I, DeCock I, Deckers R, DeSmedt S C, Moonen C T W. Understanding ultrasound induced sonoporation: definitions and underlying mechanisms. *Advanced Drug Delivery Reviews,* 2014.
20. Loveless M E, Whisenant J G, Wilson K, Lyshchik A, Sinha T K, Gore J C, et al. Coregistration of ultrasonography and magnetic resonance imaging with a preliminary investigation of the spatial olocalization of vascular endothelial growth factor receptor 2 expression and tumor perfusion in a murine model. *Mol Imaging* 2009 August; 8(4):187-98.
21. Mohamedi G, Azmin M, Pastoriza-Santos I, Huang V, Perez-Juste J, Liz-Marzan L M, Edinsinghe M, Stride E. 2012. Effects of gold nanoparticles on the stability of microbubbles. *Langmuir* 28:13808-13815.
22. Mullin L B, Phillips L C, Dayton P A. Nanoparticle delivery enhancement with acoustically activated microbubbles. *IEEE Trans Ultrason Ferroelect Freq Control* 60(1), (2013).
23. Olive K P, Jacobetz M A, Davidson C J, Gopinathan A, McIntyre D, Honess D, et al. Inhibition of hedgehog signaling enhances delivery of chemotherapy in a mouse model of pancreatic cancer. *Science* 2009 Jun. 12; 324 (5933):1457-61.
24. Sun, C. et al., In vitro acoustic characterization of three phospholipid ultrasound contrast agents from 2-43 MHz. *Ultrasound Med Biol.* March 2014; 40(3): 541-550.
25. Willmann J K, Kimura R H, Deshpande N, Lutz A M, Cochran J R, Gambhir S S. Targeted contrast-enhanced ultrasound imaging of tumor angiogenesis with contrast microbubbles conjugated to integrin-binding knottin peptides. *J Nucl Med* 2010. 51:433-440.

Example 4: Use of jNP as Negative Contrast Agent for MRI of Tumor Enhanced Permeability and Retention (EPR) and for Target-Specific Molecular MR-Imaging of Tumors Specifically contemplated herein are methods and compositions comprising janus nanoparticles (jNPs) as described herein for use in MRI imaging, particularly tumor imaging.

Provided herein, in one aspect, are methods relating to the use of non-targeted jNPs as negative contrast agents for MR-imaging of EPR in any tumor tissue type (i.e., not specific to a particular receptor or target). Such methods and compositions are essentially contemplated for use as a universal MRI contrast agent for monitoring EPR.

Clinically, EPR is the phenomenon by which drugs enter tumors and are 'enriched' in tumors in contrast to normal tissues. Detection of EPR and monitoring of EPR using jNPs will permit one of skill in the art to determine drug response and tumor localization. Such methods are relevant to personalized medicine care, as well as in the testing of novel biotherapeutics to determine whether EPR is a factor in the efficacy conditions of a new drug or candidate agent.

Another aspect provided herein relates to methods and compositions related to the use of targeted jNP for MR-imaging of target-specific tumor localization (e.g., a molecular signature of a tumor).

Target-specific tumor localization of jNPs and hence target-specific MR-imaging of tumors could give insight into the molecular signature of tumors non-invasively. In addition, this technique can provide key information akin to "personalized medicine biopsy information' in determining the right kind of therapy especially for tumors that are not easily biopsied.

FIG. 5A shows that jNPs shorten T2* relaxivity, thus distinguishing jNP+ tumors from jNP(−) tumors.

FIG. 5B shows that non-targeted jNPs localize to tumors in a heterotopic subcutaneous xenograft tumor model.

Figure 18:
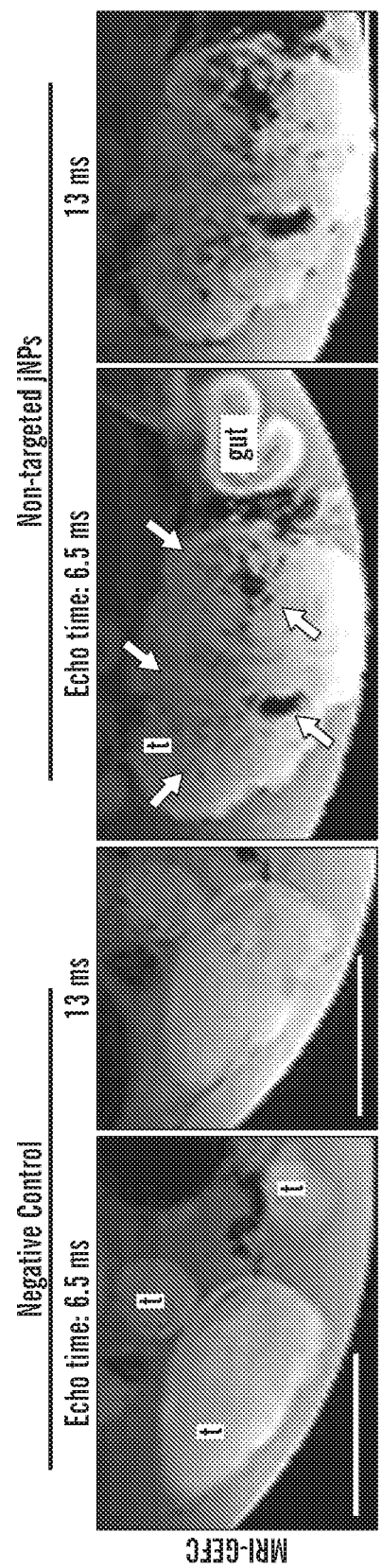
FIG. 18 Non-targeted jNPs were infused intravenously and MRI was performed 24 h later. A gradient echo with flow compensation (GEFC) was performed ex vivo on xenograft pancreatic peritoneal metastatic tumors in nude rats. Two echo times (TE) of 6.5 ms and 13 ms were used to analyse the tumors. Images show negative (darker) contrast enhancement of tumors in the presence of non-targeted jNPs in contrast to negative control. This negative contrast enhancement is increased with longer TE times from 6.5 ms to 13 ms consistent with the presence of ultrasmall superparamagnetic iron-oxide nanoparticles (USPIONS) in jNPs. Bar=0.5 cm; t, tumor; gut, small intestine.

FIG. 18 shows that non-targeted jNPs localize to multiple tumors in xenograft tumor model of pancreatic cancer peritoneal metastasis. This technique fulfills an unmet need in terms of early detection and treatment of such cancers.

Example 5: In Vitro Cell Transfection Using jNPs

Figures 17K, 17L:
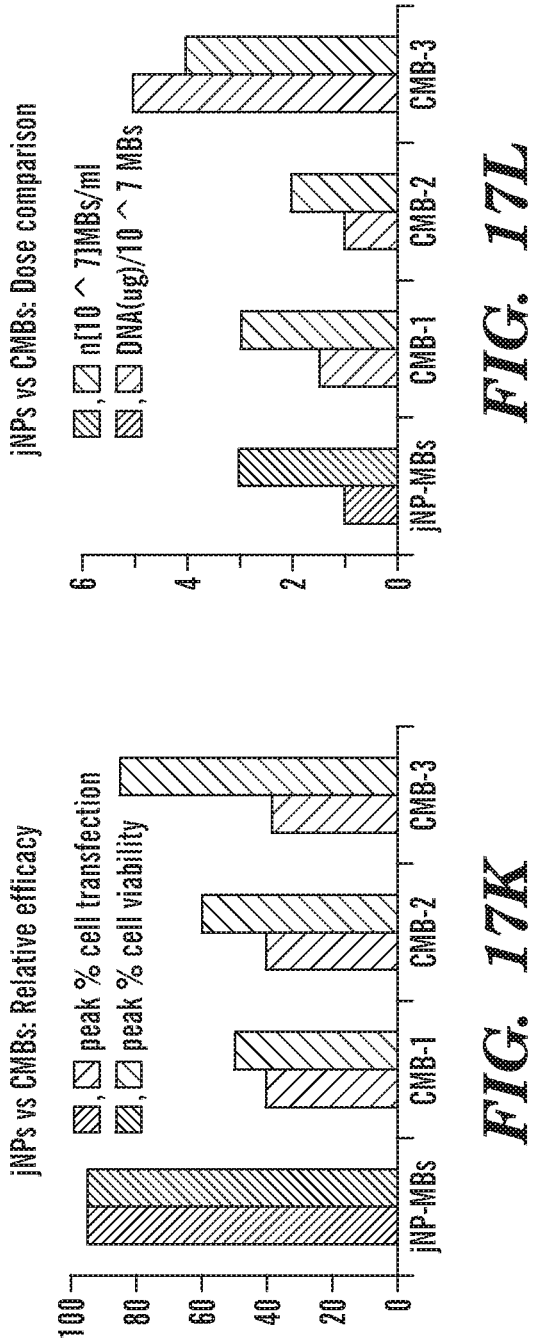
Figure 19:
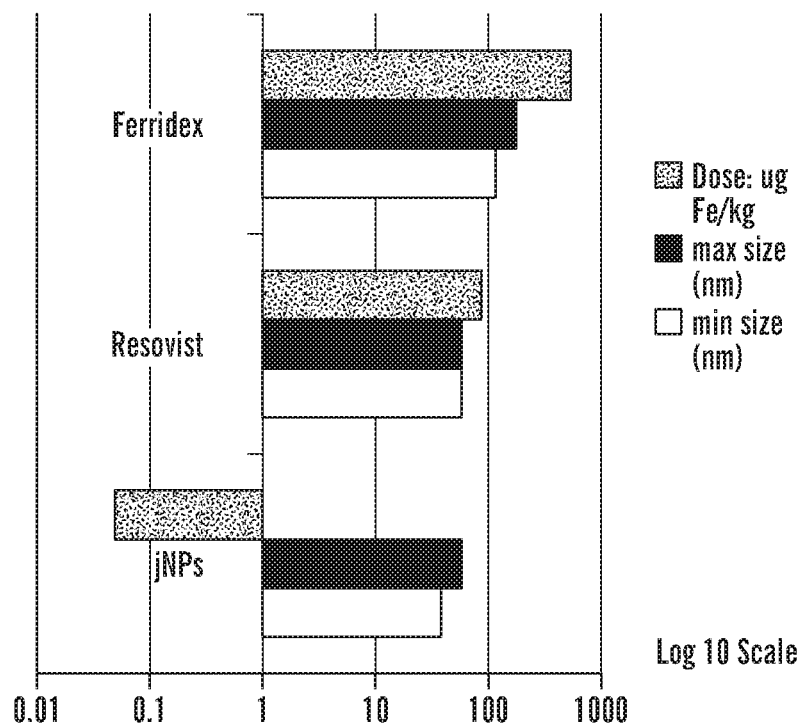
FIG. 19 Comparison with Resovist™ and Ferridex™ reveals efficiency of jNPs in that dose measured as Fe g/kg is much smaller in jNPs, assuming similar sensitivity/specificity for MRI-detection of tumors. Notably, Ferridex™ is approved for liver cancer only, indicating Ferridex™ is taken up by the normal reticuloendothelial system in the liver, which is absent or abnormal in liver tumors.

Data provided herein show that janus nanoparticle coated microbubbles (jNP-MBs) deliver DNA in vitro (% cell transfection) at least 2-fold better than previously published reports of cationic microbubbles and with les cell loss. Thus, transfection with the jNP-MBs results in less cell loss and provides a wider safety margin in terms of % cell viability. See e.g., FIGS. 17K, 17L, and 19.

In addition, the inventors have determined that DNA payloads on jNP-MBs are comparable to that reported for CMBs in the literature. Additionally, while CMB-DNA payloads are measured after 15 minutes, jNP-MB DNA payloads were measured at 1 hour and 6 hours showing stable DNA-payload binding. Although different targets and different cell lines were used in the comparator CMB studies, there is no evidence that CMBs are better than jNP-MBs, in fact data show that jNP-MBs can bind DNA equivalently and deliver DNA more efficiently and safely.

The efficacy and safety of the jNP-MBs were compared to the CMBs in the following references:

CMB-1 [VCAM-targeted; in vitro only]: Phillips L C, Klibanov A L, Wamhoff B R, Hossack J A. 2012. Intravascular ultrasound detection and delivery of molecularly targeted microbubbles for gene delivery. IEEE Transaction on Ultrasonics, Ferroelectrics, and Frequency Control 59:1596-1601.

CMB-2 [P-selectin-targeted] Jin Q, Wang Z, Yan F, Deng Z, Ni F, Wu J, Shandas R, Liu X, Zheng H. 2013. A novel cationic microbubble coated with stearic acid-modified polyethylenimine to enhance DNA loading and gene delivery by ultrasound. PLOS One 8:e76544.

CMB-3 [CD105-targeted]: Zhou Y, Gu H, Xu Y, Li F, Kuang S, Wang Z, Zhou X, Ma H, Li P, Zheng Y, Ran H, Jian J, Zhao Y, Song W, Wang Q, Wang D. 2015. Targeted antiangiogenesis gene therapy using targeted cationic microbubbles conjugated with CD105 antibody compared with untargeted cationic and neutral microbubbles. Theranostics 4(4): 399-417.

CMB-4 [P-selectin-targeted]: Xie A, Belcik T, Qi Y Morgan T K, Champaneri S A, Taylor S Davidson B P, Zhao Y, Klibanov A L, Kuliszewski M A, Leong-Poi H, Ammi A, Lindner J R. 2012. Ultrasound-mediated vascular gene transfection by cavitation of endothelial-targeted cationic microbubbles. JACC Cardiovasc Imaging 5:1253-1262.

CMB-5 [non-targeted]: Panje C M, Wang D S, Pysz M A, Paulmurugan R, Ren Y, Tranquart F, Tian L, Willmann J K. 2012. Ultrasound-mediated gene delivery with cationic versus neutral microbubbles: effect of DNA and microbubble doe on in vivo transfection efficiency. Theranostics 2012; 2:1078-1091.

CMB-6 [non-targeted]: Sun R R, Noble M L, Sun S S, Song S, Miao C H. 2014. Development of therapeutic microbubbles for enhancing ultrasound-mediated gene delivery. J Control Release 182:111-120.

CMB-7 [non-targeted]: Wang D S, Panje C, Pysz M A, Paulmurugan R, Rosenberg J, Bambhir S S, Schneider M, Willlmann J K. 2012. Cationic versus neutral microbubbles for ultrasound-mediated gene delivery in cancer. Radiology 264:721-732.

Example 6: In Vivo Ultrasound Molecular Imaging

Data provided herein show that jNP-MBs exhibit greater molecular imaging efficacy, for example, by reaching higher peak contrast intensity signals (CIS) in vivo compared to CMB-3 and CMB-4 despite using much lower doses of MBs/gram body weight.

Figure 20:
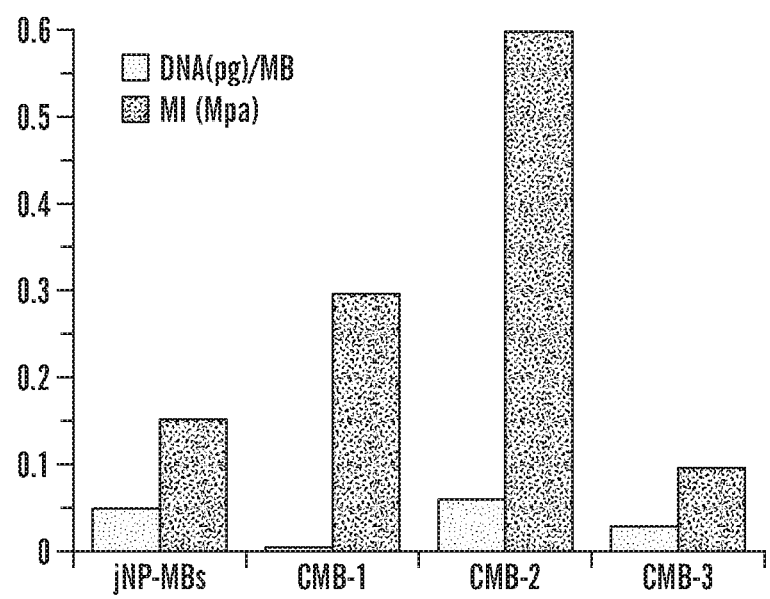
FIG. 20 Comparative analysis of in vitro DNA delivery. Comparison of amount of DNA loaded onto each microbubble (MB) measured as DNA in pictograms (pg)/MB and mechanical index (MI) used to sonoporated in megapascals (Mpa). Data for CMB-1 and CMB-2 compiled from Phillips et al. (2012) IEEE Transaction on Ultrasonics, *Ferroelectrocs and Frequency Control* 59:1596-1601, and Jin et al. (2013) *PLoS One* 8:e76544, respectively. Data for CMB-3 compiled from Zhou et al. (2015) *Theranostics* 4(4):399-417.

The dose of MBs used per gram body weight for jNP-MB experiments done in rats is 50-fold less than CMB-3 and 20-fold less than CMB-4 done in mouse models, thus indicating greater relative functional imaging efficiency (See FIG. 20; dotted 4→~fxn).

Although different in vivo models and targets are used in comparator CMB studies, there is no evidence that CMBs are better than jNP-MBs in molecular imaging. In fact, data show that jNP-MBs exhibit better ultrasound contrast-enhanced imaging as measured by CIS and relative to dose of MBs used per gram body weight.

Importantly, given that reflectivity is to the $4^{th}$ power of MB diameter, greater peak CIS cannot be attributed to size of MBs. Neither can it be attributed to absolute number of MBs used, or dose per gram body weight.

The time of sonoporation for jNP-MBs is also greater than in CMB studies. Given that MBs only last in the circulation <5-7 minutes, the ability to form molecular imaging from 10-20 minutes when using jNP-MBs indicates that jNPs impart stability in targeting and maintenance of acoustic properties of MicroMarker MBs.

Example 7: In Vivo DNA Delivery

Figure 21:
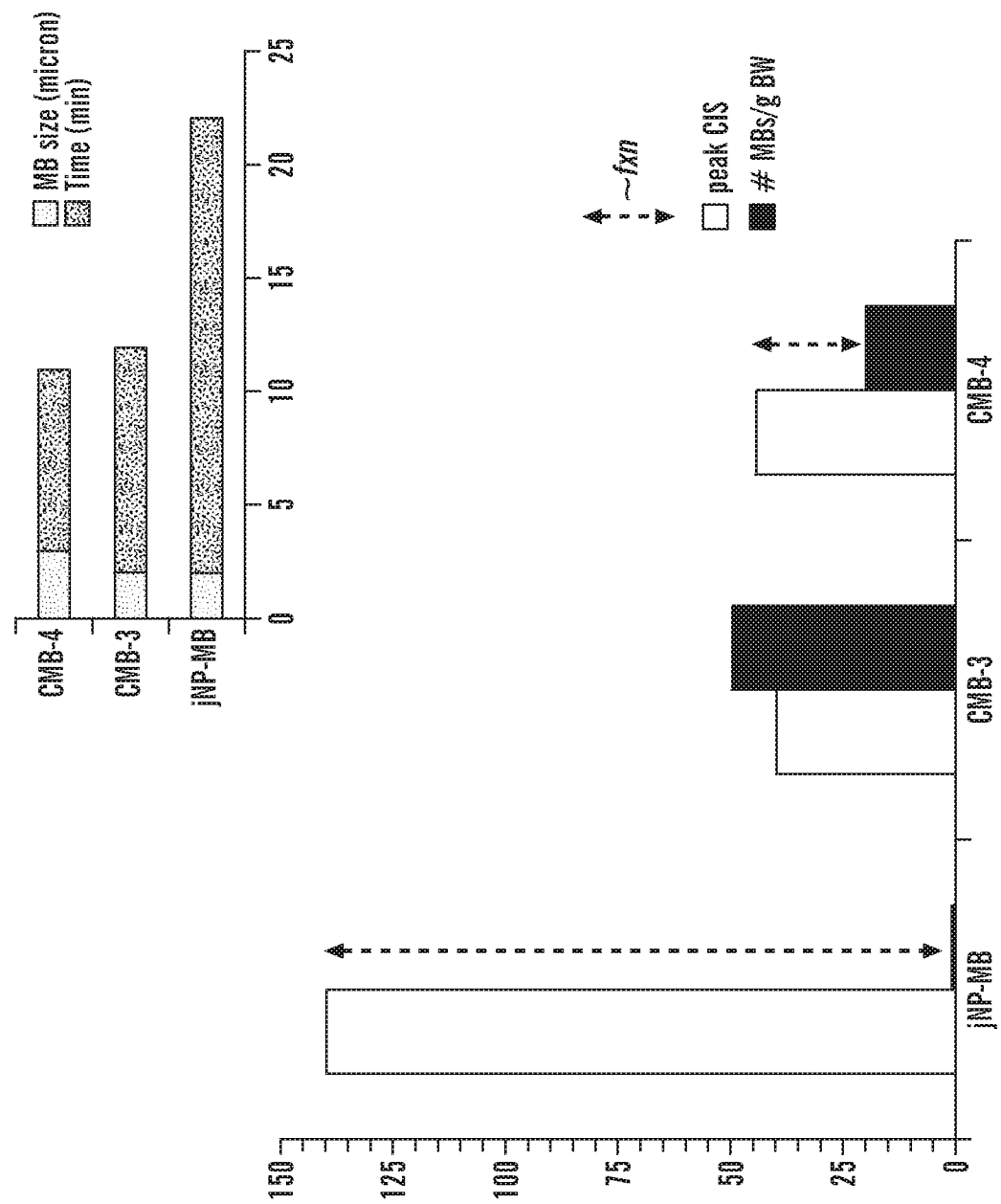
FIG. 21 Comparative analysis of in vivo ultrasound contrast-enhanced imaging or molecular imaging. Comparison in vivo molecule imaging efficacy of jNP-MB heteroplex with cationic microbubbles (CMBs) by ultrasound-contrast enhanced imaging. Efficacy is measured as peak contrast intensity signals (CIS). Inset: Comparison of microbubble size range (MB) and time when in vivo molecular imaging was performed. Data for CMB-3 and CMB-4 compiled from Zhou et al. (2015) *Theranostics* 4(4):399-417 and Xie et al. (2012) *JACC Cardiovasc Imaging* 5:1253-1262, respectively.
Figure 22A:
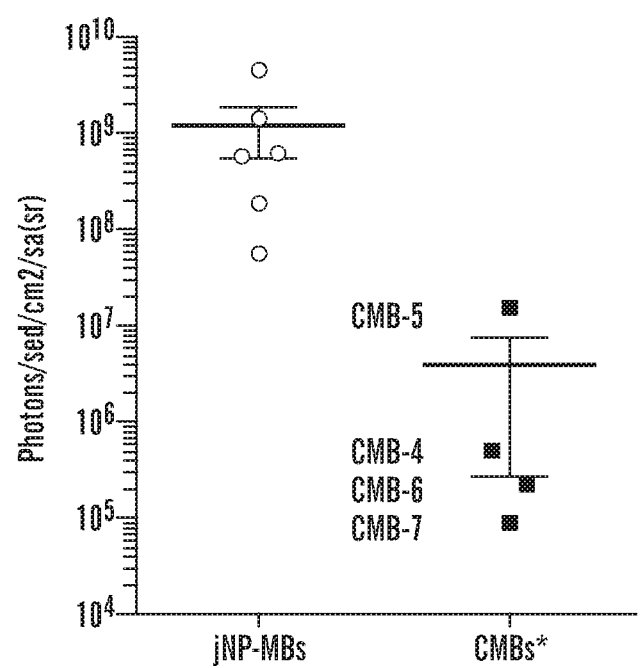
FIGS. 22A-22C Comparative analysis of in vivo ultrasound-mediated delivery of reporter function-DNA.
Figure 22B:
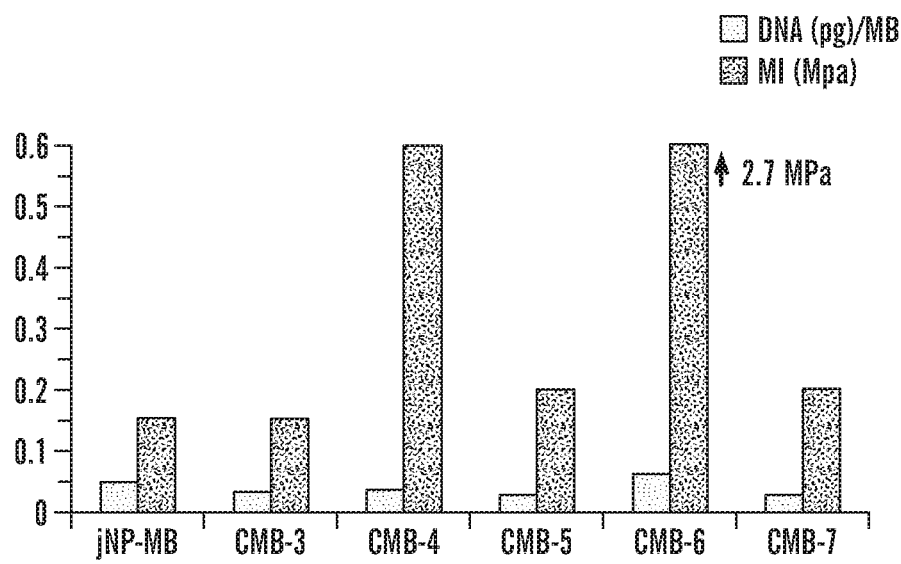
Figure 22C:
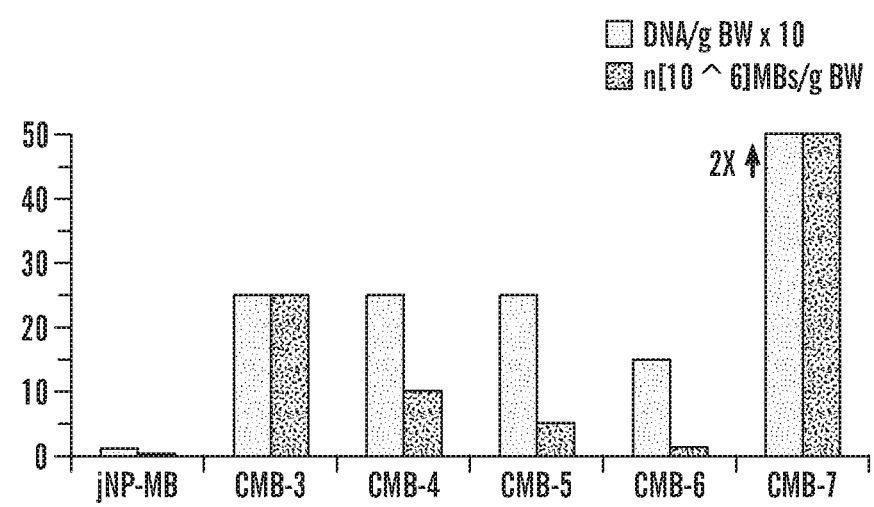

Data provided herein (see e.g., FIGS. 21A-21C) show that jNP-MBs exhibit greater efficacy in delivery of DNA in vivo, for example, by reaching higher peak fluorescence or luminescence measured as photons/sec/cm$^2$/sr by IVIS, compared to targeted CMB-4, and non-targeted CMB-5, CMB-6, and CMB-7, despite using >10-fold less DNA/g body weight, and lower doses of MBs/gram body weight.

The dose of MBs used per gram body weight for jNP-MB experiments performed in rats is 50-fold less than CMB-3 and 20-fold less than CMB-4 performed in mouse models, thus indicating greater relative functional imaging efficiency (dotted→~fxn).

Although different in vivo models and targets are used in comparator CMB studies, there is no evidence that CMBs are better than jNP-MBs in in vivo delivery of DNA. In fact, data show that jNP-MBs exhibit better delivery of DNA in vivo.

Importantly, greater DNA delivery cannot be attributed to the use of more DNA or MBs per g/BW.

The time of sonoporation for jNP-MBs is also greater than in CMB studies. Given that MBs only last in the circulation <5-7 minutes, the ability to delivery DNA at 25 minutes indicates that jNPs impart stability in targeting, DNA payload, and maintenance of acoustic properties of Micro-Marker MBs for ultrasound-mediated delivery (sonoporation).

All references cited herein are hereby incorporated by reference in their entirety.

The invention claimed is:

1. A composition comprising: a microbubble with a Janus nanoparticle associated with the surface, wherein the Janus nanoparticle is asymmetrical and comprises an ultrasmall superparamagnetic iron oxide nanoparticle (USPION) having a nucleic acid delivery face and a targeting face, and wherein the nucleic acid delivery face and the targeting face are distinct from one another,
    wherein the USPION is less than 50 nm in size, and
    wherein the nucleic acid delivery face comprises a nucleic acid molecule that is sandwiched between the microbubble and the Janus nanoparticle.

2. The composition of claim 1, wherein the superparamagnetic iron oxide nanoparticle is less than 20 nm in size.

3. The composition of claim 1, wherein the Janus nanoparticle comprises a shape that is avocado-like.

4. The composition of claim 1, wherein the antibody is selected from the group consisting of: a polyclonal antibody, a monoclonal antibody, an antibody binding fragment, a composite antibody, and a recombinant antibody.

5. The composition of claim 1, wherein the carrier face comprises a polymer.

6. The composition of claim 5, wherein the polymer comprises a polyelectrolyte.

7. The composition of claim 6, wherein the polyelectrolyte is a cationic polyelectrolyte or an anionic polyelectrolyte.

8. The composition of claim 1, wherein the Janus nanoparticle comprises an iron oxide core with a PEG brush.

9. The composition of claim 8, wherein the PEG brush is a mixed $PEG_{2K/3.4K-NH2}$ brush.

10. The composition of claim 1, wherein the iron oxide core is encapsulated within a polymer.

11. The composition of claim 10, wherein the polymer-encapsulated iron oxide core further comprises a bioactive agent.

12. The composition of claim 1, wherein the composition further comprises a bioactive agent.

13. The composition of claim 1, wherein the composition is formulated for use as a magnetic resonance imaging (MRI) contrast agent.

14. The composition of claim 13, wherein the MRI contrast agent is a negative contrast agent.

15. The composition of claim 1, wherein the composition does not activate complement when administered to a subject.

* * * * *